United States Patent

Hirata et al.

Patent Number: 5,654,322
Date of Patent: Aug. 5, 1997

[54] BIPHENYLMETHANE DERIVATIVES AND PHARMACEUTICALS CONTAINING THE SAME

[75] Inventors: Terukage Hirata; Nobuya Sakae; Koichi Tamura; Masayasu Okuhira; Hirotaka Amano; Masaharu Yokomoto; Jun Nomiyama, all of Hiroshima, Japan

[73] Assignee: Wakunaga Seiyaku Kabushiki Kaisha, Osaka, Japan

[21] Appl. No.: 386,649

[22] Filed: Feb. 10, 1995

[30] Foreign Application Priority Data

Aug. 11, 1992 [JP] Japan .................................. 4-214094
Mar. 26, 1993 [JP] Japan .................................. 5-068706
Feb. 10, 1994 [JP] Japan .................................. 6-016220
Jun. 10, 1994 [JP] Japan .................................. 6-128739

[51] Int. Cl.$^6$ ........................ C07D 261/14; A61K 31/41
[52] U.S. Cl. ............................................ 514/363; 548/138
[58] Field of Search ............................ 548/138; 514/363

[56] References Cited

U.S. PATENT DOCUMENTS 5,389,660  2/1995  Greenlee ............................. 514/381
5,434,167  7/1995  Ferrari ................................ 514/381

FOREIGN PATENT DOCUMENTS 0 501 892   9/1992  European Pat. Off. .
63-23868    2/1988  Japan .
3-27362     2/1991  Japan .
3-74369     3/1991  Japan .
3-501020    3/1991  Japan .
WO93/17681  9/1993  WIPO .

*Primary Examiner*—Robert Gerstl
*Attorney, Agent, or Firm*—Oblon, Spivak, McClelland, Maier & Neustadt, P.C.

[57] ABSTRACT

This invention relates to a biphenylmethane derivative represented by the formula (1):

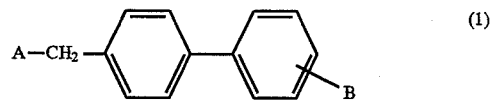

wherein A represents a group

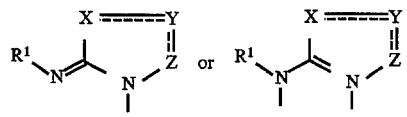

in which $R^1$, X, Y, Z and B are as defined in the Specification. The compounds have potent angiotensin II antagonist activity and anti-hypertensive effect. They have therapeutic utility for circulatory diseases such as hypertension, heart diseases and cerebral apoplexy.

13 Claims, No Drawings

BIPHENYLMETHANE DERIVATIVES AND PHARMACEUTICALS CONTAINING THE SAME

This application is a continuation-in-part of PCT/JP93/01134 filed Aug. 11, 1993.

FIELD OF THE INVENTION

The present invention relates to novel biphenylmethane derivatives and salts thereof, said derivatives and salts having a potent angiotensin II antagonist activity and also having a powerful antihypertensive activity.

DISCUSSION OF THE BACKGROUND

Angiotensin II is an active center of the renin-angiotensin system, and has powerful vasopressor action and stimulating action for the synthesis and secretion of aldosterone in the adrenal cortex. It is also known to be a substance causing hypertension. Its action is considered to be caused through a specific receptor on various target organs such as adrenal cortex, kidneys, arterioles and the peripheries of sympathetic nerves.

Known conventional examples of substances which show an antihypertensive effect by pharmacological inhibition of the renin-angiotensin system include angiotensin-converting enzyme inhibitors such as captopril and enarapril, angiotensin II antagonists and renin inhibitors. As angiotensin II antagonist out of these, saralasin ([Sar$^1$, Ala$^8$] AGII), an angiotensin II type peptide, and nonpeptide derivatives such as imidazole derivatives (Japanese Patent Laid-Open Nos. 7103/1981 and 71074/1981, and Japanese Language Laid-Open Publication (PCT) No. 501020/1991), pyrazole derivatives (Japanese Patent Laid-Open No. 218371/1991) and aminoazole derivatives (W093/17681) are already known.

The peptide derivatives, however, have difficulty in clinical applications because of their short in vivo half-life, lack of effectiveness upon oral administration and significant agonistic activities. Among the nonpeptide derivatives, none has been used clinically yet as drugs either.

With a view toward providing a clinically excellent drug under such circumstances, the present inventors have carried out an extensive investigation. As a result, it has been found that novel biphenylmethane derivatives represented by the following formula (I) have an excellent angiotensin II antagonist activity and are useful as therapeutics for circulatory diseases such as hypertension, heart diseases and cerebral apoplexy, leading to the completion of the invention.

SUMMARY OF THE INVENTION

The present invention relates to a biphenylmethane derivative represented by the following formula (1):

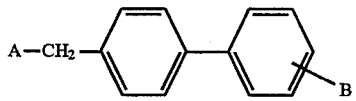

wherein A represents a group

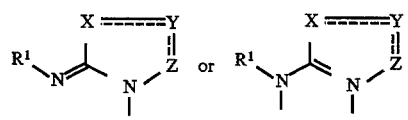

in which $R^1$ represents a hydrogen atom, a lower alkyl group, a lower-cycloalkyl group, a substituted or unsubstituted phenyl group, a substituted or unsubstituted aralkyl group, a substituted or unsubstituted acyl group or an amino acid residue; X represents an oxygen atom, a sulfur atom or a group =CH—, Y represents a nitrogen atom or a group =CR$^2$—, Z represents an oxygen atom, a nitrogen atom or a group. =CR$^3$—, said Y and Z not being hetero atoms at the same time, $R^2$ and $R^3$ each independently represents a hydrogen atom, a halogen atom, a substituted or unsubstituted lower alkyl group, a protected or unprotected carboxyl group, a lower-cycloalkyl group, a lower alkenyl group, a lower alkoxyl group, a lower alkylthio group or an aryl group or $R^2$ and $R^3$ may form a substituted or unsubstituted benzene ring together with the adjacent carbon atoms; B represents a cyano group, a protected or unprotected carboxyl group or a protected or unprotected tetrazol-5-yl group and --- shows a double bond or a single bond; or a salt thereof.

The present invention also relates to a therapeutic for circulatory diseases, which comprises the biphenylmethane derivative or the salt thereof (I) as an effective ingredient.

The present invention also relates to use of the biphenylmethane derivative or the salt thereof (1) as a pharmaceutical typified by a circulatory disease therapeutic such as a hypotensive agent.

Further, the present invention also relates to a therapeutic method of a circulatory disease, which comprises administering an effective amount of the biphenylmethane derivative or the salt thereof (I).

DETAILED DESCRIPTION OF THE PREFERRED EMBODIMENTS

In the present invention, compounds represented by the above formula (I) wherein A represents a group

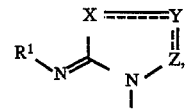

namely compounds represented by the following formula (1-a):

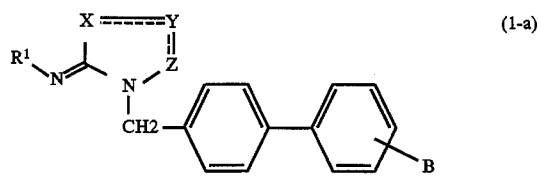

wherein R1, X, Y, Z and B have the same meanings as defined above are more preferred for their strong angiotensin II antagonist and antihypertensive action.

In the present invention, the term "lower" as used for the description of each substituent in the formula (I) means a $C_{1-7}$, preferably $C_{1-5}$ group when the substituent represents a linear or a branched group, or a $C_{3-7}$ group when the substituent is a cyclic group.

Examples of the lower alkyl group represented by $R^1$ include methyl, ethyl, n-propyl, isopropyl, n-butyl, t-butyl and n-pentyl.

Illustrative examples of the lower-cycloalkyl group represented by $R^1$ include cyclopropyl, cyclobutyl, cyclopentyl and cyclohexyl groups.

Exemplary substituted or unsubstituted phenyl groups represented by $R^1$ include—in addition to a phenyl group—phenyl groups mono-, di- or tri-substituted on their rings by a corresponding number of lower alkyl groups, halogen atoms, nitro groups, cyano groups and/or the like, such as tolyl, chlorophenyl, dichlorophenyl, trichlorophenyl, fluorophenyl, difluorophenyl, trifluorophenyl, nitrophenyl, dinitrophenyl and/or cyanophenyl groups.

Examples of the substituted or unsubstituted aralkyl groups represented by $R^1$ include—in addition to benzyl, phenethyl, benzhydryl and trityl groups—aralkyl groups mono-, di- or tri-substituted on their rings by a corresponding number of carboxyl groups, lower alkoxycarbonyl groups and/or the like, such as carboxybenzyl and/or methoxycarbonylbenzyl groups.

Examples of the substituted or unsubstituted acyl group represented by $R^1$ include alkanoyl, lower-cycloalkanoyl, lower alkenoyl, lower-cycloalkenoyl, lower alkoxycarbonyl, aralkyloxycarbonyl, carbamoyl, aromatic acyl and lower alkylsulfonyl groups.

Illustrative alkanoyl groups represented by $R^1$ include—in addition to $C_{1-10}$ alkanoyl groups such as formyl, acetyl, propionyl, butyryl, valeryl, isovaleryl, pivaroyl, hexanoyl, heptanoyl, octanoyl and nonanoyl—halo-lower alkanoyl groups such as chloroacetyl, bromoacetyl, dichloroacetyl, tri-fluoroacetyl, chloropropionyl and tetrafluoropropionyl; hydroxy-lower alkanoyl groups such as hydroxyacetyl, dihydroxyacetyl, hydroxypropionyl and hydroxybutyryl; alkoxy-lower alkanoyl groups such as methoxyacetyl, ethoxyacetyl, methoxypropionyl and ethoxypropionyl; cyano-lower alkanoyl groups such as cyanoacetyl, cyanopropyl and cyanobutyryl; cycloalkyl-lower alkanoyl groups such as cyclopropylacetyl, cyclopropylpropionyl, cyclopentylpropionyl and cyclohexylpropionyl; aryl-lower alkanoyl groups such as phenylacetyl, phenylpropionyl and phenylbutyryl; aryloxy-lower alkanoyl groups such as phenoxyacetyl, chlorophenoxyacetyl and phenoxypropionyl; and heteroaryl-lower alkanoyl groups such as thiopheneacetyl, furanacetyl and pyridineacetyl.

Examples of the lower-cycloalkanoyl group represented by $R^1$ include—in addition to cyclopropylcarbonyl, cyclobutylcarbonyl, cyclopentylcarbonyl and cyclohexylcarbonyl groups—lower-cycloalkanoyl groups substituted by one or more carboxyl groups such as carboxycyclopentylcarbonyl and carboxycyclohexylcarbonyl [including those protected by a group which is easily cleaved in vivo, such as methoxycarbonyloxymethyl, t-butoxycarbonyloxyethyl, cyclohexylcarbonyloxymethyl or (5-methyl-2-oxo-1,3-dioxol-4-yl)methyl].

Illustrative lower alkenoyl groups represented by $R^1$ include—in addition to acryloyl, methacryloyl, crotonoyl and pentenoyl groups—alkenoyl groups substituted by one or more carboxyl groups such as carboxyacryloyl and carboxycrotonoyl [including carboxyl groups protected by a group which is easily cleaved in vivo, such as methoxycarbonyloxymethyl, t-butoxycarbonyloxyethyl, cyclohexylcarbonyloxymethyl or (5-methyl-2-oxo-1,3-dioxol-4-yl) methyl].

Exemplary lower-cycloalkenoyl groups include—in addition to cyclopentenylcarbonyl and cyclohexenylcarbonyl groups—lower-cycloalkenoyl groups substituted by one or more carboxyl groups such as carboxycyclopentenylcarbonyl and carboxycyclohexenylcarbonyl [including carboxyl groups protected by a group which is easily cleaved in vivo, such as methoxycarbonyloxymethyl, t-butoxycarbonyloxyethyl, cyclohexylcarbonyloxymethyl or (5-methyl-2-oxo-1,3-dioxol-4-yl)methyl].

Exemplary lower alkoxycarbonyl groups represented by $R^1$ include methoxycarbonyl, ethoxycarbonyl, propoxycarbonyl, n-butoxycarbonyl and t-butoxycarbonyl groups.

Examples of the aralkyloxycarbonyl group represented by $R^1$ include benzyloxycarbonyl and phenethyloxycarbonyl groups.

Illustrative examples of the carbamoyl group represented by $R^1$ include—in addition to a carbamoyl group—lower-alkyl carbamoyl groups such as methylcarbamoyl, dimethylcarbamoyl and diethylcarbamoyl and cyclic carbamoyl groups such as pyrrolidinecarbonyl, piperidinecarbonyl and morpholinecarbonyl.

Examples of the aromatic acyl group represented by $R^1$ include aroyl groups such as benzoyl and naphthoyl; aroyl groups—each of which has been mono-, di- or tri-substituted on its ring by a corresponding number of lower alkyl groups, halogen atoms, cyano groups, nitro groups, halo-lower alkyl groups, halo-lower alkoxyl groups, carboxyl groups, carboxyl groups having a group which is easily cleaved in vivo, lower alkoxycarbonyl groups, alkoxyl groups, hydroxyl groups, lower alkylthio groups, mercapto groups, amino groups, lower alkanoyl groups, tetrazolyl groups and/or the like—such as toluoyl, chlorobenzoyl, fluorobenzoyl, bromobenzoyl, iodobenzoyl, cyanobenzoyl, nitrobenzoyl, trifluoromethylbenzoyl, carboxybenzoyl [including carboxybenzoyl groups having a carboxyl group protected with a group which is easily cleaved in vivo such as methoxycarbonyloxymethyl, t-butoxycarbonyloxyethyl, cyclohexylcarbonyloxymethyl or (5-methyl-2-oxo-1,3-dioxol-4-yl)methyl), methoxycarbonylbenzoyl, dimethoxycarbonylbenzoyl, 2-carboxy-6-nitrobenzoyl, 2-ethoxycarbonyl-6-nitrobenzoyl, hydroxybenzoyl, methoxybenzoyl, trifluoromethoxybenzoyl, mercaptobenzoyl, methylthiobenzoyl, aminobenzoyl, acetylbenzoyl and tetrazolylbenzoyl; heteroyl groups such as thiophenecarbonyl (thenoyl), furancarbonyl (furoyl), pyridinecarbonyl, pyrazinecarbonyl, thiazolecarbonyl, benzothiophenecarbonyl and isoxazolecarbonyl; and heteroyl groups—each of which has been mono-, di- or tri-substituted on its ring by a corresponding number of lower alkyl groups, halogen atoms, cyano groups, nitro groups, halo-lower alkyl groups, carboxyl groups, alkoxyl groups, hydroxyl groups, lower alkylthio groups, mercapto groups, amino groups, lower alkanoyl groups and/or the like—such as methylthiophenecarbonyl, chlorothiophenecarbonyl, cyanothiophenecarbonyl, nitrothiophenecarbonyl, trifluoromethylthiophenecarbonyl, carboxythiophenecarbonyl, methoxycarbonylthiophenecarbonyl, hydroxythiophenecarbonyl, methoxythiophenecarbonyl, mercaptothiophenecarbonyl, methylthiothiophenecarbonyl, aminothiophenecarbonyl, acetylthiophenecarbonyl, methylfurancarbonyl, chlorofurancarbonyl, cyanofurancarbonyl, nitrofurancarbonyl, trifluoromethylfurancarbonyl, carboxyfurancarbonyl, methoxycarbonylfurancarbonyl, hydroxyfurancarbonyl, methoxyfurancarbonyl, mercaptofurancarbonyl, methylthiofurancarbonyl, aminofurancarbonyl, acetylfurancarbonyl, methylpyridinecarbonyl, chloropyridinecarbonyl, cyanopyridinecarbonyl, nitropyridinecarbonyl, trifluoromethylpyridinecarbonyl, carboxypyridinecarbonyl, methoxycarbonylpyridinecarbonyl, hydroxypyridinecarbonyl, methoxypyridinecarbonyl, mercaptopyridinecarbonyl, methylthiopyridinecarbonyl, aminopyridinecarbonyl, acetylpyridinecarbonyl, carboxypyrazinecarbonyl, methylthiazolecarbonyl and methylisoxazolecarbonyl; benzenesulfonyl groups; and benzenesulfonyl groups—each of which has been mono-, di- or tri-substituted on its ring by a corresponding number of lower alkyl groups, halogen atoms, cyano groups, nitro groups and/or the like—such as toluenesulfonyl, fluorobenzenesulfonyl, trifluorobenzenesulfonyl, chlorobenzenesulfonyl, dichlorobenzenesulfonyl, bromobenzenesulfonyl and cyanobenzenesulfonyl.

Exemplary lower alkylsulfonyl groups represented by $R^1$ include methanesulfonyl and ethanesulfonyl.

Illustrative examples of the amino acid residue represented by $R^1$ include glycyl, leucyl, valyl, alanyl, phenylalanyl, alanyl-alanyl, glycyl-valyl and glycyl-glycyl-valyl, and also amino acid residues whose functional groups have been protected by a protective group commonly used in peptide chemistry, such as acyl or lower aralkyl.

Among the above exemplified groups $R^1$, preferred are:

$C_{1-10}$ alkanoyl groups which may each be substituted by a corresponding number of atoms and/or groups selected from halogen, hydroxy, $C_{1-7}$ alkoxyl, cyano, $C_{3-7}$ cycloalkyl, phenyl, phenoxy, chlorophenoxy, thiophene, furan and pyridine;

$C_{4-7}$ cycloalkanoyl groups which may each be substituted by a corresponding number of groups selected from carboxyl and protected carboxyl;

$C_{3-7}$ alkenoyl and $C_{4-7}$ cycloalkenoyl groups which may each be substituted by a corresponding number of groups selected from carboxyl and protected carboxyl, $C_{1-7}$ alkoxycarbonyl groups, benzyloxycarbonyl groups, phenethyloxycarbonyl groups, carbamoyl groups, $C_{1-7}$ alkylcarbamoyl groups, pyrrolidinecarbonyl groups, piperidinecarbonyl groups, morpholinecarbonyl groups, benzoyl groups which may each be substituted on its ring by 1-3 atoms and/or groups selected from $C_{1-7}$ alkyl, halogen, cyano, nitro, halo-$C_{1-7}$ alkyl, halo-$C_{1-7}$ alkoxyl, carboxyl, protected carboxyl, $C_{1-7}$ alkoxycarbonyl, $C_{1-7}$ alkoxyl, hydroxyl, $C_{1-7}$ alkylthio, mercapto, amino, $C_{1-7}$ alkanoyl and tetrazoryl, thiophenecarbonyl, furancarbonyl, pyridinecarbonyl, pirazinecarbonyl, thiazolecarbonyl or benzothiophenecarbonyl and isoxazolecarbonyl groups which may each be substituted by 1-3 atoms and/or groups selected from $C_{1-7}$ alkyl, halogen, cyano, nitro, halo-$C_{1-7}$ alkyl, carboxyl, $C_{1-7}$ alkoxyl, hydroxyl, $C_{1-7}$ alkylthio, mercapto, amino and $C_{1-7}$ alkanoyl groups, benzenesulfonyl groups which may each be substituted on the ring by 1-3 atoms and/or groups selected from $C_{1-7}$ alkyl, halogen, cyano and nitro, and $C_{1-7}$ alkylsulfonyl groups.

More preferred groups $R^1$ are:

$C_{1-10}$ alkanoyl groups which may each be substituted by a corresponding number of atoms and/or groups selected from halogen, hydroxy, $C_{1-7}$ alkoxyl, cyano, $C_{3-7}$ cycloalkyl, phenyl, phenoxy, chlorophenoxy, thiophene, furan and pyridine;

$C_{4-7}$ cycloalkanoyl groups which may each be substituted by a corresponding number of groups selected from carboxyl and protected carboxyl;

$C_{3-7}$ alkenoyl and $C_{4-7}$ cycloalkenoyl groups which may each be substituted by a corresponding number of groups selected from carboxyl and protected carboxyl, and benzoyl groups which may each be substituted on its ring by 1-3 atoms and/or groups selected from $C_{1-7}$ alkyl, halogen, cyano, nitro, halo-$C_{1-7}$ alkyl, halo-$C_{1-7}$ alkoxyl, carboxyl, protected carboxyl, $C_{1-7}$ alkoxycarbonyl, $C_{1-7}$ alkoxyl, hydroxyl, $C_{1-7}$ alkylthio, mercapto, amino, $C_{1-7}$ alkanoyl and tetrazoryl.

Particularly preferred $R^1$ are carboxy-substituted $C_{4-7}$ cycloalkenoyl groups, with a carboxy-substituted cyclopentenyl group being most preferred.

Illustrative of the substituted or unsubstituted lower alkyl group represented by $R^2$ or $R^3$ include lower alkyl groups such as methyl, ethyl, n-propyl, isopropyl, n-butyl, t-butyl and n-pentyl; hydroxy-lower alkyl groups such as hydroxymethyl, hydroxyethyl and hydroxypropyl; halo-lower alkyl groups such as chloromethyl, chloroethyl, bromomethyl, dichloromethyl and trifluoromethyl; alkoxy-lower alkyl groups such as methoxymethyl, ethoxymethyl and dimethoxyethyl; carboxy-lower alkyl groups such as carboxymethyl and carboxyethyl; and alkoxycarbonyl groups such as ethoxycarbonylmethyl and methoxycarbonylmethyl.

When $R^2$ and $R^3$ form a phenyl ring together with the adjacent carbon atoms, the ring may have thereon one or more substituents such as lower alkyl groups, lower alkoxyl groups and/or halogen atoms.

Examples of the halogen atom represented by $R^2$ or $R^3$ include fluorine, chlorine, bromine and iodine, with fluorine and chlorine atoms being preferred.

The term "the protective group" for the protected carboxyl group represented by $R^2$ or $R^3$ means a desired group capable of undergoing relatively easy cleavage and yielding a corresponding free carboxyl group. Specific examples includes those removable upon treatment under mild conditions, such as hydrolysis or catalytic reduction, such as lower alkyl groups (e.g., methyl, ethyl, n-propyl, t-butyl, etc.), aralkyl groups (e.g., benzyl, etc.), and aryl groups (e.g., phenyl, etc.); and those readily cleaved in vivo, such as lower alkanoyloxy-lower alkyl groups (e.g., acetoxymethyl, pivaloyloxymethyl, etc.), lower alkoxycarbonyloxy-lower alkyl groups (e.g., methoxycarbonyloxymethyl, 1-ethoxycarbonyloxyethyl, etc.), lower-cycloalkylcarbonyloxy-lower alkyl groups (e.g., cyclohexylcarbonyloxymethyl, cyclopentylcarbonyloxymethyl, etc.), lower alkoxymethyl groups (e.g., methoxymethyl, etc.), lactonyl groups (phthalidyl, etc.), di(lower alkyl)amino-lower alkyl groups (e.g., 1-dimethylaminoethyl, etc.), (5-methyl-2-oxol-4-yl) methyl group, and the like.

Illustrative examples of the lower-cycloalkyl group represented by $R^2$ or $R^3$ include cyclopropyl, cyclobutyl, cyclopentyl and cyclohexyl.

Illustrative examples of the lower alkenyl group represented by $R^2$ or $R^3$ include vinyl, allyl and isopropenyl.

Exemplary lower alkoxyl groups represented by $R^2$ or $R^3$ include methoxyl, ethoxyl, propoxyl, n-butoxyl and t-butoxyl.

Examples of the lower alkylthio group represented by $R^2$ or $R^3$ include methylthio, ethylthio and n-propylthio.

Illustrative examples of the aryl group represented by $R^2$ or $R^3$ include phenyl, tolyl, xylyl, mesityl and naphthyl.

Examples of the protective group usable for the protected carboxyl group represented by B include the same protective groups as those exemplified above for the protected carboxyl group represented by $R^2$ or $R^3$.

Exemplary protective groups usable for the protected tetrazol-5-yl group represented by B include triphenylmethyl, 2-tetrahydropyranyl, methoxymethyl and ethoxymethyl.

Preferred examples of the group represented by A include groups having a thiazoline, thiazole, oxazoline, oxazole, benzothiazoline, benzothiazole, benzoxazoline, benzoxazole, 1,3,4-thiadiazoline, 1,3,4-thiadiazole, 1,3,4-oxadiazoline, 1,3,4-oxadiazole, 1,2,4-thiadiazoline, 1,2,4-thiadiazole, 1,2,4-oxadiazoline, 1,2,4-oxadiazole, isoxazoline or isoxazole ring.

Preferred examples of such A include the groups represented by the following formulas (A-1)-(A-18):

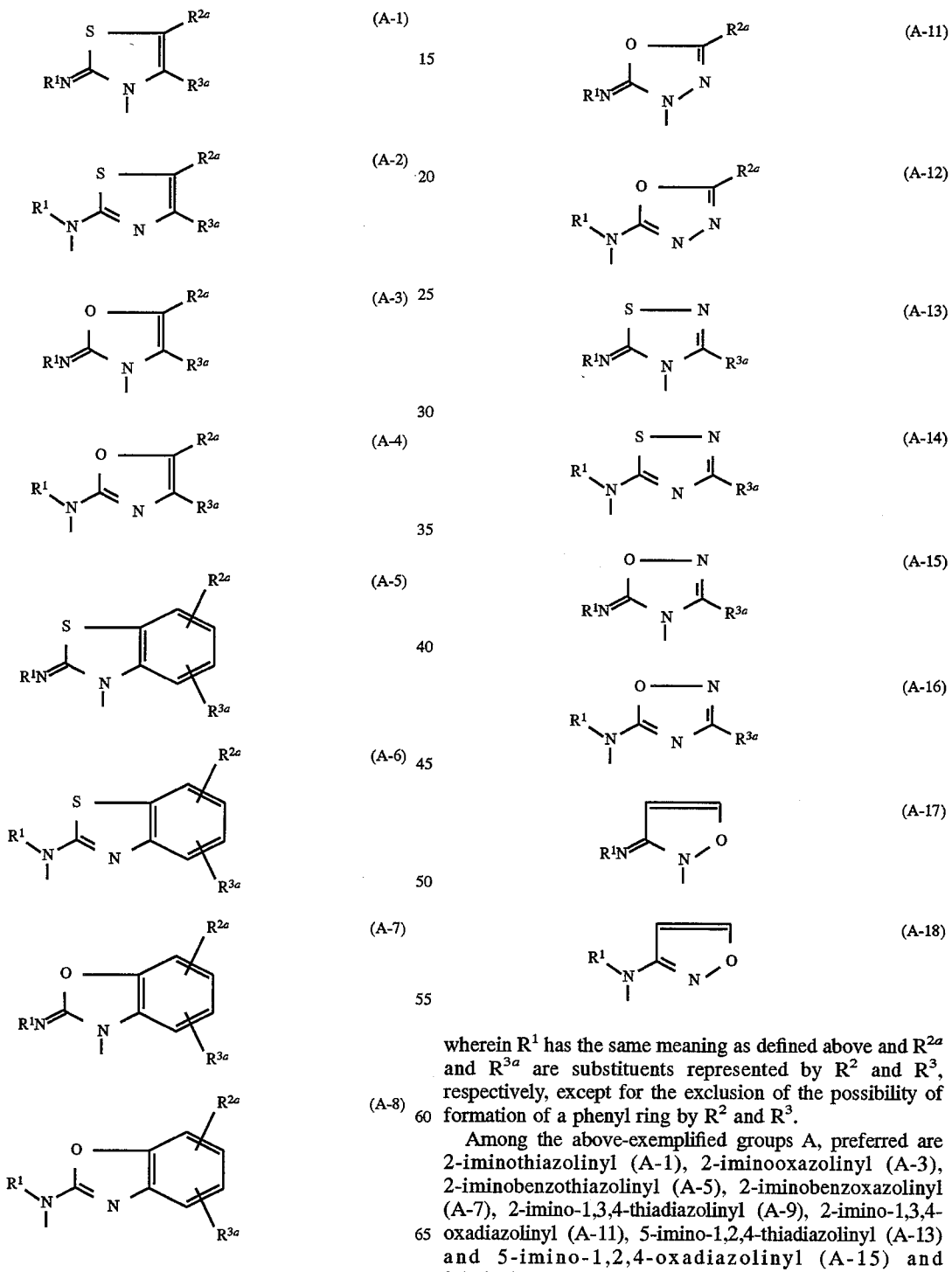

wherein $R^1$ has the same meaning as defined above and $R^{2a}$ and $R^{3a}$ are substituents represented by $R^2$ and $R^3$, respectively, except for the exclusion of the possibility of formation of a phenyl ring by $R^2$ and $R^3$.

Among the above-exemplified groups A, preferred are 2-iminothiazolinyl (A-1), 2-iminooxazolinyl (A-3), 2-iminobenzothiazolinyl (A-5), 2-iminobenzoxazolinyl (A-7), 2-imino-1,3,4-thiadiazolinyl (A-9), 2-imino-1,3,4-oxadiazolinyl (A-11), 5-imino-1,2,4-thiadiazolinyl (A-13) and 5-imino-1,2,4-oxadiazolinyl (A-15) and 3-iminoisoxazolinyl (A-17) groups. More preferred are the groups (A-1) and (A-9), with the group (A-9) being particularly preferred.

Preferred specific examples of the group represented by A include 2-acetylimino-5-ethylthiazolin-3-yl, 2-acetylimino-5-cyclopropylthiazolin-3-yl, 2-propionylimino-5-ethylthiazolin-3-yl, 2-propionylimino-5-cyclopropylthiazolin-3-yl, 2-butylimino-5-ethylthiazolin-3-yl, 2-butylimino-5-cyclopropylthiazolin-3-yl, 2-cyclopropylcarbonylimino-5-ethylthiazolin-3-yl, 2-cyclopropylcarbonylimino-5-cyclopropylthiazolin-3-yl, 2-valeroylimino-5-methylthiazolin-3-yl, 2-valeroylimino-5-ethylthiazolin-3-yl, 2-valeroylimino-5-cyclopropylthiazolin-3-yl, 2-cyclobutylcarbonylimino-5-ethylthiazolin-3-yl, 2-cyclopentylcarbonylimino-5-ethylthiazolin-3-yl, 2-trifluoroacetylimino-5-ethylthiazolin-3-yl, 2-benzoylimino-5-ethylthiazolin-3-yl, 2-(2-chlorobenzoyl)imino-5-ethylthiazolin-3-yl, 2-(2-chlorobenzoyl)imino-5-n-propyl-5 thiazolin-3-yl, 2-(2-fluorobenzoyl)imino-5-ethylthiazolin-3-yl, 2-(2-bromobenzoyl)imino-5-ethylthiazolin-3-yl, 2-(2-iodobenzoyl)imino-5-ethylthiazolin-3-yl, 2-(2-nitrobenzoyl)imino-5-ethylthiazolin-3-yl, 2-(2-methoxybenzoyl)imino-5-ethylthiazolin-3-yl, 2-(2-toluoyl)imino-5-ethylthiazolin-3-yl, 2-(2-trifluoromethylbenzoyl)imino-5-ethylthiazolin-3-yl, 2-(2-trifluoromethoxybenzoyl)imino-5-ethylthiazolin-3-yl, 2-(2-cyanobenzoyl) imino-5-ethylthiazolin-3-yl, 2-(2-methoxycarbonylbenzoyl)imino-5-ethylthiazolin-3-yl, 2-(2-ethoxycarbonylbenzoyl)imino-5-ethylthiazolin-3-yl, 2-(2-carboxybenzoyl)imino-5-ethylthiazolin-3-yl, 2-(2-sulfobenzoyl)imino-5-ethylthiazolin-3-yl, 2-(2,6-dichlorobenzoyl)imino-5-ethylthiazolin-3-yl, 2-(1-naphthoyl) imino-5-ethylthiazolin-3-yl, 2-(2-naphthoyl)imino-5-ethylthiazolin-3-yl, 2-(2-tenoyl)imino-5-ethylthiazolin-3-yl, 2-(3-tenoyl)imino-5-ethylthiazolin-3-yl, 2-(2-furoyl)imino-5-ethylthiazolin-3-yl, 2-(3-furoyl)imino-5-ethylthiazolin-3-yl, 2-nicotinoylimina-5-ethylthiazolin-3-yl, 2-isonicotinoylimino-5-ethylthiazolin-3-yl, 2-picolinoylimino- 5-ethylthiazolin-3-yl, 2-(2-carboxynicotinoyl)imino-5-ethylthiazolin-3-yl, 2-(4-carboxynicotinoyl)imino-5-ethylthiazolin-3-yl, 2-(3-carboxyisonicotinoyl)imino-5-ethylthiazolin-3-yl, 2-(3-carboxypicolinoyl)imino-5-ethylthiazolin-3-yl, 2-phenylacetylimino-5-ethylthiazolin-3-yl, 3-phenylpropionylimino-5-ethylthiazolin-3-yl,2-phenoxyacetylimino-5-ethylthiazolin-3-yl,2-thiopheneacetylimino-5-ethylthiazolin-3-yl, 2-furaneacetylimino-5-ethylthiazolin-3-yl, 2-ethanesulfonylimino-5-ethylthiazolin-3-yl, 2-propanesulfonylimino-5-ethylthiazolin-3-yl, 2-benzenesulfonylimino-5-ethylthiazolin-3-yl, 2-(4-toluenesulfonyl)imino-5-ethylthiazolin-3-yl, 2-acetylimino-5-ethylthiazoline-4-carboxy-3-yl, 2-acetylimino-5-n-propylthiazoline-4-carboxy-3-yl, 2-acetylimino-5-cyclopropylthiazoline-4-carboxy-3-yl, 2-propionylimino-5-ethylthiazoline-4-carboxy-3-yl, 2,propionylimino-5-n-propylthiazoline-4-carboxy-3-yl, 2-propionylimino-5-cyclopropylthiazoline-4-carboxy-3-yl, 2-butyrylimino-5-ethylthiazoline-4-carboxy-3-yl, 2-butyrylimino-5-n-propylthiazoline-4-carboxy-3-yl, 2-butyrylimino-5-cyclopropylthiazoline-4-carboxy-3-yl, 2-cyclopropylcarbonylimino-5-ethylthiazoline-4-carboxy-3-yl, 2-cyclopropylcarbonylimino-5-n-propylthiazoline-4-carboxy-3-yl, 2-cyclopropylcarbonylimino-5-n-butylthiazoline-4-carboxy-3-yl, 2-cyclobutylcarbonylimino-5-ethylthiazoline-4-carboxy-3-yl, 2-cyclobutylcarbonylimino-5-n-propylthiazoline-4-carboxy-3-yl, 2-cyclopentylcarbonylimino-5-ethylthiazoline-4-carboxy-3-yl, 2-cyclopentylcarbonylimino-5-n-propylthiazoline-4-carboxy-3-yl, 2-benzoylimino-5-ethylthiazoline-4-carboxy-3-yl, 2-(2-chlorobenzoyl)imino-5-ethylthiazoline-4-carboxy-3-yl, 2-(2-chlorobenzoyl)imino-5-n-propylthiazoline-4-carboxy-3-yl, 2-(2-trifluoromethylbenzoyl) imino-5-ethylthiazoline-4-carboxy-3-yl, 2-(2-trifluoromethylbenzoyl)imino-5-n-propylthiazoline-4-carboxy-3-yl, 2-(2-methoxycarbonylbenzoyl)imino-5-ethylthiazoline-4-carboxy-3-yl, 2-(2-methoxycarbonylbenzoyl)imino-5-n-propylthiazoline-4-carboxy-3-yl, 2-(2-carboxybenzoyl)imino-5-ethylthiazoline-4-carboxy-3-yl, 2-(2-carboxybenzoyl)imino-5-n-propylthiazoline-4-carboxy-3-yl, 2-propionylimino-benzothiazolin-3-yl, 2-cyclopropylcarbonylimino-benzothiazolin-3-yl, 2-cyclopropylcarbonylimino-5-,6-dimethyl-benzothiazolin-3-yl, 2-acetylimino-5-methyl-1,3,4-thiadiazolin-3-yl, 2-acetylimino-5-ethyl-1,3,4-thiadiazolin-3-yl, 2-acetylimino-5-n-propyl-1,3,4-thiadiazolin-3-yl, 2-acetylimino-5-cyclopropyl-1,3,4-thiadiazolin-3-yl, 2-acetylimino-5-n-butyl-1,3,4-thiadiazolin-3-yl, 2-acetylimino-5-ethylthio-1,3,4-thiadiazolin-3-yl, 2-propionylimino- 5-methyl-1,3,4-thiadiazolin-3-yl, 2-propionylimino-5-ethyl-1,3,4-thiadiazolin-3-yl, 2-propionylimino-5-n-propyl-1,3,4-thiadiazolin-3-yl, 2-propionylimino-5-cyclopropyl-1,3,4-thiadiazolin-3-yl, 2-propionylimino-5-n-butyl-1,3,4-thiadiazolin-3-yl, 2-butyrylimino-5-methyl-1,3,4-thiadiazolin-3-yl, 2-butyrylimino-5-ethyl-1,3,4-thiadiazolin-3-yl, 2-butyrylimino-5-n-propyl-1,3,4-thiadiazolin-3-yl, 2-butyrylimino-5-cyclopropyl-1,3,4-thiadiazolin-3-yl, 2-butyrylimino-5-n-butyl-1,3,4-thiadiazolin-3-yl, 2-butyrylimino-5-t-butyl-1,3,4-thiadiazolin-3-yl, 2-butyrylimino-5-ethylthio-1,3,4-thiadiazolin-3-yl, 2-butyrylimino-5-hydroxymethyl-1,3,4-thiadiazolin-3-yl, 2-butyrylimino-5-chloro-1,3,4-thiadiazolin-3-yl, 2-butyrylimino-5-bromo-1,3,4-thiadiazolin-3-yl, 2-cyclopropylcarbonylimino-5-methyl-1,3,4-thiadiazolin-3-yl, 2-cyclopropylcarbonylimino-5-ethyl-1,3,4-thiadiazolin-3-yl, 2-cyclopropylcarbonylimino-5-n-propyl-1,3,4-thiadiazolin-3-yl, 2-cyclopropylcarbonylimino-5-cyclopropyl-1,3,4-thiadiazolin-3-yl, 2-cyclopropylcarbonylimino-5-n-butyl-1,3,4-thiadiazolin-3-yl, 2-cyclopropylcarbonylimino-5-t-butyl-1,3,4-thiadiazolin-3-yl, 2-cyclopropylcarbonylimino-5-ethylthio-1,3,4-thiadiazolin-3-yl, 2-cyclopropylcarbonylimino-5-hydroxymethyl-1,3,4-thiadiazolin-3-yl, 2-cyclopropylcarbonylimino-5-chloro- 1,3,4-thiadiazolin-3-yl, 2-cyclopropylcarbonylimino-5-bromo-1,3,4-thiadiazolin-3-yl, 2-vareloylimino-5-methyl-1,3,4-thiadiazolin-3-yl, 2-vareloylimino-5-ethyl-1,3,4-thiadiazolin-3-yl, 2-valeroylimino-5-n-5 propyl-1,3,4,thiadiazolin-3-yl, 2-valeroylimino-5-cyclopropyl-1,3,4-thiadiazolin-3-yl, 2-vareloylimino-5-n-butyl-1,3,4-thiadiazolin-3-yl, 2-valeroylimino-5-ethylthio-1,3,4-thiadiazolin-3-yl, 2-cyclobutylcarbonylimino-5-ethyl-1,3,4-thiadiazolin-3-yl, 2-cyclopentylcarbonylimino-5-ethyl-1,3,4-thiadiazolin-3-yl, 2-(2-carboxycyclopentylcarbonyl)imino-5-ethyl-1,3,4-thiadiazolin-3-yl, 2-cyclohexylcarbonylimino-5-ethyl-1,3,4-thiadiazolin-3-yl, 2-(2-carboxycyclohexylcarbonyl)imino-5-ethyl-1,3,4-thiadiazolin-3-yl, 2-(2-carboxycyclopentenylcarbonyl)imino-5-methyl-1,3,4-thiadiazolin-3-yl, 2-(2-carboxycyclopentenylcarbonyl)imino-5-ethyl-1,3,4-thiadiazolin-3-yl, 2-(2-carboxycyclopentenylcarbonyl)imino-5-propyl-1,3,4-thiadiazolin-3-yl, 2-(2- carboxycyclopentenylcarbonyl)imino-5-isopropyl-1,3,4-thiadiazolin-3-yl, 2-(2-carboxycyclopentenylcarbonyl)imino-5-cyclopropyl-1,3,4-thiadiazolin-3-yl, 2-pivaroylimino-5-ethyl-1,3,4-thiadiazolin-3-yl, 2-hexanoylimino-5-ethyl-1,3,4-thiadiazolin-3-yl, 2-crotonoylimino-5-ethyl-1,3,4-thiadiazolin-3-yl, 2-methoxyacetylimino-5-ethyl-1,3,4-thiadiazolin- 3-yl, 2-ethoxyacetylimino-5-ethyl-1,3,4-thiadiazolin-3-yl, 2-trifluoroacetylimino-5-ethylthi-1,3,4-thiadiazolin-3-yl, 2-benzoylimino-5-ethyl-1,3,4-thiadiazolin-3-yl, 2-(2-chlorobenzoyl)imino-5-methyl-5 1,3,4-thiadiazolin-3-yl, 2-(2-chlorobenzoyl)imino-5-ethyl-1,3,4-thiadiazolin-3-yl, 2-(2-chlorobenzoyl)imino-5-n-propyl-1,3,4-thiadiazolin-3-yl, 2-(2-chlorobenzoyl)imino-5-n-butyl-1,3,4-thiadiazolin-3-yl, 2-(2-chlorobenzoyl)imino-5-chloro-1,3,4-thiadiazolin-3-yl, 2-(3-chlorobenzoyl)imino-5-ethyl-1,3,4-thiadiazolin-3-yl, 2-(4-chlorobenzoyl)imino-5-ethyl-1,3,4-thiadiazolin-3-yl, 2-(2-fluorobenzoyl)imino-5-ethyl-1,3,4-thiadiazolin-3-yl, 2-(3-fluorobenzoyl)imino-5-ethyl-1,3,4-thiadiazolin-3-yl, 2-(4-fluorobenzoyl)imino-5-ethyl-1,3,4-thiadiazolin-3-yl, 2-(2-bromobenzoyl)imino-5-ethyl-1,3,4-thiadiazolin-3-yl, 2-(3-bromobenzoyl)imino-5-ethyl-1,3,4-thiadiazolin-3-yl, 2-(4-bromobenzoyl)imino-5-ethyl-1,3,4-thiadiazolin-3-yl, 2-(2-iodobenzoyl)imino-5-ethyl-1,3,4-thiadiazolin-3-yl, 2-(2-nitrobenzoyl)imino-5-ethyl-1,3,4-thiadiazolin-3-yl, 2-(3-nitrobenzoyl)imino-5-ethyl-1,3,4-thiadiazolin-3-yl, 2-(4-nitrobenzoyl)imino-5-ethyl-1,3,4-thiadiazolin-3-yl, 2-(2-methoxybenzoyl)imino-5-ethyl-1,3,4-thiadiazolin-3-yl, 2-(3-methoxybenzoyl)imino-5-ethyl-1,3,4-thiadiazolin-3-yl, 2-(4-methoxybenzoyl)imino- 5-ethyl-1,3,4-thiadiazolin-3-yl, 2-(2-toluoyl)imino-5-ethyl-1,3,4-thiadiazolin-3-yl, 2-(3-toluoyl)imino-5-ethyl-1,3,4-thiadiazolin-3-yl, 2-(4-toluoyl)imino-5-ethyl-1,3,4-thiadiazolin-3-yl, 2-(2-trifluoromethylbenzoyl)imino-5-ethyl-1,3,4-thiadiazolin-3-yl, 2-(3-trifluoromethylbenzoyl)imino-5-ethyl-1,3,4-thiadiazolin-3-yl, 2-(4-trifluoromethylbenzoyl)imino-5-ethyl-1,3,4-thiadiazolin-3-yl, 2-(2-trifluoromethoxybenzoyl)imino-5-ethyl-1,3,4-thiadiazolin-3-yl, 2-(2-cyanobenzoyl)imino-5-ethyl-1,3,4-thiadiazolin-3-yl, 2-(3-cyanobenzoyl) imino-5-ethyl-1,3,4-thiadiazolin-3-yl, 2-(4-cyanobenzoyl)imino-5-ethyl-1,3,4-thiadiazolin-3-yl, 2-(2-methoxycarbonylbenzoyl) imino-5-ethyl-1,3,4-thiadiazolin-3-yl, 2-(3-methoxycarbonylbenzoyl)imino-5-ethyl-1,3,4-thiadiazolin-3-yl, 2-(4-methoxycarbonylbenzoyl)imino-5-ethyl-1,3,4-thiadiazolin-3-yl, 2-(2-carboxybenzoyl)imino-5-methyl-1,3,4-thiadiazolin-3-yl, 2-(2-carboxybenzoyl)imino-5-ethyl-1,3,4-thiadiazolin-3-yl, 2-(2-carboxybenzoyl)imino-5-propyl-1,3,4-thiadiazolin-3-yl, 2-(2-carboxybenzoyl)imino-5-isopropyl-1,3,4-thiadiazolin-3-yl, 2-(2-carboxybenzoyl) imino-5-cyclopropyl-1,3,4-thiadiazolin-3-yl, 2-(3-carboxybenzoyl)imino-5-ethyl-1,3,4-thiadiazolin-3-yl, 2-(4-carboxybenzoyl)imino-5-ethyl-1,3,4-thiadiazolin-3-yl, 2-(2-sulfobenzoyl)imino- 5-ethyl-1,3,4-thiadiazolin-3-yl, 2-(3-sulfobenzoyl)imino-5-ethyl-1,3,4-thiadiazolin-3-yl, 2-(4-sulfobenzoyl)imino-5-ethyl-1,3,4-thiadiazolin-3-yl, 2-(2,4-dimethoxybenzoyl)imino-5-ethyl-1,3,4-thiadiazolin-3-yl, 2-(1-naphthoyl)imino-5-ethyl-1,3,4-thiadiazolin-3-yl, 2-(2-naphthoyl)imino-5-ethyl-1,3,4-thiadiazolin-3-yl, 2-(2-tenoyl)imino-5-ethyl-1,3,4-thiadiazolin-3-yl, 2-(3-tenoyl)imino-5-ethyl-1,3,4-thiadiazolin-3-yl, 2-(3-chloro-2-tenoyl)imino-5-ethyl-1,3,4-thiadiazolin-3-yl, 2-(3-chloro-4-methanesulfonyltenoyl)imino-5-ethyl-1,3,4-thiadiazolin-3-yl, 2-(3-carboxy-2-tenoyl)imino-5-ethyl-1,3,4-thiadiazolin-3-yl, 2-(2-carboxy-3-tenoyl)imino-5-ethyl-1,3,4-thiadiazolin-3-yl, 2-(4-carboxy-3-tenoyl)imino-5-ethyl-1,3,4-thiadiazolin-3-yl, 2-(2-furoyl) imino-5-ethyl-1,3,4-thiadiazolin-3-yl, 2-(3-furoyl)imino-5-ethyl-1,3,4-thiadiazolin-3-yl, 2-(3-carboxy-2-furoyl)imino-5-ethyl-1,3,4-thiadiazolin-3-yl, 2-(2-carboxy-3-furoyl)imino-5-ethyl-1,3,4-thiadiazolin-3-yl, 2-(4-carboxy-3-furoyl)imino-5-ethyl-1,3,4-thiadiazolin-3-yl, 2-nicotinoylimino-5-ethyl-1,3,4-thiadiazolin-3-yl, 2-isonicotinoylimino-5-ethyl-1,3,4-thiadiazolin-3-yl, 2-picolinoylimino-5-ethyl-1,3,4-thiadiazolin-3-yl-2-(2-methylthionicotinoyl)imino-5-ethyl-1,3,4-thiadiazolin-3-yl, 2-(4-methyl-1,2,3-thiazole-5-carbonyl)imino-5-ethyl-1,3,4-thiadiazolin- 3-yl, 2-(5-methyl-isoxazole-3-carbonyl)imino-5-ethyl-1,3,4-thiadiazolin-3-yl, 2-phenylacetylimino-5-ethyl-1,3,4-thiadiazolin-3-yl, 2-(2-chlorophenyl)acetylimino-5-ethyl-1,3,4-thiadiazolin-3-yl, 3-phenylpropionylimino-5-ethyl-1,3,4-thiadiazolin-3-yl, 4-phenylbutyrylimino-5-ethyl-1,3,4-thiadiazolin-3-yl, 3-phenyl-2-(t-butoxycarbonylamino) propionylimino-5-ethyl-1,3,4-thiadiazolin-3-yl, 3-phenyl-2-aminopropionylimino-5-ethyl-1,3,4-thiadiazolin-3-yl, 2-phenoxyacetylimino-5-ethyl-1,3,4-thiadiazolin-3-yl, 2-(2-chlorophenoxyacetyl)imino-5-ethyl-1,3,4-thiadiazolin-3-yl, 2-thiopheneacetylimino-5-ethyl-1,3,4-thiadiazolin-3-yl, 2-furaneacetylimino-5-ethyl-1,3,4-thiadiazolin-3-yl, 2-cinnamoylimino-5-ethyl-1,3,4-thiadiazolin-3-yl, 2-(3-cyclohexyl)propanoylimino-5-ethyl-1,3,4-thiadiazolin-3-yl, 2-ethanesulfonylimino-5-ethyl-1,3,4-thiadiazolin-3-yl, 2-propanesulfonylimino-5-ethyl-1,3,4-thiadiazolin-3-yl, 2-benzenesulfonylimino-5-ethyl-1,3,4-thiadiazolin-3-yl, 2-(4-toluenesulfonyl)imino-5-ethyl-1,3,4-thiadiazolin-3-yl, 2-(2-carboxythiophene-3-sulfonyl)imino-5-ethyl-1,3,4-thiadiazolin-3-yl, 2-(2-methoxycarbonylbenzenesulfonyl) imino-5-ethyl-1,3,4-thiadiazolin-3-yl, 2-(2-carboxybenzenesulfonyl)imino-5-ethyl-1,3,4-thiadiazolin-3-yl, 2-acetylimino-5-ethylthiooxazolin- 3-yl, 2-propionylimino-5-ethylthiooxazolin-3-yl, 2-propionylimino-5-ethylthiooxazolin-3-yl, 2-butyrylimino-5-ethyloxazolin-3-yl, 2-cyclopropylcarbonylimino-5-emethyloxazolin-3-yl, 2-(2-chlorobenzoyl)imino-5-ethyloxazolin-3-yl, 2-(2-carboxybenzoyl)imino-5-ethyloxazolin-3-yl, 2-propionylimino-benzoxazolin-3-yl, 2-cyclopropylcarbonylimino-benzoxazolin-3-yl, 2-acetylimino-5-ethyl-1,3,4-oxadiazolin-3-yl, 2-propionylimino-5-ethyl-1,3,4-oxadiazolin-3-yl, 2-butyrylimino-5-ethyl-1,3,4-oxadiazolin-3-yl, 2-cyclopropylcarbonylimino-5-ethyl-1,3,4-oxadiazolin-3-yl, 2-(2-chlorobenzoyl)imino-5-ethyl-1,3,4-oxadiazolin-3-yl, 2-(2-carboxybenzoyl)imino-5-ethyl-1, 3,4-oxadiazolin-3-yl, [N-methyl-N-(5-methylthiazol-2-yl )]amino, [N-n-butyl-N-(5-ethylthiazol-2-yl)]amino, [N-acetyl-N-(5-ethylthiazol-2-yl)]amino, [N-acetyl-N-(5-cyclopropylthiazol-2-yl)]-amino, [N-propionyl-N-(5-ethylthiazol-2-yl)]amino, [N-propionyl-N-(5-n-propylthiazol-2-yl)]amino, [N-propionyl-N-(5-cyclopropylthiazol-2-yl)]amino, [N-butyryl-N-(5-ethylthiazol-2-yl)]amino, [N-butyryl-N-(5-n-propylthiazol-2-yl)]amino, [N-butyryl-N-(5-cyclopropylthiazol-2-yl)] amino, [N-cyclopropylcarbonyl-N-(5-ethylthiazol-2-yl)] amino, [N-cyclopropylcarbonyl-N-(5-n-propylthiazol-2-yl)] amino, [N-cyclopropylcarbonyl-N-(5-cyclopropylthiazol-2-yl)]amino, [N-valeroyl-N-(5-ethylthiazol- 2-yl)]amino, [N-valeroyl-N-(5-n-propylthiazol-2-yl)]amino, [N-valeroyl-N-(5-cyclopropylthiazol-2-yl)]amino, [N-hexanoyl-N-(5-ethylthiazol-2-yl)]amino, [N-hexanoyl-N-(5-n-propylthiazol-2-yl)]-amino, [N-hexanoyl-N-(5-cyclopropylthiazol-2-yl)]amino, [N-cyclobutylcarbonyl-N-(5-ethylthiazol-2-yl)]amino, [N-cyclobutylcarbonyl-N-(5-n-propylthiazol-2-yl)]amino, [N-cyclobutylcarbonyl-N-(5-cyclopropylthiazol-2-yl)]-amino, [N-t-butyloxycarbonyl-N-

(5-ethylthiazol-2-yl)]-amino, [N-ethoxycarbonyl-N-(5-ethylthiazol-2-yl)]amino, [N-benzoyl-N-(5-ethylthiazol-2-yl)]amino, [N-(2-chlorobenzoyl)-N-(5-ethylthiazol-2-yl)] amino, [N-(2,6-dichlorobenzoyl)-N-(5-ethylthiazol-2-yl)] amino, [N-benzyl-N-(5-ethylthiazol-2-yl)]amino, [N-(3-methoxycarbonylbenzyl)-N-(5-ethylthiazol-2-yl)]amino, [N-(3-carboxybenzyl)-N-(5-ethylthiazol-2-yl)]amino, [N-(2-(1H-tetrazol-5-yl)benzyl)-N-(5-ethylthiazol-2-yl)]-amino, [N-benzyloxycarbonyl-N-(5-ethylthiazol-2-yl)]-amino, [N-phenacyl-N-(5-ethylthiazol-2-yl)]amino, [N-(2-cyanophenyl)-N-(5-ethylthiazol-2-yl)]amino, [N-(2,4-dinitrophenyl)-N-(5-ethylthiazol-2-yl)]amino, [N-(4-morpholinocarbonyl)-N-(5-ethylthiazol-2-yl)]amino, [N-nicotinoyl-N-(5-ethylthiazol-2-yl)]amino, [N-(2-chloronicotinoyl)-N-(5-ethylthiazol-2-yl)]amino, [N-(4-methyl-1,2,3-thiadiazol-5-carbonyl-N-(5-ethylthiazol-2-yl)] amino, [N-ethanesulfonyl-N-(5-ethylthiazol-2-yl)]-amino, [N-n-propanesulfonyl-N-(5-ethylthiazol-2-yl)]-amino, [N-benzenesulfonyl-N-(5-ethylthiazol-2-yl)]-amino, [N-(2-chlorobenzenesulfonyl)-N-(5-ethylthiazol-2-yl)]amino, N-(5-methylthiazole-4-carboxy-2-yl)amino, N-(5-ethylthiazole-4-carboxy-2-yl)amino, N-(5-n-propylthiazole-4-carboxy-2-yl)amino, N-(5-n-butylthiazole-4-carboxy-2-yl)amino, N-(5-n-pentylthiazole-4-carboxy-2-yl)amino, [N-acetyl-N-(5-ethylthiazole-4-carboxy-2-yl)]amino, [N-acetyl-N-(5-n-propylthiazole-4-carboxy-2-yl)]amino, [N-acetyl-N-(5-cyclopropylthiazole-4-carboxy-2-yl)] amino, [N-propionyl-N-(5-ethylthiazole-4-carboxy-2-yl)] amino, [N-propionyl-N(5-n-propylthiazole-4-carboxy-2-yl) ]amino, [N-propionyl-N-(5-cyclopropylthiazole-4-carboxy-2-yl)]amino, [N-propionyl-N-(5-cyclopropylthiazole-4-carboxy-2-yl)]amino, [N-butyryl-N-(5-ethylthiazole-4-carboxy-2-yl)]amino, [N-butyryl-N-(5-n-propylthiazole-4-carboxy-2-yl)]amino, [N-butyryl-N-(5-cyclopropylthiazole-4-carboxy-2-yl)]amino, [N-cyclopropylcarbonyl-N-(5-ethylthiazole-4-carboxy-2-yl)]amino, [N-cyclopropylcarbonyl-N-(5-n-propylthiazole-4-carboxy-2-yl)]amino, [N-cyclobutylcarbonyl-N-(5-cyclopropylthiazole-4-carboxy-2-yl)]amino, [N-cyclobutylcarbonyl-N-(5-n-butylthiazole-4-carboxy-2-yl)]ammino, [N-benzoyol-N-(5-ethylthiazole-4-carboxyl-2-yl)]amino, [N-(2-chlorobenzoyl)-N-(5-ethylthiazole-4-carboxy-2-yl)]amino, [N-(2-chlorobenzoyl)-N-(5-n-propylthiazole-4-carboxy-2-yl)]amino, [N-propionyl-N-(benzothiazole-2-yl)]amino, [N-cyclopropanecarbonyl-N-5-(benzothiazole-2-yl)]amino and [N-cyclopropanecarbonyl-N-(5,6-dimethyl-benzothiazole-2-yl)]amino.

The compounds (1) of the present invention can be converted into both pharmacologically acceptable acid addition salts and base addition salts. Exemplary acid addition salts include (a) salts with mineral acids such as hydrochloric acid and sulfuric acid, (b) salts with organic carboxylic acids such as formic acid, citric acid, trichloroacetic acid, trifluoroacetic acid, fumaric acid and maleic acid, and (c) salts with sulfonic acids such as methanesulfonic acid, benzenesulfonic acid, p-toluenesulfonic acid, mesitylene-sulfonic acid and naphthalenesulfonic acid. On the other hand, illustrative base addition salts include (a) salts with alkali metals such as sodium and potassium, (b) salts with alkaline earth metals such as calcium and magnesium, (c) ammonium salts, (d) salts with nitrogen-containing organic bases such as trimethylamine, triethylamine, tributylamine, pyridine, N,N-dimethylaniline, N-methylpiperidine, N-methylmorpholine, diethylamine, cyclohexylamine, procaine, dibenzylamine, N-benzyl-β-phenethylamine, 1-ephenamine and N,N'-dibenzylethylenediamine.

Among these salts, alkali metal salts are more preferred. Particularly preferred are the potassium salts because they show good bioavailability when orally administered. From the standpoint of bioavailability in oral administration and pharmacological effects, the most preferred compound is dipotassium 2-[[5-ethyl-3[2'-(1H-tetrazol-5-yl)-biphenyl-4-yl]methyl-1,3,4-thiadiazolin-2-yliden]aminocarbonyl]-1-cyclopentenecarboxylate.

The compounds (1) of the present invention may be not only in unsolvated forms but also in hydrated or solvated forms. The compounds according to the present invention therefore embrace those in any crystalline form and their hydrated and solvated products.

Further, the compounds (1) of the present invention include those containing an asymmetric carbon atom so that they can exist as optically active substances. These optically active substances are also embraced in the compounds of the present invention. The compounds (1) of the present invention also include those containing two or more asymmetric carbon atoms. They can exist as different stereoisomers (cis-form, transform). These stereoisomers are also included in the compounds of the present invention.

Each compound of the present invention represented by the formula (1) can be prepared by various processes. Preferred are Preparation Processes 1 and 2 shown by the following reaction schemes:

Preparation Process 1:

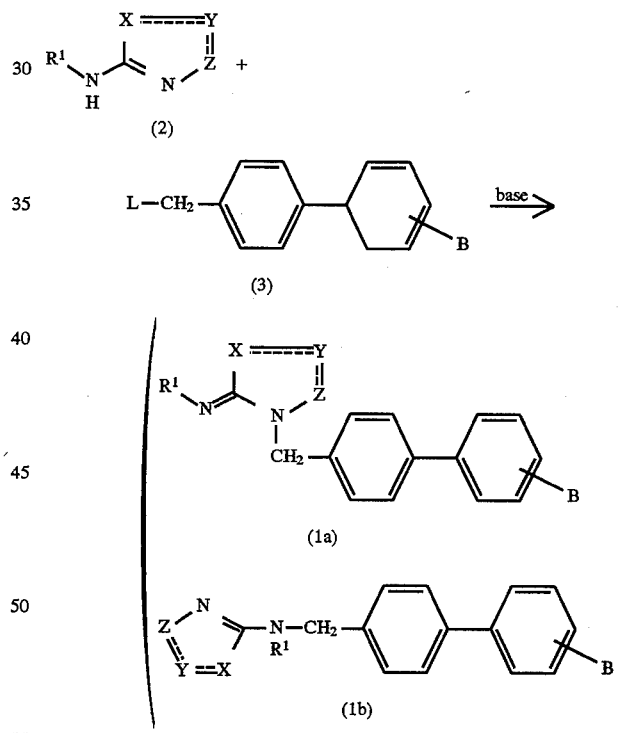

wherein $R^1$ B, X, Y Z and — have the same meanings as defined above and L represents a halogen atom or a sulfonyloxy group.

Namely, a diazole derivative represented by the formula (2) and a biphenylmethyl halide derivative represented by the formula (3) are condensed together in the presence of a base, whereby a compound (1a) and/or a compound (1b) can be prepared.

Examples of the base usable in the above reaction include sodium hydride, lithium hydride, potassium carbonate, sodium carbonate, sodium alcoholates, t-butoxypotassium, sodium hydroxide, potassium hydroxide, triethylamine and diisopropylethylamine. Any solvent can be used here as long as it does not affect the reaction. Exemplary usable solvents include aprotonic polar solvents such as N,N-dimethylformamide and dimethylsulfoxide; ethers such as diethyl ether, tetrahydrofuran, dioxane, monoglymes and diglymes; halogenated hydrocarbons such as methylene chloride, chloroform and carbon tetrachloride; and alcohols such as methanol, ethanol and propanol.

As a reaction accelerator, a phase transfer catalyst can be added. Examples of the phase transfer catalyst include quaternary ammonium salts such as tetramethylammonium chloride, tetraoctylammonium chloride and tetrabutylammonium bromide; pyridinium salts such as N-neopentyl-4-(N',N'-dimethylamino)pyridium chloride and N-(2-ethylhexyl)-4-(N',N'-dimethylamino)pyridinium chloride; and quaternary phosphonium salts such as tetrabutylphosphonium bromide and tetraphenylphosphonium bromide.

The reaction may ordinarily be conducted at −30° C. to 150° C., preferably 10° C. to 100° C. The reaction time may generally be 10 minutes to 24 hours, preferably 1 hour to 10 hours.

A particularly preferred example of the reaction is the one in which the metal salt of an azole derivative (2) is prepared in an aprotonic polar solvent such as N,N-dimethylformamide by using sodium hydride as a base and then the resulting metal salt is reacted with a biphenylmethyl halide derivative (3) at a temperature of from 0° C. to room temperature.

Examples of the halogen atom represented by L in the compound (3) include fluorine, chlorine, bromine and iodine. Illustrative of the sulfonyloxy group include alkylsulfonyloxy groups such as methanesulfonyloxy, ethanesulfonyloxy and trifluoromethanesulfonyloxy, and arylsulfonyloxy groups such as benzenesulfonyloxy and p-toluenesulfonyloxy.

Preparation Process 2:

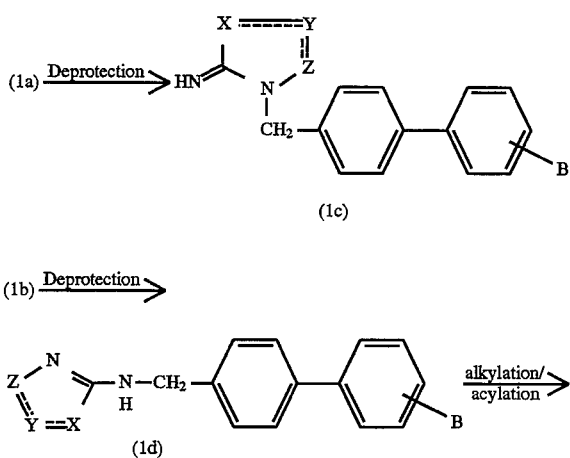

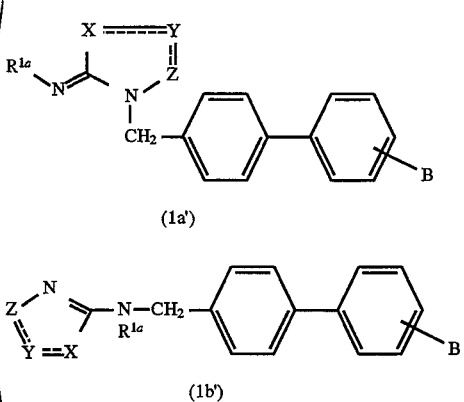

In the condensation shown in Preparation Process 1, the ratio of (1a) to (1b) so formed differs depending on the kind of $R^1$ in the azole derivative (2). By employing as $R^1$ a protective group which not only has reaction selectivity but also is readily cleaved, as needed, either the compound (1a) or the compound (1b) can be obtained selectively. The iminoazoline derivative (1c) or aminoazole derivative (1d) is then available by the deprotection of the compound (1a) or (1b), respectively. Further, the compound (1a') or (1b') in which $R^1$ is other than a hydrogen atom can be obtained by alkylation or acylation of the compound (1c) or (1d) with a desired alkylating agent or acylating agent as needed.

Any known reaction can be employed for the deprotection. For example, the deprotection can be conducted by reacting the compound (1b) at a temperature of from room temperature to 100° C. in an aqueous alkaline solution such as an aqueous sodium hydroxide solution, aqueous potassium hydroxide solution or aqueous sodium carbonate solution or in an acidic solution such as hydrochloric acid or acetic acid while using a solvent miscible with water, such as ethanol, methanol, tetrahydrofuran or N,N-dimethylformamide, or in a solventless manner.

The alkylation can be conducted by reacting an iminoazoline derivative or aminoazole derivative with an alkylating agent, which corresponds to a desired alkyl group and can be a dialkylsulfuric acid, alkyl iodide or alkyl bromide, at a temperature of from room temperature to 150° C. or so in a solution such as N,N-dimethylformamide or N-methylpyrrolidone in the presence of a base, preferably sodium carbonate or potassium carbonate.

The acylation, on the other hand, can be conducted by any desired reaction employed generally for the acylation of amino groups. Described specifically, the acylation can be conducted by reacting an iminoazoline derivative or aminoazole derivative with an acyl chloride or an acid anhydride, which corresponds to a desired acyl group, in an aprotonic polar solvent—such as a halogenated hydrocarbon, e.g., methylene chloride, chloroform, carbon tetrachloride or chlorobenzene; an aromatic hydrocarbon, e.g., benzene or toluene; an ether, e.g., tetrahydrofuran or dioxane; acetonitrile; or N,N-dimethylformamide—at 0° C. to room temperature in the presence or absence of a base such as pyridine, picoline, N,N-dimethylaniline, N-methylmorpholine, dimethylamine, triethylamine, sodium carbonate or potassium carbonate; or by reacting the iminoazoline derivative or aminoazole derivative with an acid such as formic acid or acetic acid or an acid anhydride thereof at a temperature of from room temperature to 150° C.

In Preparation Process 1 and Preparation Process 2, when the carboxyl group or tetrazol-5-yl group represented by B has a protective group, the protective group can be removed as needed.

When B represents a protected tetrazol-5-yl group, it is desired to conduct the protection by reacting the compound in a water-containing alcohol, or an ether, such as dioxane or tetrahydrofuran, which contains hydrochloric acid, acetic acid or the like, at room temperature or so for approximately 1–10 hours. When B represents a protected carboxyl group, on the other hand, any desired known reaction can be employed. For example, the deprotection can be conducted by reacting the compound at a temperature of from room temperature to 100° C. in an aqueous alkaline solution such as an aqueous sodium hydroxide solution, aqueous potassium hydroxide solution or aqueous sodium carbonate solution or in an acidic solution such as hydrochloric acid or acetic acid.

When B represents a cyano group, it can be converted into a tetrazol-5-yl group by adding a 1,3 dipolar ring to it while using a metal azide compound such as tri-$C_1$-C18 alkyltin azide, tri-$C_1$-$C_{18}$ alkylsilyl azide or sodium azide in accordance with a known method (Japanese Patent Laid-Open No. 23868/1988). Described specifically, a tetrazol-5-yl derivative can be obtained by adding a metal azide compound to the corresponding cyano derivative in a solvent such as benzene or toluene, reacting them under heat and then treating the reaction product with hydrochloric acid or the like.

The biphenyl derivative (3) can be prepared in a manner known to date (Japanese Patent Laid-Open No. 23868/1988, 27362/1991 or 74369/1991; J. Org. Chem., 56, 2395–2400 (1991); or the like).

The compound (1) so obtained can be converted into its salt in a manner known per se in the art. Described specifically, to convert the compound (1) into its alkali metal salt such as the potassium salt, it is only necessary to dissolve the compound (1) in a solution of an alkali hydroxide such as potassium hydroxide or sodium hydroxide so that it is precipitated as a salt. It is preferred to employ, as the alkali hydroxide solution, a solution of an alkali hydroxide dissolved in an amount at least equivalent to that of the compound (1) in water, methanol, ethanol, n-propyl alcohol, isopropyl alcohol, acetone or the like. The compound (1) is dissolved in the alkali hydroxide solution so obtained. The dissolving temperature can be determined between room temperature and a temperature high enough to conduct the dissolution under heat as desired depending on the compound (1). In addition, a salt precipitation method can be chosen as desired, because some salts precipitate when simply left over but some salts do not precipitate until the solvent is removed to some extent.

The salt of the compound (1) so obtained can be purified as needed in a manner known per se in the art, for example, by dissolving the salt in one or more solvents selected from water, methanol, ethanol, n-propyl alcohol, isopropyl alcohol or acetone and then recrystallizing it from the solvents.

Action (1) Inhibitory action against the binding with angiotensin II (AII) receptor, using cultured rat aortic smooth muscle cells The present test was conducted in accordance with the method reported by Chiu et al. in European Journal of Pharmacology, 157, 13–21(1988), though after some modifications.

Vascular smooth muscle cells, which had been separated from the aorta of a male Wistar rat and cultured on a 24-well multiplate were washed with a buffer of pH 7.4 containing 0.25% bovine serum albumin, 100 mM NaCl and 50 mM Tris, followed by the further addition of 0.1 ml of the buffer to each well. To each well, $^{125}$I-AII (final concentration: $2\times10^{-10}$ M) was added together with or without a test compound to give a total volume of 0.2 ml. Then the wells were incubated for one hour at room temperature to make the $^{125}$I-AII and the test compound competitively bind to the vascular smooth muscle cells. Each well was thereafter washed with an ice-cold buffer three times to remove unbound $^{125}$I-AII. To the cells, 0.2 ml of a 1 mol/l solution of sodium hydroxide was added to solubilize the bound $^{125}$I-AII. A bound amount of 125I-AII contained in the resulting cell solution was measured by a gamma counter.

The above test was conducted for each compound at different concentrations of 3 doses or more. The inhibition rate against the specific binding with $^{125}$I-AII at each concentration was calculated in accordance with an equation to be set out subsequently herein. From the inhibition rate so calculated, the concentration ($IC_{50}$) of the test compound required for 50% substitution of the $^{125}$I-AII specific binding was calculated from linear regression line.

As a result of the test, compounds according to the present invention showed $IC_{50}$ values presented in Table 1, respectively.

$$\text{Inhibition rate (\%)} = \frac{\begin{array}{c}\text{(Specifically bound amount in the}\\ \text{absence of a compound} -\\ \text{specifically bound amount in the}\\ \text{presence of the compound)}\end{array}}{\begin{array}{c}\text{(Specifically bound amount in the}\\ \text{absence of the compound)}\end{array}} \times 100$$

TABLE 1

| Compound No. | $IC_{50}$ (M) |
| --- | --- |
| (1) | $8.0 \times 10^{-9}$ |
| (2) | $1.3 \times 10^{-8}$ |
| (7) | $6.8 \times 10^{-9}$ |
| (11) | $6.5 \times 10^{-9}$ |
| (12) | $3.2 \times 10^{-8}$ |
| (13) | $1.4 \times 10^{-8}$ |
| (14) | $9.8 \times 10^{-9}$ |
| (19) | $1.5 \times 10^{-8}$ |
| (23) | $3.1 \times 10^{-8}$ |
| (31) | $1.7 \times 10^{-8}$ |
| (34) | $1.0 \times 10^{-8}$ |
| (68) | $5.7 \times 10^{-9}$ |
| (126) | $3.2 \times 10^{-8}$ |
| (242) | $1.3 \times 10^{-8}$ |

(2) Inhibitory activity to angiotensin II contraction in longitudinal ileac muscles excised from a guinea pig A Hartley male guinea pig (350–450 g in weight) was sacrificed under exsanguination, followed by the excision of its ileum.

A longitudinal muscle tissue (2 cm long) was prepared from the ileum in a manner known per se in the art. The sample was suspended in a 20-ml Magnus cylinder filled with a Tylode solution [composition (mM): NaCl 137, KCl 2.7, $CaCl_2$ 1.88, $MgCl_2$ 1.1, $NaH_2PO_4$ 0.4, $NaH_2CO_3$ 11.8 and glucose 5.6). The Tylode solution was incubated at 37° C. and saturated with a mixed gas consisting of 95% $O_2$+5% $CO_2$. Using an isometric transducer ("TB-611T", manufactured by Nihon Kohden Corporation), variations in contraction were measured. The measurement results were recorded on a computer ("PC-9801", manufactured by. NEC Corporation).

Under a load of 0.5 g initial tension, the longitudinal muscle sample was equilibrated in a nutrient solution for about one hour while being washed therewith at intervals of 15 minutes. Then, contracture by the administration of 80 mM of KCl was repeated twice. After conforming that the contraction occurred stably, the following test was conducted.

First, 10-8M angiotensin II was administered to the sample and its maximum contraction was recorded. The test compound was then administered to the sample and they were reacted for 20 minutes. Administered again was $10^{-8}$ M angiotensin II and the maximum contraction was measured. The maximum angiotensin II contractions before and after the administration of the test compound were compared, whereby a contraction inhibition rate (%) was determined in accordance with the below-described equation. This test was repeated at increased concentrations of the test compound. A 50% contraction inhibition concentration ($IC_{50}$) was determined in accordance with a linear regressive calculation of the contraction inhibition rates.

As a result, compounds according to the present invention showed $IC_{50}$ values presented in Table 2.

$$\text{Contraction Inhibition rate (\%)} = \frac{\text{(Maximum contraction before administration of a compound} - \text{Maximum contraction after administration of the compound)}}{\text{Maximum contraction before administration of the compound}} \times 100$$

TABLE 2

| Compound No. | $IC_{50\ (M)}$ |
|---|---|
| (1) | $2.3 \times 10^{-8}$ |
| (2) | $1.1 \times 10^{-8}$ |
| (7) | $2.1 \times 10^{-8}$ |
| (11) | $2.6 \times 10^{-8}$ |
| (12) | $2.8 \times 10^{-8}$ |
| (13) | $2.4 \times 10^{-8}$ |
| (14) | $3.6 \times 10^{-8}$ |
| (19) | $7.5 \times 10^{-9}$ |
| (23) | $8.0 \times 10^{-9}$ |
| (31) | $1.0 \times 10^{-8}$ |
| (34) | $2.9 \times 10^{-8}$ |
| (68) | $4.9 \times 10^{-9}$ |
| (126) | $8.0 \times 10^{-10}$ |
| (130) | $6.5 \times 10^{-10}$ |
| (131) | $8.4 \times 10^{-10}$ |
| (132) | $4.0 \times 10^{-10}$ |
| (137) | $9.0 \times 10^{-10}$ |
| (143) | $6.4 \times 10^{-10}$ |
| (158) | $5.1 \times 10^{-10}$ |
| (242) | $7.4 \times 10^{-9}$ |
| (244) | $7.6 \times 10^{-10}$ |
| (245) | $3.5 \times 10^{-10}$ |

(3) Antihypertensive action on renal hypertensive rats (non-invasive)

Renal hypertensive rats were each prepared by constricting the left renal artery of a male SD rat (age: 6 weeks old, body weight: 200–220 g) with a silver clip (inner diameter: 0.017 inch) under anesthesia. The rats whose systolic blood pressure arose to 160 mmHg or higher in 4–8 weeks after the constriction of the renal artery were used for the test. The rats were maintained on food and water ad libitum until immediately before the test was started. Each test compound which was suspended in 0.5% methyl cellulose was orally administered at 10 mg/kg. After the administration of the test compound, the systolic blood pressure was measured periodically by a non-invasive sphygmomanometer ("BP-98", manufactured by SOFTLON K.K.). In accordance with the following equation, a decreased rate of blood pressure (%) was calculated from the blood pressure values before and after the administration of the compound. The results are shown in Table 3.

$$\text{Decreased rate of blood pressure (\%)} = \frac{\text{(Blood pressure before administration of the compound} - \text{Blood pressure after administration of the compound)}}{\text{Blood pressure before administration of the compound}} \times 100$$

TABLE 3

| Compound No. | Maximum action (%) |
|---|---|
| (19) | 25.9 |
| (23) | 26.3 |

(4) Antihypertensive action on renal hypertensive rats (invasive)

Renal hypertensive rats were each prepared by constricting the left renal artery of a male SD rat (age: 6 weeks old, body weight: 190–220 g) with a silver clip (inner diameter: 0.017 inch) under anesthesia. Antihypertensive action was studied employing the rats whose mean blood pressure arose to 150 mmHg or higher in 4–8 weeks after the constriction of the renal artery. On the day before the test, a cannula for measure of blood pressure was inserted into the femoral artery of each of the renal hypertensive rats under anesthesia and was allowed to remain in the artery. The rats were maintained on food and water ad libtum until immediately before the test was started. The cannula so inserted was connected to a blood pressure transducer and a mean blood pressure was recorded on a polygraph. After the blood pressure became stable, the test compound which was suspended in 0.5% carboxymethyl cellulose was orally administered to each of the rats at 3 mg/kg. In accordance with the following equation, a decreased rate of blood pressure (%) was calculated from the blood pressure values before and after the administration of the test compound. The results are shown in Table 4.

$$\text{Decreased rate of blood pressure (\%)} = \frac{\text{(Blood pressure before administration of the compound} - \text{Blood pressure after administration of the compound)}}{\text{Blood pressure before administration of the compound}} \times 100$$

TABLE 4

| Compound No. | Maximum action (%) |
|---|---|
| (126) | 27.6 |
| (130) | 41.2 |
| (158) | 38.4 |
| (242) | 29.5 |

(5) Antihypertensive action on renal hypertensive rats (invasive, low dosage)

In a similar manner to the test (4) except that the test compound was orally administered to each of the rats at 0.3 mg/kg, antihypertensive action of the test compound was studied. The results are shown in Table 5.

TABLE 5

| Test compound | Decrease in blood pressure (%) |
| --- | --- |
| Compound (130) | 10.8 |
| 2K salt of Compound (130) | 23.0 |
| 1K salt of Compound (130) | 19.8 |
| 2Na salt of Compound (130) | 12.9 |

(6) Inhibitory action of the test compounds orally administered to arousal, normal-blood-pressure rats whose blood pressures had intentionally been raised by angiotensin II (intravenously injected at 0.1 µg/kg) (invasive)

On the day before the test, a cannula for the measurement of blood pressure and another cannula for the administration of a solution of angiotensin II (AII) in physiological saline (intravenously administered at 0.1 µg/kg) were inserted into the right femoral artery and the right femoral vein of each of the male SD rats (body weight: 200–350 g), respectively, under anesthesia. The rats were maintained on food and water ad libitum until immediately before the test was started. The former cannula so inserted was connected to a blood pressure transducer and the mean blood pressure was recorded on a polygraph. The solution of AII in physiological saline was then intravenously administered to each of the rats to raise its blood pressure. The blood-pressure raising response was repeated several times. After it was confirmed that the response became stable, the test compound which had been suspended in 0.5% carboxymethyl cellulose was orally administered to the rat at 1.0 mg/kg. In accordance with the following equation, an inhibitory rate (%) of blood pressure increase was calculated from the blood pressure increases before and after the administration of the test compound. The results are shown in Table 6.

$$\text{Inhibition rate of blood pressure increase (\%)} = \frac{\text{(Blood pressure increase before administration of the compound)} - \text{(Blood pressure increase after administration of the compound)}}{\text{Blood pressure increase before administration of the compound}} \times 100$$

TABLE 6

| Test compound | Inhibition of blood pressure increase (%) |
| --- | --- |
| Compound (130) | 54.2 |
| 2K salt of Compound (130) | 84.6 |

(7) Measurement of bioavailability in rat

SD Male rats of 6 weeks old (5 rats a group) were fasted overnight. The test compound was then administered to each of the rats at 3 mg/kg intravenously after dissolved in physiological saline and orally after suspended in 0.5% carboxymethyl cellulose, respectively. After administration, blood was collected periodically. From the blood so collected, plasma was separated by centrifugation. The test compound in the plasma was determined by high-performance liquid chromatography and based on it, areas under concentration (AUC) in intravenous administration and oral administration were found respectively. Bioavailability (BA) of the test compound for the rats was calculated in accordance with the following equation: The test results are shown in Table 7.

$$BA\ (\%) = \frac{\text{Area under concentration when orally administered}}{\text{Area under concentration when intravenously administered}} \times 100$$

TABLE 7

| Test compound | BA (%) |
| --- | --- |
| Compound (130) | 12.0 |
| 2K salt of Compound (130) | 42.8 |

As described above, the compound (1) according to the present invention and its salt both have a potent angiotensin II antagonist activity, inhibitory action to smooth muscle contraction and antihypertensive action so that they are effective for the treatment and prevention of hypertension.

When the compounds (I) and their salts according to the present invention are used as treating agents for circulatory diseases, they can be formulated into compositions together with a pharmaceutically-acceptable carrier for parenteral administration such as injection or rectal administration or for oral administration in the form of a solid or a liquid.

Compositions of this invention for use as injections can take the form of pharmaceutically-acceptable germ-free water, non-aqueous solutions, suspensions or emulsions. Exemplary suitable non-aqueous carriers, diluents, solvents and vehicles include propylene glycol, polyethylene glycol, vegetable oils such as olive oil, and injectable organic esters such as ethyl oleate. These preparations can contain one or more auxiliary agents, for example, antiseptics, wetting agents, emulsifiers and dispersants. These formulations can be sterilized, for example, by filtering them through a bacterial filter or by mixing, immediately before use, a sterilizing agent in the form of a germ-free solid composition soluble in sterilized water or one of some other media which can be sterilized and injected.

Exemplary solid preparations for oral administration include capsules, tablets, pills, powders, granules, etc. Upon formulation of these solid preparations, the compounds according to the present invention are generally mixed with at least one inert extender such as sucrose, lactose or starch. One or more materials other than inert extenders, for example, a lubricant such as magnesium stearate can also be incorporated in the preparations upon formulation of the latter in a usual manner. A buffer can also be incorporated in the case of capsules, tablets and pills. Tablets and pills can be applied with an enteric coating.

Illustrative liquid preparations for oral administration include pharmaceutically-acceptable emulsions, solutions, suspensions, syrups and elixirs, which contain an inert diluent employed commonly by those skilled in the art, for example, water. In addition to such an inert diluent, the liquid preparations can also be added with one or more auxiliary agents, for example, wetting agents, emulsifiers, suspending agents, sweetening agents, seasoning agents and perfumes. Preparations for rectal administration are preferred to contain an excipient such as cacao butter or suppository wax in addition to a compound according to the present invention.

The dosage of the compounds (I) according to the present invention depends on the properties of the compound to be administered, the administration route, the desired treatment term and other factors. It generally ranges from about 0.1 mg/kg to 100 mg/kg per day, with about 0.5–50 mg/kg per day being preferred especially. If desired, this daily dosage can be administered in 2–4 portions.

EXAMPLES

The present invention will now be explained in detail with reference to Examples and Reference Examples, but the present invention is not limited to these Examples.

Reference Example 1

2-Acetylamino-5-methyl-1,3,4-thiadiazole:

To a mixture of toluene (20 ml) and triethylamine(2.63 g) was added 2-amino-5- methyl-1,3,4-thiadiazole (3.0 g) and acetic anhydride (3.2 g). The mixture was heated under reflux for 2.5 hours. After cooling, the precipitated solid was filtrated, washed with water and dried. The title compound (3.65 g) was obtained.

Reference Example 2

2-Butyrylamino-5-ethyl-1,3,4 -thiadiazole:

2-Amino-5-ethyl-1,3,4-thiadiazole (0.5 g) was added to a mixture of toluene (5 ml) and triethylamine (0.4 g). With stirring, butyryl chloride (0.5 g) was added to the suspension at room temperature. After stirring for 2 hours, aqueous sodium bicarbonate solution and ethyl acetate were added to the reaction mixture. The organic layer was separated and washed with water several times. The precipitated crystals and the organic layer were combined and the solvent was concentrated to 5 ml. The precipitated crystals were filtrated and dried. The title compound (0.62 g) was obtained.

Several azole derivatives shown formula (2) were synthesized in a similar manner as above. Synthetic methods of thiadiazoline derivatives and thiadiazole derivatives (groupA/A-9,A-10) by preferable Preparation Process 1 in the present invention were described as below (example1–example 15).

Example 1

Using a sodium hydride as a base in Preparation Process-1, the compounds shown below were synthesized.

(1) 2-Butyrylimino-5-ethyl-3-[2'-(1H-tetrazol-5-yl)-biphenyl-4-yl]methyl-1,3,4-thiadiazoline[Compound No.1]

To a suspension of sodium hydride (60 mg, 55% in oil) in N,N-dimethylformamide (5 ml) was added 2-ethyl-5-butyrylamino-1,3,4-thiadiazole (0.26 g) at room temperature. When evolution of hydrogen ceased, a solution of 4,-bromomethyl-2-(N-triphenylmethyltetrazol-5-yl) biphenyl (0.7 g) in N,N-dimethylformamide (5 ml) was added to the reaction mixture. After stirring for 3 hours at room temperature, water and ethyl acetate were added to the mixture. The organic layer was separated, washed with water and dried over anhydrous magnesium sulfate. The magnesium sulfate was removed by filtration and the filtrate was evaporated. The residue containing two major products on thin-layer chromatography was separated by column chromatography on silica gel (eluent: chloroform).

The first eluted fractions were collected and the solvent was evaporated. To the residue were added dioxane (5 ml) and 10% hydrochloric acid solution (1 ml), and the mixture was stirred for 1 hour at room temperature. The reaction mixture was made basic with 5% aqueous sodium hydroxide solution. The aqueous layer was washed with ether, adjusted to about pH 2 with 10% hydrochloric acid solution, and extracted with ethyl acetate. The organic layer was separated, washed with water and dried over anhydrous magnesium sulfate. The magnesium sulfate was removed by filtration and the filtrate was evaporated. The resultant oil crystallized on standing. Diisopropyl ether was added, and the crystals were filtrated and dried. The title compound (No.1) was obtained as colorless crystals (100 mg).

Property colorless crystals
Melting point 164°–166° C.
$^1$H-NMR($\delta$ppm in CDCl$_3$)
8.15(1H,dd), 7.41–7.63(3H,m), 7.41(2H,d), 7.20(2H,d), 5.49(2H,s), 2.82(2H,q), 2.51(2H,t), 1.65–1.76(2H,m), 1.32 (3H,t), 0.95(3H,t)

(2) 2-[N-Butyryl-N-(2'-(1H-tetrazol-5-yl)biphenyl-4-yl) methyl]amino-5-ethyl-1,3,4 -thiadiazole [Compound No. 2]:

The residue containing two major products described in example 1 ( 1 ) was separated by column chromatography on silica gel (eluent: chloroform).

The secondly eluted fractions were collected and the solvent was evaporated. To the residue were added dioxane (5 ml) and 10% hydrochloric acid solution (1 ml), and the mixture was stirred for 1 hour at room temperature. The reaction mixture was made basic with saturated aqueous hydrogen bicarbonate solution. The aqueous layer was washed with ether, adjusted to about pH 2 with 10% hydrochloric acid solution, and extracted with ethyl acetate. The organic layer was separated, washed with water and dried over anhydrous magnesium sulfate. The magnesium sulfate was removed by filtration and the filtrate was evaporated. The resultant oil crystallized on standing. Diisopropyl ether was added, and the crystals were filtrated and dried. The title compound (No.2) was obtained as colorless crystals(30 mg).

Property colorless crystals
Melting point 162°–164° C.
$^1$H-NMR($\delta$ppm in CDCl$_3$)
8.02(1H,d), 7.12–7.61(7H,m), 5.44(2H,s), 2.95–3.09(2H, m), 2.56–2.63(2H,m), 1.70–1.81(2H,m), 1.40(3H,t), 0.99 (3H,t)

Example 2

Compounds Nos.3–36 were synthesized in a similar manner to example 1 (1) and (2).

(1) 2-Acetylimino-5-cyclopropyl-3-[2'-(1H-tetrazol-5-yl)-biphenyl -4-yl]methyl-1,3,4-thiadiazoline [Compound No. 3:

Property colorless crystals
Melting point 186°–188° C.
$^1$H-NMR($\delta$ppm in DMSO-d$_6$)
7.53–7.72 (4H,m), 7.19 (2H,d), 7.09 (2H,d), 5.44 (2H,s) 2.18 (3H,s), 2.27–2.32 (1H,m), 1.05–1.14 (2H,m) , 0.86–0.96 (2H,m)

(2) 2-[N-Acetyl-N-(2'-(1H-tetrazol-5-yl)biphenyl-4-yl)-methyl]amino-5-cyclopropyl-1,3,4-thiadiazole [Compound No.4]:

Property colorless crystals
Melting point 195°–197° C.
$^1$H-NMR($\delta$ppm in CDCl$_3$)
7.90 (1H,d), 7.06–7.60 (7H,m), 5.34 (2H,s), 2.37 (3H,s), 2.24–2.29(1H,m), 1.14–1.18 (2H,m), 1.05–1.12 (2H,m)

(3) 2-propionylimino-5-n-propyl-3[2'-(1H-tetrazol-5-yl) biphenyl-4-yl]methyl-1,3,4 -thiadiazoline [Compound No.5]:

Property colorless crystals
Melting Point 135°–138° C.
$^1$H-NMR($\delta$ppm in CDCl$_3$)
8.20(1H,d), 7.38–7.60 (3H,m), 7.44 (2H,d), 7.23(2H,d), 5.52(2H,s), 2.80 (2H,t), 2.59(2H,q), 1.76(2H,m), 1.21(3H,t), 1.00(3H,t)

(4) 2- [N-Propionyl-N- (2'- (1H-tetrazol-5-yl)biphenyl-4-yl ) methyl]amino-5-n-propyl-1,3,4-thiadiazole[Compound No.6]:

Property colorless powder
¹H-NMR(δppm in CDCl₃)
8.06(1H,d), 7.04–7.61(7H,m), 5.46(2H,s), 2.98(2H,t), 2.60–2.70 (2H,m), 1.70–1.90 (2H,m), 1.19–1.31 (3M,m), 1.01 (3H,t)

(5) 2-propionylimino-5-n-butyl-3-[2'-(1H-tetrazol-5-yl)biphenyl-4-yl]methyl-1,3,4-thiadiazoline [Compound No. 7]:
Property colorless crystals
Melting point 115°–117° C.
¹H-NMR(δppm in CDCl₃)
8.09 (1,d), 7.30–7.62(3H,m), 7.37(2H,d), 7.16(2H,d), 5.47(2H,s), 2.78(2H,t), 2.54(2H,q), 1.62–1.70(2H,m), 1.32–1.43(2H,m), 1.16(3H,t), 0.93(3H,t)

(6) 2-[N-Propionyl-N-(2'-(1H-tetrazol-5-yl)biphenyl-yl)methyl]amino-5-n-butyl-1,3,4-thiadiazole [Compound No.8]:
Property colorless powder
¹H-NMR(δppm in CDCl₃) 7.94 (1H,d), 7.06–7.58 (7H, m), 5.39(2H,s), 2.98(2H,t), 2.62 (2H,q), 1.69–1.78 (2H,m), 1.35–1.46 (2H,m), 1.21 (3H,t), 0.94 (3H, t)

(7) 2-Butyrylimino-5-methyl-3-[2'-(1H-tetrazol-5-yl)-biphenyl-4-yl]methyl-1,3,4-thiadiazoline [Compound No. 9]:
Property colorless crystals
Melting point 183°–184° C.
¹H-NMR(δppm in CDCl₃)
8.21(1H,d), 7.45 (2H,d), 7.22–7.60 (5H,m), 5.51 (2H,s) 2.54 (2H,t), 2.52 (3H,s), 1.69–1.76 (2H,m), 0.97 (3H,t)

(8) 2-[N-Butyryl-N-(2'-(1H-tetrazol-5-yl)biphenyl-4-yl)methyl]amino-5-methyl-1,3,4-thiadiazole [Compound No. 10]:
Property colorless powder
¹H-NMR (δppm in CDCl₃)
8.12(1H,d), 7.21–7.60(7H,m), 5.49(2H,s), 2.68(2H,t) 2.61(3H,s), 1.71–1.79(2H,m), 0.98(3H,t)

(9) 2-Butyrylimino-5-cyclopropyl-3-[2'-(1H-tetrazol-5-yl)biphenyl-4-yl]methyl-1,3,4-thiadiazoline [Compound No.11]:
Property colorless crystals
Melting point 163°–164° C.
¹H-NMR(δppm in CDCl₃)
8.11(1H,dd), 7.42–7.68(3H,m), 7.38(2H,d), 7.18(2H,d) 5.45(2H,s), 2.50(2H,t), 2.05–2.15(1H,m), 1.66–1.77(2H,m), 1.11–1.18(2H,m), 0.91–1.00(5H,m)

(10) 2-[N-Butyryl-N-(2'-(1H-tetrazol-5-yl)biphenyl-4-yl)methyl]amino-5-cyclopropyl-1,3,4-thiadiazole Compound No.12]:
Property colorless powder
¹H-NMR(δppm in CDCl₃)
8.09(1H,d), 7.19–7.60(7H,m), 5.44(2H,s), 2.60(2H,t), 2.23–2.36(1H,m), 1.73–1.81(2H,m), 0.85–1.28(7H,m)

(11) 2-Butyrylimino-5-n-butyl-3-[2'-(1H-tetrazol-5-yl)-biphenyl-4-yl]methyl-1,3,4-thiadiazoline [Compound No. 13]:
Property colorless crystals
Melting point 134°–135° C.
¹H-NMR(δppm in CDCl₃)
8.10(1H,dd), 7.41–7.63(3H,m), 7.38(2H,d), 7.17(2H,d), 5.48(2H,s), 2.80(2H,t), 2.49(2H,t), 1.62–1.75(4H,m), 1.35–1.43(2H,m), 0.94(3H,t), 0.93(3H,t)

(12) 2-[N-Butyryl-N-(2'-(1H-tetrazol-5-yl)biphenyl-4-yl)-methyl]amino-5-n-butyl-1,3,4-thiadiazole [Compound No. 14]:
Property colorless powder
¹H-NMR(δppm in CDCl₃)
8.04(1H,d), 7.10–7.85(7H,m), 5.45(2H,s), 2.92–3.02(2H, m), 2.56–2.62(2H,m), 1.72–1.80(4H,m), 1.38–1.43 (2H,m), 0.89–0.97 (6H,m)

(13) 2-Butyrylimino-5-tert-butyl-3-[2'-(1H-tetrazol-5-yl)-biphenyl-4-yl]methyl-1,3,4-thiadiazoline [Compound No. 15]:
Property colorless powder
¹H-NMR(δppm in CDCl₃)
8.00(1H,d), 7.12–7.58(7H,m), 5.47(2H,s), 2.47(2H,t), 1.64–1.72(2H,m), 1.41(9H,s), 0.93(3H,t)

(14) 2-[N-Butyryl-N-(2'-(1H-tetrazol-5-yl)biphenyl-4-yl)-methyl]amino-5-tert-butyl-1,3,4-thiadiazole [Compound No. 16]:
Property colorless powder
¹H-NMR(δppm in DMSO-d₆)
7.92(1H,d), 7.12–7.56(7H,m), 5.42(2H,s), 2.45(2H,t) 1.62–1.67(2H,m), 1.48(9H,s), 0.86(3H,t), 0.98(3H,t)

(15) 2-Cyclopropylcarbonylimino-5-methyl-3-[2'-(1H-tetrazol-5-yl)biphenyl-4-yl]methyl-1,3,4-thiadiazoline [Compound No. 17]:
Property colorless crystals
Melting point 221°–223° C.
¹H-NMR(δppm in CDCl₃)
8.16(1H,d), 7.40–7.60(3H,m), 7.41(2H,d), 7.24(2H,d) 5.48(2H,s), 2.50(3H,s), 1.84–1.98(1H,m), 1.08–1.10 (2H, m), 0.90–0.92 (2H,m)

(16) 2-[N-Cyclopropylcarbonyl-N-(2'-(1H-tetrazol-5-yl)-biphenyl-4-yl)methyl]amino-5-methyl-1,3,4-thiadiazole [Compound No. 18]:
Property colorless powder
¹H-NMR(δppm in CDCl₃)
8.09(1H,d), 7.47–7.67(3H,m), 7.41(2H,d), 7.20(2H,d) 5.66(2H,s), 2.66(3H,s), 1.88–1.98(1H,m), 1.19–1.28(2H,m), 1.01–1.09(2H,m)

(17) 2-Cyclopropylcarbonylimino-5-ethyl-3-[2'-(1H-tetrazol-5-yl)biphenyl-4-yl]methyl-1,3,4-thiadiazoline [Compound No. 19]:
Property colorless crystals
Melting point 199°–200° C.
¹H-NMR(δppm in CDCl₃)
8.18(1H,dd), 7.42–7.62(3H,m), 7.43(2H,d), 7.23(2H,d), 5.49(2H,s), 2.84(2H,q), 1.88–1.93(1H,m), 1.32(3H,t), 1.08–1.10 (2H,m), 0.88–0.94 (2H,m)

(18) 2-[N-Cyclopropylcarbonyl-N-(2'-(1H-tetrazol-5-yl)-biphenyl-4-yl)methyl]amino-5-ethyl-1,3,4-thiadiazole [Compound No.20]:
Property colorless crystals
Melting point 198°–199° C.
¹H-NMR(δppm in CDCl₃)
8.06(1H,d), 7.08–7.60(7H,m), 5.64(2H,s), 3.02(2H,q), 1.96(1H,m), 1.39(3H,t), 1.22–1.26(2H,m), 1.02–1.04 (2H, m)

(19) 2-Cyclopropylcarbonylimino-5-n-propyl-3-[2'-(1H-tetrazol-5-yl)biphenyl-4-yl]methyl-1,3,4-thiadiazoline [Compound No.21]:
Property colorless crystals
Melting point 135°–137° C.
¹H-NMR(δppm in CDCl₃)
8.10(1H,d), 7.42–7.58(3H,m), 7.38(2H,d), 5.47(2H,s), 2.76(2H,t), 1.87–1.91(1H,m), 1.68–1.88(2H, m), 1.00–1.06(2H,m), 0.98(3H,t), 0.88–0.95 (2H,m)

(20) 2-[N-Cyclopropylcarbonyl-N-(2'-(1H-tetrazol-5-yl)-biphenyl-4-yl)methyl]amino-5-n-propyl-1,3,4-thiadiazole [Compound No. 22]:
Property colorless crystals
Melting point 171°–172 ° C.
¹H-NMR(δppm in CDCl₃)
8.05(1H,d), 7.15–7.63(7H,m), 5.62(2H,s), 2.96(2H,t), 1.92–1.98(1H,m), 1.75–1.85(2H,m), 1.22–1.27 (2H,m), 0.95–1.04 (5H,m)

(21) 2-Cyclopropylcarbonylimino-5-cyclopropyl-3-[2'-1H-tetrazol-5-yl) biphenyl-4-yl]methyl-1,3,4-thiadiazoline [Compound No. 23]:

Property colorless crystals
Melting point 201°–202° C.
$^1$H-NMR($\delta$ppm in CDCl$_3$)
8.18(1H,dd), 7.42–7.64(3H,m), 7.41(2H,d), 7.23(2H,d), 5.46(2H,s), 2.08–2.17(1H,m),1.87–1.94(1H,m), 0.86–1.94 (8H,m)

(22) 2-[N-Cyclopropylcarbonyl-N-(2'-(1H-tetrazol-5-yl)-biphenyl-4-yl)methyl]amino-5-cyclopropyl-1,3,4-thiadiazole [Compound No. 24]:

Property colorless crystals
Melting point 201°–203° C.
$^1$H-NMR($\delta$ppm in CDCl$_3$)
7.98(1H,d), 7.06–7.62(7H,m), 5.52(2H,s), 2.21–2.29(1H, m), 1.88–1.96(1H,m), 0.97–1.21(8H,m)

(23) 2-Cyclopropylcarbonylimino-5-n-butyl-3-[2'-(1H-tetrazol-5-yl)biphenyl-4-yl]methyl-1,3,4-thiadiazoline [Compound No. 25 ]:

Property colorless crystals
Melting point 139° C.
$^1$H-NMR($\delta$ppm in CDCl$_3$)
8.17(1H,d), 7.42–7.61(3H,m), 7.41(2H,d), 7.21(2H,d), 5.48(2H,s), 2.80(2H,t), 1.87–1.93(1H,m), 1.68–1.74 (2H, m), 1.33–1.42 (2H,m), 1.02–1.11 (2H,m), 0.75–0.96 (5H ,m)

(24) 2-[N-Cyclopropylcarbonyl-N-(2'-(1H-tetrazol-5-yl)-biphenyl-4-yl) methyl]amino-5-n-butyl-1,3,4-thiadiazole [Compound No. 26]:

Property colorless powder
$^1$H-NMR($\delta$ppm in CDCl$_3$)
8.10(III,d), 7.16–7.62(7H,m), 5.66(2H,s), 2.95–3.02 (2H, m), 0.97–2.00 (12H,m)

(25) 2-Cyclopropylcarbonylimino-5-phenyl-3-[2'-(1H-tetrazol-5-yl)biphenyl-4-yl]methyl-1,3,4-thiadiazoline [Compound No. 27]:

Property colorless powder
$^1$H-NMR($\delta$ppm in CDCl$_3$)
8.04–8.13(1H,m), 7.72–7.80(2H,m), 7.15–7.59(10H,m), 5.58(2H,s), 1.90–1.97 (1H,m), 1.05–1.13(2H,m), 0.88–0.98 (2H,m)

(26) 2-[N-Cyclopropylcarbonyl-N-(2'-(1H-tetrazol-5-yl)-biphenyl-4-yl) methyl]amino-5-phenyl-1,3,4-thiadiazole [Compound No. 28]:

Property colorless powder
$^1$H-NMR($\delta$ppm in CDCl$_3$)
7.78–7.90(4H,m), 7.33–7.60(5H,m), 7.16(2H,d), 7.06 (2H,d), 5.59(2H,s), 1.91–2.02(1H,m), 1.18–1.29(2H,m), 0.97–1.05 (2H,m)

(27) 2-Valerylimino-5-methyl-3-[2'-(1H-tetrazol-5-yl)-biphenyl-4-yl]methyl-1,3,4-thiadiazoline [Compound No. 29]:

Property colorless crystals
Melting point 156°–157° C.
$^1$H-NMR($\delta$ppm in CDCl$_3$) 8.14(1H,dd), 7.39(2H,d), 7.16 (2H,d), 7.41–7.65 (3H,m), 5.47(2H,s), 2.51(2H,t), 2.50(3H, s), 1.32–1.40(2H,m), 0.91(3H,t)

(28) 2-[N-Valeryl-N-(2'-(1H-tetrazol-5-yl)biphenyl-4-yl) methyl]amino-5-methyl-1,3,4-thiadiazole [Compound No.30]:

Property colorless crystals
Melting point 163°–164° C.
$^1$H-NMR($\delta$ppm in CDCl$_3$) 8.05(1H,d), 7.16–7.59(7H,m), 5.45(2H,s), 2.66(3H,s), 2.62(2H,t), 1.69–1.70(2H,m), 1.35 (2H,m), 0.91(3H,t)

(29) 2-Valerylimino-5-ethyl-3-[2'-(1H-tetrazol-5-yl)-biphenyl-4-yl]methyl-1,3,4-thiadiazoline [Compound No. 31]:

Property colorless crystals
Melting point 136°–139° C.
$^1$H-NMR($\delta$ppm in CDCl$_3$) 8.10(1H,d), 7.40(2H,d), 7.18 (2H,d), 7.41–7.57 (3H,m), 5.48 (2H,s), 2.84 (2H,q), 2.53 (2H,t), 1.62–1.74(2H,m), 1.28–1.41(2H,m), 1.32(3H,t), 0.91 (3H,t)

(30) 2-[N-Valeryl-N-(2'-(1H-tetrazol-5-yl)biphenyl-4-yl)-methyl]amino-5-ethyl-1,3,4-thiadiazole [Compound No. 32]:

Property colorless crystals
Melting point 175°–177° C.
$^1$H-NMR($\delta$ppm in CDCl$_3$)
8.06(1H,d), 7.17–7.59(5H,m), 7.41(2H,d), 5.45(2H,s), 3.03(2H,q), 2.63(2H,t), 1.63–1.79(2H,m), 1.31–1.43(5H,m), 0.91(3H,t)

(31) 2-Valerylimino-5-cyclopropyl-3-[2'-(1H-tetrazol-5-yl) biphenyl-4-yl]methyl-1,3,4-thiadiazoline [Compound No.33]:

Property colorless crystals
Melting point 164°–167° C.
$^1$H-NMR($\delta$ppm in CDCl$_3$)
8.18(1H,d), 7.21–7.64(7H,m), 5.49(2H,s), 2.52(2H,t), 2.09–2.18(1H,m), 1.60–1.84(4H,m), 0.86–1.52(7H,m)

(32) 2-[N-Valeryl-N-(2'-(1H-tetrazol-5-yl)biphenyl-4-yl) methyl]amino-5-cyclopropyl-1,3,4-thiadiazole [Compound No.34]:

Property colorless crystals
Melting point 197° C.
$^1$H-NMR($\delta$ppm in CDCl$_3$)
8.02(1H,d), 7.12–7.58(7H,m), 5.40(2H,s), 3.65(2H,t), 2.57–2.68(2H,m), 2.21–2.32(1H,m), 1.63–1.78(2H,m), 1.30–1.42(2H,m), 1.09(2H,m), 0.90(3H,t)

(33) 2-Cyclobutylcarbonylimino-5-ethyl-3-[2'-(1H-tetrazol-5-yl) biphenyl-4-yl]methyl-1,3,4 -thiadiazoline [Compound No. 35 ]:

Property colorless crystals
Melting point 181°–183° C.
$^1$H-NMR($\delta$ppm in DMSO-d$_6$)
7.56–7.75(4H,m), 7.21–7.26(2H,m), 7.10–7.12(2H,m), 5.46(2H,s), 3.40(1H,m), 2.83–2.92(2H,m), 2.06–2.28(4H, m), 1.88–2.00(2H,m), 1.27–1.30(3H,m)

(34) 2-[N-Cyclobutylcarbonyl-N-(2'-(1M-tetrazol-5-yl)-biphenyl-4-yl)methyl]amino-5-ethyl-1,3,4-thiadiazole [Compound No. 36]:

Property colorless powder
$^1$H-NMR($\delta$ppm in DMSO-d$_6$)
7.52–7.67(4H,m), 7.05–7.13(4H,m), 5.38(2H,s), 3.57 (1H,m), 2.99(2H,q), 1.75–2.29(6H,m), 1.30(3H,t)

Example 3

2-propionylimino-5-ethyl-3-[2'-(1H-tetrazol-5-yl) -biphenyl-4-yl]methyl-1,3,4 -thiadiazoline [Compound No. 37]:

Title compound No.37 was synthesized as a single product in a similar manner to example 1 (1).

Property colorless crystals
Melting point 186°–187° C.
$^1$H-NMR($\delta$ppm in CDCl$_3$) 8.08(1H,d), 7.41–7.62 (3H,m), 7.36(2H,d), 7.16(2H,d), 5.47(2H,s), 2.82(2H,q), 2.53(2H,q), 1.31(3H,t), 1.15 (3H, t)

Example 4

Compounds Nos. 38–100 were synthesized in a similar manner to example 3.

(1) 2-Acetylimino-5-n-propyl-3-[2'-(1H-tetrazol-5-yl)-biphenyl-4-yl]methyl-1,3,4-thiadiazoline [Compound No. 38]:

Property colorless powder
¹H-NMR(δppm in CDCl₃)
7.95(1H,d), 7.42–7.61(3H,m), 7.28(2H,d), 7.12(2H,d), 5.44(2H,s), 2.77(2H,t), 2.19(3H,s), 1.68–1.77(2H,m), 0.98 (3H,t)

(2) 2-Acetylimino-5-n-butyl-3-[2'-(1H-tetrazol-5-yl)-biphenyl-4-yl]methyl-1,3,4-thiadiazoline[Compound No.39]:
Property colorless powder
¹H-NMR(δppm in CDCl₃)
7.95(1H,d), 7.42–7.61(3H,m), 7.40(2H,d), 7.12(2H,d), 5.49(2H,s), 2.81(2H,t), 2.25(3H,s), 1.67–1.73(2H,m), 1.35–1.43 (2H,m), 0.94 (3H,t)

(3) 2-Butyrylimino-5-n-propyl-3-[2'-(1H-tetrazol-5-yl)-biphenyl-4-yl]methyl-1,3,4-thiadiazoline [Compound No. 40]:
Property colorless powder
¹H-NMR(δppm in CDCl₃)
8.19(1H,dd), 7.42–7.63(3H,m), 7.43(2H,d), 7.22(2H,d) 5.51(2H,s), 2.79(2H,t), 2.53(2H,t), 1.65–1.79(4H,m) 1.00 (3H,t), 0.96(3H,t)

(4) 2-Butyrylimino-5-hydroxymethyl-3-[2'-(1H-tetrazol-5-yl ) biphenyl-4-yl]methyl-1,3,4-thiadiazoline [Compound No.41]:
Property colorless powder
¹H-NMR(δppm in CDCl₃)
7.98(1H,d), 7.53–7.59(2H,m), 7.39(1H,d), 7.31(2H,d) 7.06(2H,d), 5.44(2H,s), 4.79(2H,s), 2.52(2H,t), 1.67–1.76 (2H,m), 0.94 (3H,t)

(5) 2-Acetylimino-5-bromo-3-[2'- (1H-tetrazol-5-yl) biphenyl-4-yl]methyl-1,3,4-thiadiazoline [Compound No.42]:
Property colorless powder
¹H-NMR(δppm in CDCl₃)
8.21–8.24(1H,m), 7.28–7.60(7H,m), 5.51(2H,s), 1.94–1.97(1H,m), 1.13–1.15(2H,m), 0.97–1.00(2H,m)

(6) 2-Cyclopropylcarbonylimino-5-hydroxymethyl-3-[2'-(1H-tetrazol-5-yl)biphenyl-4-yl]methyl-1,3,4-thiadiazoline [Compound No.43]:
Property colorless crystals
Melting point 215°–217° C.
¹H-NMR(δppm in DMSO-d₆)
7.52–7.70(4H,d), 7.24(2H,d), 7.10(2H,d), 6.03(1H,brs), 5.46(2H,s), 4.62(2H,s), 1.81–1.83(1H,m), 1.10–1.18(2H,m), 0.86–0.93 (2H,m)

(7) 2-Valerylimino-5-n-propyl-3-[2'-(1H-tetrazol-5-yl)-biphenyl-4-yl]methyl-1,3,4-thiadiazoline [Compound No. 44]:
Property colorless crystals
Melting point 153°–156° C.
¹H-NMR(δppm in CDCl₃)
8.23 (1H,d), 7.26–7.61 (7H,m), 5.52(2H,s), 2.80(2H,t), 2.57 (2H,t),1.65–1.79(4H,m), 1.32–1.43 (2H,m), 1.00 (3H,t), 0.93(3H,t)

(8) 2-Valerylimino-5-n-butyl-3-[2'-(1H-tetrazol-5-yl)-biphenyl-4-yl]methyl-1,3,4-thiadiazoline [Compound No. 45]:
Property colorless powder
¹H-NMR(δppm in CDCl₃)
8.14(1H,d), 7.40(2H,d), 7.19(2H,d), 7.41–7.58(3H,m), 5.49(2H,s), 2.78(2H,t), 2.53 (2H, t), 1.62–1.77 (4H,m), 1.32–1.38(4H,m), 0.91(6H,m)

(9) 2-Valerylimino-5-ethylthio-3-[2'-(1H-tetrazol-5-yl)-biphenyl-4-yl]methyl-1,3,4-thiadiazoline [Compound No. 46]:
Property colorless powder
¹H-NMR(δppm in CDCl₃)
8.10(1H,d), 7.45–7.62 (3H,m), 7.41(2H,d), 7.18(2H,d), 5.48 (2H,s), 3.10–3.18 (2H,m), 2.54 (2H,t), 1.65–1.70 (2H, m), 1.31–1.43 (5H,m), 0.91 (3H,t)

(10) 2 -Pivaloylimino-5-ethyl-3- [2'-(1H-tetrazol-5-yl)-biphenyl-4-yl]methyl-1,3,4-thiadiazoline [Compound No. 47]:
Property colorless crystals
Melting point 180°–181° C.
¹H-NMR(δppm in CDCl₃)
8.12(1H,dd), 7.41–7.59(3H,m), 7.48(2H,d), 7.20(2H,d), 5.49(2H,s), 2.83(2H,q), 1.32(3H,t), 1.25(9H,s)

(11) 2-Crotonoylimino-5-ethyl-3-[2'- (1H-tetrazol-5-yl)-biphenyl-4-yl]methyl-1,3,4-thiadiazoline [Compound No. 48]:
Property colorless crystals
Melting point 183°–184° C.
¹H-NMR(δppm in CDCl₃)
8.16(1H,dd), 7.42–7.68(3H,m), 7.43 (2H, d), 7.20 (2H, d), 7.08–7.16(1H,m), 6.20(1H,dd), 5.52(2H,s),2.85(2H,q), 1.93 (3H,d), 1.33(3H,t)

(12) 2-Crotonoylimino-5-cyclopropyl-3-[2'-(1H-tetrazol-5-yl)biphenyl-4-yl]methyl-1,3,4-thiadiazoline [Compound NO. 49]:
Property colorless crystals
Melting point 184°–185° C.
¹H-NMR(δppm in CDCl₃)
8.16(1H,dd), 7.41–7.68(3H,m), 7.41(2H,d), 7.19(2H,d), 7.05–7.14 (1H,m), 6.18(1H,dd), 5.49(2H,s), 2.11–2.16(1H, m), 1.92(3H,dd), 1.11–1.15(2H,m), 0.97–1.00 (2H,m)

(13) 2-Trifluoroacetylimino-5-ethyl-3-[2'-(1H-tetrazol-5-yl) biphenyl-4-yl]methyl-1,3,4-thiadiazoline [Compound No.50]:
Title compound No.50 was purified by silica-gel chromatography after the acid treatment, because it was unstable in an alkaline solution.
Property colorless powder
¹H-NMR(δppm in CDCl₃)
8.15(1H,d), 7.20–7.70(7H,m), 5.56(2H,s), 2.98(2H,q), 1.40 (3H,t)

(14) 2-Methoxyacetylimino-5-ethyl-3-[2'-(1H-tetrazol-5-yl)biphenyl-4-yl]methyl-1,3,4-thiadiazoline [Compound No.51]:
Property colorless crystals
Melting point 149°–150 ° C.
¹H-NMR(δppm in CDCl₃)
8.05(1H,d), 7.03–7.81(7H,m), 5.46(2H,s), 4.21(2H,s), 3.42(3H,s), 2.85(2H,q), 1.33(3H,t)

(15) 2-Ethoxyacetylimino-5-ethyl-3-[2'-(1H-tetrazol-5-yl) biphenyl-4-yl]methyl-1,3,4-thiadiazoline [Compound No.52]:
Property colorless crystals
Melting point 195°–198° C.
¹H-NMR(δppm in CDCl₃)
8.04(1H,d), 7.52–7.60(2H,m), 7.38–7.40(1H,m), 7.28 (2H,d), 7.12(2H,d), 5.45(2H,s), 4.25(2H,s), 3.61(2H,q), 2.85 (2H,q), 1.33(3H,t), 1.22(3H,t)

(16) 2-(3-Cyclohexylpropionyl)imino-5-ethyl-3-[2'-(1H-tetrazol-5-yl)biphenyl-4-yl]methyl-1,3,4-thiadiazoline [Compound No. 53]:
Property colorless crystals
Melting point 155°–158° C.
¹H-NMR(δppm in CDCl₃)
8.17(1H,d), 7.55–7.62(2H,m), 7.45–7.48(1H,m), 7.42 (2H,d), 7.22(2H,d), 5.49(2H,s), 2.84(2H,q), 2.54(2H,t), 1.32 (3H,t), 0.82–1.75(13H,m)

(17) 2-Cyclopentylcarbonylimino-5-ethyl-3-[2'-(1H-tetrazol-5-yl)biphenyl-4-yl]methyl-1,3,4-thiadiazoline [Compound No.54]:

Property colorless crystals
Melting point 178°–179° C.
$^1$H-NMR($\delta$ppm in CDCl$_3$)
8.15(1H,d) 7.50–7.62 (2H,m), 7.40–7.46(1H,m), 7.45 (2H,d), 7.22(2H,d), 5.49(2H,s), 2.94(1H,m), 2.82(2H,t), 1.52–1.92 (8H,m), 1.32(3H,t)

(18) 2-Cyclohexylcarbonylimino-5-ethyl-3-[2'-(1H-tetrazol-5-yl)biphenyl-4-yl]methyl-1,3,4-thiadiazoline [Compound No. 55]:
Property colorless crystals
Melting point 169°–170 ° C.
$^1$H-NMR($\delta$ppm in CDCl$_3$)
8.21(1H,d), 7.21–7.62(7H,m), 5.52(2H,s), 2.84(2H,q), 2.45–2.49(1H,m), 1.30–2.02(10H,m), 1.33(3H,t)

(19) 2-(3-phenylpropionyl)imino-5-ethyl-3-[2'-(1H-tetrazol-5-yl)biphenyl-4-yl]methyl-1,3,4-thiadiazoline [Compound No. 56]:
Property colorless powder
$^1$H-NMR($\delta$ppm in DMSO-d$_6$)
7.52–7.71(4H,m), 7.06–7.23(9H,m), 5.47(2H,s), 2.94 (2H,q), 2.76–2.90(4H,m), 1.23(3H,t)

(20) 2-(4-phenylbutyryl)imino-5-ethyl-3-[2'-(1H-tetrazol-5-yl)biphenyl-4-yl]methyl-1,3,4-thiadiazoline [Compound No. 57]:
Property colorless powder
$^1$H-NMR($\delta$ppm in CDCl$_3$)
8.03(1H,d), 7.12–7.58(12H,m), 5.42(2H,s), 2.82(2H,q), 2.65(2H,t), 2.51–2.57(2H,m), 2.00(2H,t), 1.31(3H,t)

(21) 2-Cinnamoylimino-5-ethyl-3-[2'-(1H-tetrazol-5-yl)biphenyl-4-yl]methyl-1,3,4-thiadiazoline [Compound No.58]:
Property colorless powder
$^1$H-NMR($\delta$ppm in DMSO-d$_6$)
7.40–7.76(10H,m), 7.30(2H,d), 7.11(2H,d), 6.88(1H,d), 5.59(2H,s), 2.90(2H,q), 1.26(3H,t)

(22) 2-(4-Morpholinocarbonyl)imino-5-ethyl-3-[2'-(1H-tetrazol-5-yl)biphenyl-4-yl]methyl-1,3,4-thiadiazoline [Compound No. 59]:
Property colorless crystals
Melting point 200°–203° C.
$^1$H-NMR($\delta$ppm in CDCl$_3$)
8.19(1H,d), 7.21–7.59(7H,m), 40(2H,s), 3.62–3.82(8H, m), 2.81(2H,q), 1.31(3H,t)

(23) 2-Benzoylimino-5-ethyl-3-[2'-(1H-tetrazol-5-yl)-biphenyl-4-yl]methyl-1,3,4-thiadiazoline [Compound No. 60]:
Property colorless crystals
Melting point 215°–216° C.
$^1$H-NMR($\delta$ppm in CDCl$_3$)
8.31–8.33(2H,m), 8.13(1H,d), 7.20–7.56(10H,m), 5.62 (2H,s), 2.89(2H,q), 1.36(3H,t)

(24) 2-(2-Methoxybenzoyl)imino-5-ethyl-3-[2'-(1H-tetrazol-5-yl)biphenyl-4-yl]methyl-1,3,4-thiadiazoline [Compound No.61]:
Property colorless powder
$^1$H-NMR($\delta$ppm in DMSO-d$_6$)
7.47–7.82(7H,m), 7.31 (2H,d), 7.13 (2H,d), 7.00–7.09 (1H,m), 5.53(2H,s), 3.78(3H,s), 2.91(2H,q), 1.27 (3H, t)

(25) 2-(3-Methoxybenzoyl)imino-5-ethyl-3-[2'-(1H-tetrazol-5-yl) biphenyl-4-yl]methyl-1,3,4-thiadiazoline [Compound No. 62]:
Property colorless powder
$^1$H-NMR($\delta$ppm in DMSO-d$_6$)
7.17–7.87(8H,m), 7.35(2H,d), 7.15(2H,d), 5.64 (2H, s), 3.82(3H,s), 2.93(2H,q), 1.28(3H,t)

(26) 2-(4-Methoxybenzoyl)imino-5-ethyl-3-[2'-(1H-tetrazol-5-yl)biphenyl-4-yl]methyl-1,3,4-thiadiazoline [Compound No. 63]:
Property colorless powder
$^1$H-NMR($\delta$ppm in DMSO-d$_6$)
8.20(2H,d), 7.50–7.66(3H,m), 7.29–7.34(3H,m), 7.10 (2H,d), 7.04(2H,d), 5.62(2H,s), 3.83(3H,s), 2.91(2H,q), 1.27 (3H,t)

(27) 2-(2-Fluorobenzoyl)imino-5-ethyl-3-[2'-(1H-tetrazol-5-yl)biphenyl-4-yl]methyl-1,3,4-thiadiazoline [Compound No. 64]:
Property colorless powder
$^1$H-NMR($\delta$ppm in CDCl$_3$)
8.10–8.16(2H,m), 7.12–7.55(10H,m), 5.58(2H,s), 2.89 (2H,q), 1.36(3H,t)

(28) 2- (3-Fluorobenzoyl)imino-5-ethyl-3-[2'-(1H-tetrazol-5-yl)biphenyl-4-yl]methyl-1,3,4-thiadiazoline [Compound No. 65]:
Property colorless powder
$^1$H-NMR($\delta$ppm in CDCl$_3$)
7.96–8.38(3H,m), 7.26–7.60(9H,m), 5.63(2H,s), 2.90 (2H, q), 1.37 (3H, t)

(29) 2-(4-Fluorobenzoyl)imino-5-ethyl-3-[2'-(1H-tetrazol-5-yl)biphenyl-4-yl]methyl-1,3,4-thiadiazoline Compound No. 66]:
Property colorless crystals
Melting point 165°–166° C.
$^1$H-NMR($\delta$ppm in CDCl$_3$)
8.20–8.38(2H,m), 6.85–7.60(10H,m), 5.58(2H,s), 2.87 (2H,q), 1.35(3H,t)

(30) 2-(3-Cyanobenzoyl)imino-5-ethyl-3-[2'-(1H-tetrazol-5-yl) biphenyl-4-yl]methyl-1,3,4-thiadiazoline [Compound No. 67]:
Property colorless crystals
Melting point 199°–200° C.
$^1$H-NMR($\delta$ppm in DMSO-d$_6$)
8.62(1H,s), 8.52(1H,d), 8.06(1H,d), 7.52–7.77 (5H,m), 7.35(2H,d), 7.11(2H,d), 5.71(2H,s), 2.95 (2H,q), 1.28 (3H,t)

(31) 2-(2-Chlorobenzoyl)imino-5-ethyl-3-[2'-(1H-tetrazol-5-yl)biphenyl-4-yl]methyl-1,3,4-thiadiazoline [Compound No.68]:
Property colorless powder
$^1$H-NMR($\delta$ppm in CDCl$_3$)
8.17(1H,d), 8.03(1H,d), 7.20–7.65(10H,m), 5.61(2H.,s), 2.92(2H,q), 1.38(3H,t)

(32) 2-(3-Chlorobenzoyl)imino-5-ethyl-3-[2'-(1H-tetrazol-5-yl)biphenyl-4-yl]methyl-1,3,4 -thiadiazoline [Compound No. 69]:
Property colorless powder
$^1$H-NMR($\delta$ppm in CDCl$_3$)
8.29(1H,d), 8.17–8.29(2H,m), 7.27–7.64(9H,m), 5.42 (2H,s), 2.92(2H,q), 1.38(3H,t)

(33) 2-(4-Chlorobenzoyl)imino-5-ethyl-3-[2'-(1H-tetrazol-5-yl)biphenyl-4-yl]methyl-1,3,4-thiadiazoline [Compound No. 70]:
Property colorless powder
$^1$H-NMR($\delta$ppm in CDCl$_3$)
8.24(2H,dd), 8.11(1H,dd), 7.20–7.62(9H,m), 5.63(2H,s), 2.91(2H,q), 1.38(3H,t)

(34) 2-(2-Chlorobenzoyl)imino-5-methyl-3-[2'-(1H-tetrazol-5-yl)biphenyl-4-yl]methyl-1,3,4-thiadiazoline [Compound No. 71]:
Property colorless powder
$^1$H-NMR ($\delta$ppm in DMSO-d$_6$)
7.95(1H,d), 7.44–7.68 (7H,m), 7.30 (2H,d), 5.57 (2H,s), 2.58 (3H,s)

(35) 2-(2-Chlorobenzoyl)imino-5-n-propyl-3-[2'-(1H-tetrazol-5-yl)biphenyl-4-yl]methyl-1,3,4-thiadiazoline [Compound No. 72]:

Property colorless powder
¹H-NMR(δppm in CDCl₃)
7.93 (1H, d), 7.31(2H,d), 7.43–7.67 (5H,m), 7.28 (2H,d), 7.10(2H,d), 5.58(2H,s), 2.90(2H,t), 1.68–1.76(2H,m), 0.95 (3H, t)

(36) 2-(2-Chlorobenzoyl)imino-5-n-butyl-3-[2'-(1H-tetrazol-5-yl)biphenyl-4-yl]methyl-1,3,4-thiadiazoline [Compound No. 73]:
Property colorless powder
¹H-NMR(δppm in CDCl₃)
8.18(1H,d), 8.04(1H,d), 7.23–7.60(10H,m), 5.62(2H,s), 2.92 (2H, t), 1.65–1.80(2H,m), 1.36–1.42(2H,m), 0.94 (3H, t)

(37) 2-(2-Chlorobenzoyl)imino-5-cyclopropyl-3-[2'-(1H-tetrazol-5-yl)biphenyl-4-yl]methyl-1,3,4-thiadiazoline [Compound No.74]:
Property colorless powder
¹H-NMR(δppm in CDCl₃)
8.13(1H,d), 8.02(1H,d), 7.21–7.60(10H,m), 5.57(2H,s), 2.04–2.20 (1H,m), 1.06–1.26(4H,m)

(38) 2-(2-Chlorobenzoyl)imino-5-chloro-3-[2'-(1H-tetrazol-5-yl)biphenyl-4-yl]methyl-1,3,4-thiadiazoline [Compound No. 75]:
Property colorless crystals
Melting point 180°–182° C.
¹H-NMR(δppm in CDCl₃)
8.09–8.22 (1H,m), 7.28–7.59 (11H,m), 5.64 (2H,s)

(39) 2-(2-Iodobenzoyl)imino-5-ethyl-3-[2'- (1H-tetrazol-5-yl)biphenyl-4-yl]methyl-1,3,4-thiadiazoline [Compound No. 76]:
Property colorless powder
¹H-NMR(δppm in CDCl₃)
7.06–7.98(12H,m), 5.58(2H,s), 2.89(2H,q), 1.36(3H,t)

(40) 2- (2 -Trifluoromethylbenzoyl)imino-5-ethyl-3-[2'-(1H-tetrazol-5-yl)biphenyl-4-yl]methyl-1,3,4-thiadiazoline [Compound No. 77]:
Property colorless powder
¹H-NMR (δppm in CDCl₃)
7.18–8.04(10H,m), 6.86–6.89(2H,m), 5.54(2H,s), 2.89 (2H,q), 1.36(3H,t)

(41) 2-(3-Trifluoromethylbenzoyl)imino-5-ethyl-3-[2'-(1H-tetrazol-5-yl) biphenyl-4-yl]methyl-1,3,4-thiadiazoline [Compound No. 78]:
Property colorless crystals
Melting point 193°–196° C.
¹H-NMR(δppm in DMSO-d₆)
8.53(1H,d), 8.32(1H,s), 7.51–7.97(6H,m), 7.36(2H,d), 7.11(2H,d), 5.67(2H,s), 2.95(2H,q), 1.29(3H,t)

(42) 2-(4-Trifluoromethylbenzoyl)imino-5-ethyl-3-[2'-(1H-tetrazol-5-yl)biphenyl-4-yl]methyl-1,3,4-thiadiazoline [Compound No. 79]:
Property colorless powder
¹H-NMR(δppm in DMSO-d₆)
8.43(2H,d), 7.88(2H,d), 7.49–7.90(4H,m), 7.34(2H,d), 7.11(2H,d), 5.67(2H,s), 2.95(2H,q), 1.29(3H,t)

(43) 2- (2-Trifluoromethylbenzoyl)imino-5-methyl-3-[2'-(1H-tetrazol-5-yl)biphenyl-4-yl]methyl-1,3,4-thiadiazoline [Compound No. 80]:
Property colorless powder
¹H-NMR(δppm in CDCl₃)
8.07(1H,d), 7.87(1H,d), 7.74(1H,d), 7.46–7.76(5H,m), 7.45(2H,d), 7.19(2H,d), 5.55(2H,s), 2.56(3H,s)

(44) 2-(2-Trifluoromethylbenzoyl)imino-5-n-propyl-3-[2'-(1H-tetrazol-5-yl)biphenyl-4-yl]methyl-1,3,4-thiadiazoline [Compound No. 81]:
Property colorless powder
¹H-NMR(δppm in CDCl₃)
8.13(1H,d), 7.88(1H,d), 7.75(1H,d), 7.51–7.76(5H,m), 7.43(2H,d), 7.21(2H,d), 5.57(2H,s), 2.84(2H,t), 1.76–1.84 (2H,m), 1.03(3H,t)

(45) 2-(2-Trifluoromethylbenzoyl)imino-5-n-butyl-3-[2'-(1H-tetrazol-5-yl)biphenyl-4-yl]methyl-1,3,4-thiadiazoline [Compound No. 82]:
Property colorless powder
¹H-NMR(δppm in CDCl₃)
8.18(1H,d), 7.90(1H,d), 7.75(1H,d), 7.47–7.76(5H,m), 7.43(2H,d), 7.24(2H,d), 5.58(2H,s), 2.89(2H,t), 1.40–1.79 (4H,m), 0.96(3H,t)

(46) 2-(2-Trifluoromethoxybenzoyl)imino-5-ethyl-3- [2'-(1H-tetrazol-5-yl)biphenyl-4-yl]methyl-1,3,4-thiadiazoline [Compound No. 83]:
Property colorless powder
¹H-NMR(δppm in CDCl₃)
8.12–8.15(2H,m), 7.15–7.60(10H,m), 5.59(2H,s), 2.88 (2H,q), 1.36(3H,t)

(47) 2-(2-Nitrobenzoyl)imino-5-ethyl-3-[2'-(1H-tetrazol-5-yl)biphenyl-4-yl]methyl-1,3,4 -thiadiazoline [Compound No. 84]:
Property colorless powder
¹H-NMR(δppm in DMSO-d₆)
8.06(1H,d), 7.53–7.87(7H,m), 7.31(2H,d), 7.09(2H,d), 5.55(2H,s), 2.95(2H,q), 1.27(3H,t)

(48) 2-(3-Nitrobenzoyl)imino-5-ethyl-3-[2'-(1H-tetrazol-5-yl)biphenyl-4-yl]methyl-1,3,4-thiadiazoline [Compound No. 85]:
Property colorless powder
¹H-NMR(δppm in DMSO-d₆)
8.91(1H,s), 8.64(1H,d), 8.42(1H,d), 7.19–7.88(4H,m), 7.38 (2H, d), 7.12 (2H, d), 6.78–6.82(1H,m), 5.68(2H,s), 2.96(2H,q), 1.29(3H,t)

(49) 2-(4-Nitrobenzoyl)imino-5-ethyl-3-[2'-(1H-tetrazol-5-yl)biphenyl-4-yl]methyl-1,3,4-thiadiazoline [Compound No. 86]:
Property colorless powder
¹H-NMR(δppm in DMSO-d₆)
8.48(2H,d), 8.36(2H,d), 7.23–7.60(4H,m), 7.11(2H,d), 6.81(2H,d), 5.66(2H,s), 2.92(2H,q), 1.30(3H,t)

(50) 2-(2,4-Dimethoxybenzoyl)imino-5-ethyl-3-[2'-(1H-tetrazol-5-yl)biphenyl-4-yl]methyl-1,3,4-thiadiazoline [Compound No. 87]:
Property pale yellow powder
¹H-NMR(δppm in CDCl₃)
8.26(1H,d), 7.92–8.00(1H,m),7.00–7.60 (7H,m), 6.49–6.59(2H,m), 5.55(2H,s), 3.88(3H,s), 3.80(3H,s), 2.79 (2H,q), 1.29(3H,t)

(51) 2-(2,6-Dichlorobenzoyl)imino-5-ethyl-3-[2'-(1H-tetrazol-5-yl)biphenyl-4-yl]methyl-1,3,4 -thiadiazoline [Compound No. 88]:
Property colorless powder
¹H-NMR(δppm in CDCl₃)
8.14 (1H,d), 7.20–7.65(10H,m), 5.54(2H,s), 2.93(2H,q), 1.39 (3H,t)

(52) 4-[[5-Ethyl-3-[2'-(1H-tetrazol-5-yl)biphenyl-5-yl] methyl-1,3,4 -thiadiazoline-2-yliden]aminocarbonyl] benzoic acid methyl ester [Compound No.89]:
Property colorless crystals
Melting point 238°–240° C.
¹H-NMR(δppm in CDCl₃)
8.37(2H,dd), 8.12(2H,d), 7.26–7.62(8H,m), 5.68(2H,s), 3.95(3H,s), 2.92(2H,q), 1.39(3H,t)

(53) 6-Nitro-N-[[5-Ethyl-3-[2'-(1H-tetrazol-5-yl)-biphenyl-4-yl]methyl-1,3,4-thiadiazoline-2-yliden]phthalamic Acid ethyl ester [Compound No. 90]:
Property colorless powder ¹H-NMR(δppm in CDCl₃)

8.10–8.19(3H,m), 7.22–7.62(8H,m), 5.46(2H,s), 4.24 (2H,q), 2.93(2H,q), 1.40(3H,t), 1.21(3H,t)

(54) 2-(2-Thenoyl)imino-5-ethyl-3-[2'-(1H-tetrazol-5-yl)biphenyl-4-yl]methyl-1,3,4-thiadiazoline Compound No. 91]:

Property colorless crystals
Melting point 192°–193.5° C.
¹H-NMR(δppm in CDCl₃)
8.14(1H,dd), 7.90(1H,d), 7.53–7.58 (5H,m), 7.39 (1H,d), 7.21(2H,d), 7.12(1H,dd), 5.55(2H,s), 2.88 (2H,q),1.36(3H,t)

(55) 2-(2-Furoyl)imino-5-ethyl-3-[2'-(1H-tetrazol-5-yl)biphenyl-4-yl]methyl-1,3,4-thiadiazoline [Compound No. 92]:

Property colorless crystals
Melting point 212°–213° C.
¹H-NMR(δppm in DMSO-d₆)
7.92 (1H,brs), 7.53–7.68 (4H,m), 7.31–7.35 (3H,m), 7.10(2H,d), 6.67(1H,brs), 5.57(2H,s), 2.91(2H,q), 1.26 (3H,t)

(56) 2-Nicotinoylimino-5-ethyl-3-[2'-(1H-tetrazol-5-yl)biphenyl-4-yl]methyl-1,3,4-thiadiazoline hydrochloric acid [Compound No. 93]:

Property colorless crystals
Melting point 224°–225° C.
¹H-NMR(δppm in DMSO-d₆)
9.48(1H,s), 8.86–8.91(2H,m), 7.10–7.85(9H,m), 5.72 (2H,s), 2.97(2H,q), 1.29(3H,t)

(57) 2-picolinoylimino-5-ethyl-3-[2'-(1H-tetrazol-5-yl)biphenyl-4-yl]methyl-1,3,4-thiadiazoline hydrochloric acid [Compound No. 94]:

Property colorless crystals
Melting point 228°–229° C.
¹H-NMR(δppm in DMSO-d₆)
8.83–8.85(1H,m), 8.57–8.60(1H,m), 8.35(1H,m), 7.85–7.95(1H,m), 7.51–7.67(4H,m), 7.35(2H,d), 7.10(2H,d), 5.75(2H,s), 2.97(2H,q), 1.29(3H,t)

(58) 2-isonicotinoylimino-5-ethyl-3-[2'-(1H-tetrazol-5-yl)biphenyl-4-yl]methyl-1,3,4-thiadiazoline hydrochloric acid [Compound No. 95]:

Property colorless crystals
Melting point 233°–235° C.
¹H-NMR(δppm in DMSO-d₆)
8.80(2H,d), 8.57–8.08(2H,d), 7.52–7.70(4H,m), 7.35(2H,d), 7.11(2H,d), 5.68(2H,s), 2.96(2H,q), 1.28 (3H,t)

(59) 2-(2-Thiopheneacetyl)imino-5-ethyl-3-[2'-(1H-tetrazol-5-yl)biphenyl-4-yl]methyl-1,3,4-thiadiazoline [Compound No. 96]:

Property colorless powder
¹H-NMR (δppm in CDCl₃)
8.07(1H,d), 6.90–7.66(10H,m), 5.45(2H,s), 4.03(2H,s), 2.86(2H,q), 1.31(3H,t)

(60) 2-(3-Chloro-2-thenoyl)imino-5-ethyl-3-[2'-(1H-tetrazol-5-yl)biphenyl-4-yl]methyl-1,3,4-thiadiazoline [Compound No. 97]:

Property colorless crystals
Melting point 179°–180° C.
¹H-NMR(δppm in CDCl₃)
8.20(1H,dd), 7.57–7.60(4H,m), 7.38–7.44 (2H,m), 7.23–7.26(2H,m), 7.02(1H,d), 5.57(2H,s), 2.90(2H,q), 1.36 (3H,t)

(61) 2-(3-Chloro-4-methansulfonyl-2-thenoyl)imino-5-ethyl-3-[2'-(1H-tetrazol-5-yl)biphenyl-4-yl]methyl-1,3,4-thiadiazoline [Compound No. 98]:

Property colorless crystals
Melting point 168°–170° C.
¹H-NMR(δppm in CDCl₃)
8.31(1H,brs), 8.07–8.12(1H,m), 7.26–7.56(7H,m), 5.58 (2H,s), 3.25(3H,s), 2.92(2H,q), 1.38(3H,t)

(62) 2-(4-Methyl-1,2,3-thiadiazole-5-carbonyl)imino-5-ethyl-3-[2'-(1H-tetrazol-5-yl)biphenyl-4-yl]methyl-1,3,4-thiadiazoline [Compound No. 99]:

Property colorless crystals
Melting point 198°–200° C.
¹H-NMR(δppm in CDCl₃)
8.20(1H,d), 7.26–7.58(7H,m), 5.57(2H,s), 3.03(3H,s), 2.95(2H,q), 1.40(3H,t)

(63) 2-(5-Methylisoxazole-3-carbonyl)imino-5-ethyl-3-[2'-(1H-tetrazol-5-yl) biphenyl-4-yl]methyl-1,3,4-thiadiazoline [Compound No. 100]:

Property colorless crystals
Melting point 155°–160° C.
¹H-NMR(δppm in CDCl₃)
8.06(1H,d), 7.51–7.59(2H,m), 7.34–7.37 (1H,m), 7.30 (2H,d), 7.07(2H,d), 6.54(1H,s), 5.51(2H,s), 2.91(2H,q), 2.49 (3H,s), 1.37(3H,t)

Example 5

Compounds No.101 and No. 102 were obtained by hydrolysis of compounds No.89 and No.90 obtained in Example 4 with aqueous sodium hydroxide solution.

(1) 4-[[5-Ethyl-3-[2'-(1H-tetrazol-5-yl)biphenyl-4-yl]methyl-1,3,4-thiadiazoline-2-yliden]aminocarbonyl]benzoic acid[Compound No. 101]:

Property colorless crystals
Melting point 233°–235° C.
¹H-NMR(δppm in DMSO-d₆) 8.36(2H,d), 8.04(2H,d), 7.52–7.70(4H,m), 7.37 (2H,d), 7.11(2H,d), 5.69(2H,s), 2.94 (2H,q), 1.29(3H,t)

(2) 6-Nitro-N-[[5-Ethyl-3-[2'-(1H-tetrazol-5-yl)-biphenyl-4-yl]methyl-1,3,4-thiadiazoline-2-yliden]phthalamic acid [Compound No. 102]:

Property colorless powder
¹H-NMR(δppm in DMSO-d₆)
8.12–8.32(3H,m), 7.03–7.78(5H,m), 5.42(2H,s), 2.93 (2H,q), 1.27(3H,t)

Example 6

2-(2-Chlorobenzoyl)imino-5-ethyl-3-(2'-cyanobiphenyl-4-yl)methyl-1,3,4-thiadiazoline [Compound No.103]:

When the reaction (example 6) was carried out in a similar manner to example 3 using 4'-bromomethyl-2-cyanobiphenyl instead of 4'-bromomethyl-2-(N-triphenylmethyltetrazol-5-yl)biphenyl as a reactant, the title compound No.103 was obtained.

Property colorless crystals
Melting point 117°–118° C.
¹H-NMR(δppm in CDCl₃)
8.06(1H,d), 7.77(1H,d), 7.32–7.67(10H,m), 5.63(2H,s), 2.92(2H,q), 1.38(3H,t)

Example 7

(1) 2-Acetylimino-5-ethyl-3-[2'-(1H-tetrazol-5-yl)-biphenyl-4-yl]methyl-1,3,4-thiadiazoline [Compound No.104]:

To a suspension of sodium hydride(70 mg 55% in oil) in N,N-dimethylformamide (5 ml) was added 2-ethyl-5-acetylamino-1,3,4-thiadiazole (0.26 g) at room temperature. When evolution of hydrogen ceased, a solution of 4'-bromomethyl-2-(N-triphenylmethyltetrazol-5-yl)biphenyl (0.8 g) in N,N-dimethylformamide (5 ml) was added to the mixture. After stirring for 25 hours at room temperature, water and ethyl acetate were added to the mixture. The organic layer was separated, washed with water and then dried over anhydrous magnesium sulfate. The magnesium sulfate was removed by filtration and the filtrate was evaporated. The residue containing two major products on thin-layer chromatography was separated by column chromatography on silica gel (eluent:chloroform). The first eluted fractions were collected and the solvent was evaporated. To the residue were added dioxane (5 ml) and 10% hydrochloric acid solution (1 ml), and the mixture was stirred for 1 hour at room temperature. The reaction mixture was made basic with 5% aqueous sodium hydroxide solution. The aqueous layer was washed with ether, adjusted to about pH 2 with 10% hydrochloric acid solution, and extracted with ethyl acetate. The organic layer was separated, washed with water and dried over anhydrous magnesium sulfate. The magnesium sulfate was removed by filtration and the filtrate was evaporated. The title compound (No.104) was obtained as a colorless powder (80 mg).

Property colorless powder
$^1$H-NMR($\delta$ppm in CDCl$_3$)
8.08(1H,d), 7.51–7.62(2H,m), 7.39–7.45(1H,m), 7.34(2H,d), 7.17(2H,d), 5.47(2H,s), 2.83(2H,q), 2.21 (3H,s), 1.32 (3H,t)

(2) 2-[2'-(1H-tetrazol-5-yl)biphenyl-4-yl]methylamino-5-ethyl-1,3,4-thiadiazole hydrochloric acid [Compound No.105]:

The residue containing two major products described in example 7(1) was separated by column chromatography on silica gel (eluent: chloroform).

The secondly eluted fractions were collected and the solvent was evaporated. To the residue were added dioxane (5 ml) and 10% hydrochloric acid solution (1 ml), and the mixture was stirred for 1 hour at room temperature. The reaction mixture was made basic with 5% sodium hydroxide solution and the mixture was stirred for 30 minutes. The aqueous layer was washed with ether and adjusted to about pH 2 with 10% hydrochloric acid solution. The precipitated solid was filtrated, well washed with water and dried. The title compound No.104 was obtained as colorless crystals (100 mg).

Property colorless crystals
Melting point 200°–202° C.
$^1$H-NMR($\delta$ppm in DMSO-d$_6$)
8.11(1H,t), 7.54–7.72(4H,m), 7.28(2H,d), 7.07(2H,d), 4.45(2H,d), 2.81(2H,q), 1.21(3H,t)

Example 8

Compounds Nos.106–109 were synthesized in a similar manner to example 7 (1) and (2).
(1) 2-Acetylimino-5-methyl-3-[2'-(1H-tetrazol-5-yl)-biphenyl-4-yl]methyl-1,3,4-thiadiazoline [Compound No.106]:
Property colorless crystals
Melting point 128°–133° C.
$^1$H-NMR($\delta$ppm in DMSO-d$_6$)
7.55–7.71(4H,m), 7.22(2H,d), 7.08(2H,d), 5.46(2H,s), 2.50(3H,s), 2.19(3H,s)
(2) 2-[2'-(1H-tetrazol-5-yl)biphenyl-4-yl]methylamino-5-methyl-1,3,4-thiadiazole hydrochloric acid [Compound No. 107]:
Property colorless crystals
Melting point 196°–198° C.
$^1$H-NMR($\delta$ppm in DMSO-d$_6$)
8.05(1H,t), 7.54–7.72(4H,m), 7.28(2H,d), 7.07(2H,d), 4.47(2H,d), 2.45(3H,s)

(3) 2-Acetylimino-5-ethylthio-3-[2'-(1H-tetrazol-5-yl)-biphenyl-4-yl]methyl-1,3,4 -thiadiazoline [Compound No. 108]:
Property colorless crystals
Melting point 174°–175° C.
$^1$H-NMR($\delta$ppm in CDCl$_3$)
8.19(1H,d), 7.42–7.63(3H,m), 7.44(2H,d), 7.24(2H,d), 5.52(2H,s), 3.17(2H,q), 2.29(3H,s), 1.42(3H,t)
(4) 2-[2'-(1H-tetrazol-5-yl)biphenyl-4-yl]methylamino-5-ethylthio-1,3,4-thiadiazole hydrochloric acid [Compound No. 109]:
Property colorless crystals
Melting point 184°–187° C.
$^1$H-NMR($\delta$ppm in DMSO-d$_6$)
8.32(1H,t), 7.56–7.68(4H,m), 7.29(2H,d), 7.08(2H,d), 4.47(2H,d), 3.07(2H,q), 1.28(3H,t)

Example 9

2-[2'-(1H-tetrazol-5-yl)biphenyl-4-yl]methylamino-5-cyclopropyl-1,3,4-thiadiazole hydrochloric acid [Compound No. 110]:

Compound No.4 obtained in example 12(2) was deacetylation with 5% sodium hydroxide solution to give the title compound No.110.

Property colorless crystals
Melting point 203°–205° C.
$^1$H-NMR($\delta$ppm in DMSO-d$_6$)
8.07(1H,t), 7.57–7.69(4H,m), 7.27(2H,d), 7.07(2H,d), 4.43(2H,d), 2.15–2.21(1H,m), 0.98–1.05(2H,m), 0.79–0.83(2H,m)

Example 10

2-Imino-5-ethyl -3-[2'-(1H-tetrazol-5-yl)biphenyl-4-yl] methyl-1,3,4 -thiadiazoline [Compound No. 111]:

Compound No.104 (70 mg) obtained in example 7 (1) was added to a mixture of ethanol (4 ml) and 10% sodium hydroxide solution (4 ml), and the mixture was refluxed for 2 hours. After cooling, the reaction mixture was adjusted to about pH 4 with 10% hydrochloric acid solution and then extracted with ethyl acetate. The organic layer was washed with water and dried over anhydrous magnesium sulfate. The magnesium sulfate was removed by filtration and the filtrate was evaporated. The resultant oil crystallized on standing. Diisopropyl ether was added, and the crystals were filtrated and dried. The title compound(No. 111) was obtained as colorless crystals (22 mg).

Property colorless crystals
Melting point 180°–182° C.
$^1$H-NMR($\delta$ppm in DMSO-d$_6$)
7.53–7.68(4H,m), 7.30(2H,d), 7.07(2H,d), 6.59(1H,m), 4.02(2H,brs), 2.46(2H,q), 1.11(3H,t)

Example 11

2-Imino-5-ethylthio-3-[2'(1H-tetrazol-5-yl)biphenyl-4-yl]methyl-1,3,4-thiadiazoline [Compound No. 112]:

Compound No.112 was derived from compound No.108 obtained in example 8(3) in a similar manner to example 10.
Property yellow powder
$^1$H-NMR($\delta$ppm in DMSO-d$_6$)
7.04–7.72(8H,m), 5.95(1H,m), 3.90(2H,brs), 3.05(2H,q), 1.21(3H,t)

Example 12

Using diisopropylethylamine as a base in Preparation Process-1, the compounds shown below were synthesized.

2-Phenylacetylimino-5-ethyl-3-[2'-(1H-tetrazol-5-yl) biphenyl-4-yl]methyl-1,3,4-thiadiazoline [Compound No.113]:

2-Phenylacetylamino-5-ethyl-1,3,4-thiadiazole (180 mg) and 4'-bromomethyl-2-(N-triphenylmethyltetrazol-5-yl)-biphenyl (400 mg) was added to a mixture of N,N-dimethylformide (5 ml) and diisopropylethylamine (100 mg), then the mixture was stirred at 80° C. on oil bath for 5 hours. After cooling, water and ethyl acetate were added. The organic layer was separated, washed with water and dried over anhydrous magnesium sulfate. The magnesium sulfate was removed by filtration and the filtrate was evaporated. The residue was purified by column chromatography on silica gel (eluent:chloroform). The fractions containing main product were collected and the solvent was evaporated.

To the residue were added dioxane (4 ml) and 10% hydrochloric acid solution (1 ml) and the mixture was stirred for 20 hours at room temperature. The reaction mixture was made basic with 5% aqueous sodium hydroxide solution. The aqueous layer was washed with ether, neutralized with 10% hydrochloric acid solution, and extracted with ethyl acetate. The organic layer was separated, washed with water and dried over anhydrous magnesium sulfate. The magnesium sulfate was removed by filtration and the filtrate was evaporated. The resultant oil crystallized on standing. Diisopropyl ether was added, and the crystals were filtrated and dried. The title compound No. 113 was obtained as colorless crystals (17 mg).

Property10
colorless crystals
Melting point 149°–151° C.
$^1$H-NMR($\delta$ppm in CDCl$_3$)
8.23(1H,dd), 7.16–7.61(12H,m), 5.43(2H,s), 3.86(2H,s), 2.83(2H,q), 1.32(3H,t)

Example 13

Compounds Nos.114~116 were synthesized in a similar manner to example 12.
(1) 2- (2-Chlorophenyl)acetylimino-5-ethyl-3-[2'-(1H-tetrazol-5-yl)biphenyl-4-yl]methyl-1,3,4 -thiadiazoline [Compound No. 114]:
Property colorless powder
$^1$H-NMR($\delta$ppm in CDCl$_3$)
8.03(1H,d), 7.16–7.68(11H,m), 5.34(2H,s), 3.98(2H,s), 2.81(2H,q) , 1.32(3H,t)
(2) 2-Phenoxyacetylimino-5-ethyl-3-[2'-(1H-tetrazol-5-yl)biphenyl-4-yl]methyl-1,3,4-thiadiazoline [Compound No. 115]:
Property colorless crystals
Melting point 243°–246° C.
$^1$H-NMR($\delta$ppm in CDCl$_3$)
7.91(1H,d), 6.92–7.60(12H,m), 5.41(2H,s), 4.85(2H,s), 2.88(2H,q), 1.34 (3H,t)
(3) 2- (2-Chlorophenoxy)acetylimino-5-ethyl-3-[2'-(1H-tetrazol-5-yl)biphenyl-4-yl]methyl-1,3,4-thiadiazoline [Compound No. 116]:
Property colorless crystals
Melting point 210°–212° C.
$^1$H-NMR($\delta$ppm in CDCl$_3$)
8.22 (1H,dd), 6.84–7.63 (11H,m), 5.42 (2H,s), 4.93(2H,s) , 2.88(2H,q) , 1.35(3H,t)

Example 14

Using potassium carbonate as a base in Preparation Process-1, the compounds shown below were synthesized.
2- (2-Bromobenzoyl)imino-5-ethyl-3-[2'-(1H-tetrazol-5-yl)biphenyl-4-yl]methyl-1,3,4-thiadiazoline [Compound No. 117]:

To a suspension of potassium carbonate (100 mg) in N,N-dimethylformamide (5 ml) was added 2-ethyl-5-(2-Bromobenzoyl)amino-1,3,4 -thiazole (156 mg) and 4'-bromomethyl-2-(N-triphenylmethyltetrazol-5-yl) biphenyl (279 mg), then the mixture was stirred at 80° C. on oil bath for 3 hours. After cooling, water and ethyl acetate were added. The organic layer was separated, washed with water and dried over anhydrous magnesium sulfate. The magnesium sulfate was removed by filtration and the filtrate was evaporated. The residue was purified by column chromatography on silica gel (eluent:chloroform/methanol=40/1). The fractions containing main product were collected and the solvent was evaporated.

To the residue was added tetrahydrofuran (4 ml) and 20% hydrochloric acid solution (1 ml), and the mixture was stirred for 20 hours at room temperature. The reaction mixture was made basic with 5% sodium hydroxide. The aqueous layer was washed with ether, neutralized with 20% hydrochloric acid solution, and extracted with ethyl acetate. The organic layer was separated, washed with water and dried over anhydrous magnesium sulfate. The magnesium sulfate was removed by filtration and the filtrate was evaporated. The resultant oil crystallized on standing. Ether was added, and the crystals were filtrated and dried. The title compound No.117 was obtained as colorless crystals (85 mg).

Property colorless crystals
Melting point 125°–129° C.
$^1$H-NMR($\delta$ppm in CDCl$_3$)
8.06(1H,m) , 7.96(1H,dd), 7.62(2H,d) , 7.55(2H,m) , 7.35–7.51(4H,m), 7.18(2H,d), 5.58(2H,s), 2.90(2H,q), 1.37 (3H, t)

Example 15

Compounds Nos.118~125 were synthesized in a similar manner to example 14.
(1) 2- (3-Bromobenzoyl)imino-5-ethyl-3-[2'-(1H-tetrazol-5-yl)biphenyl-4-yl]methyl-1,3,4-thiadiazoline [Compound No. 118]:
Property colorless crystals
Melting point 193°–194° C.
$^1$H-NMR($\delta$ppm in CDCl$_3$)
8.44(1H,d), 8.19(2H,dd), 7.48–7.66(6H,m), 7.23–7.42 (3H,m), 5.64(2H,s), 2.91(2H,q), 1.38(3H,t)
(2) 2-(4-Bromobenzoyl)imino-5-ethyl-3-[2'-(1H-tetrazol-5-yl)biphenyl-4-yl]methyl-1,3,4-thiadiazoline [Compound No.119]:
Property colorless powder
$^1$H-NMR($\delta$ppm in CDCl$_3$)
8.61(1H,d), 8.18(2H,m), 7.55–7.77(6H,m), 7.20–7.42 (3H,m), 5.66(2H,s), 2.91(2H,q), 1.38(3H,t)
(3) 2-(2-Toluoyl)imino-5-ethyl-3-[2'-(1H-tetrazol-5-yl) biphenyl-4-yl]methyl-1,3,4-thiadiazoline [Compound No. 120]:
Property colorless crystals
Melting point 189°–191° C.
$^1$H-NMR($\delta$ppm in CDCl$_3$)
8.16(2H,m), 7.55(2H,m), 7.45(2H,m), 7.36(2H,m), 7.22 (4H,m), 5.60(2H,s), 2.89(2H,q), 2.67(3H,s), 1.37 (3H,t)
(4) 2-(3-Toluoyl)imino-5-ethyl-3-[2'-(1H-tetrazol-5-yl) biphenyl-4-yl]methyl-1,3,4-thiadiazoline [Compound No.121]:
Property colorless crystals
Melting point 179°–180° C.
$^1$H-NMR($\delta$ppm in CDCl$_3$)
8.10 (3H,m), 7.49–7.60(4H,m), 7.33–7.36(3H,m), 7.18 (2H,d), 5.60(2H,s), 2.87(2H,q), 2.42(3H,s), 1.35 (3H,t)

(5) 2-(4-Toluoyl)imino-5-ethyl-3-[2'-(1H-tetrazol-5-yl) biphenyl-4-yl]methyl-1,3,4-thiadiazoline [Compound No. 122]:
Property colorless crystals
Melting point 208°–212° C.
$^1$H-NMR($\delta$ppm in CDCl$_3$+CD$_3$OD)
8.21 (2H,d), 7.85(1H,d), 7.52(2H,m), 7.42(3H,m), 7.26 (2H,d), 7.15(2H,d), 5.60(2H,s), 2.88(2H,q), 2.42(3H,s), 1.36 (3H, t)

(6) 2-(1-Naphthoyl)imino-5-ethyl-3-[2'-(1H-tetrazol-5-yl) biphenyl-4-yl]methyl-1,3,4 -thiadiazoline [Compound No. 123]:
Property pale brown powder
$^1$H-NMR($\delta$ppm in CDCl$_3$)
9.11(1H,d), 8.40(1H,d), 8.07(1H,d), 7.97(1H,m), 7.85 (1H,m), 7.33–7.60(6H,m), 7.19(2H,d), 6.90(2H,brs), 5.61 (2H,s), 2.91(2H,q), 1.39(3H,t)

(7) 2-(2-Naphthoyl)imino-5-ethyl-3-[2'-(1H-tetrazol-5-yl) biphenyl-4-yl]methyl-1,3,4-thiadiazoline [Compound No. 124]:
Property colorless crystals
Melting point 213°–215° C.
$^1$H-NMR($\delta$ppm in CDCl$_3$+CD$_3$OD)
8.87(1H,s), 8.36(1H,d), 7.99(1H,d), 7.90(2H,d), 7.79(1H, d), 7.44–7.60(7H,m), 7.17(2H,d), 5.67(2H,s), 2.89(2H,q), 1.38(3H,t)

(8) 1-[[5-Ethyl-3-[2'-(1H-tetrazol-5-yl)biphenyl-4-yl]-methyl-1,3,4-thiadiazoline-2-yliden]aminocarbonyl] cyclopropan-carboxylic acid ethyl ester [Compound No. 125]:
Property colorless powder
$^1$H-NMR($\delta$ppm in CDCl$_3$)
7.90(1H,s), 7.45(2H,m), 7.24–7.42 (5H,m), 5.47 (2H,s), 4.23 (2H,q), 2.85(2H,q), 1.56(4H,m), 1.37(3H,t), 1.29 (3H, t)

Synthetic methods of thiadiazoline derivatives by preferable preparation Process 2 in the present invention were described as below (example 16~example 23). [Syntheses of thiadiazoline derivatives]

Reference Example 3

2-Imino-5-ethyl-3-[2'-(N-triphenylmethyltetrazol-5-yl) biphenyl-4-yl]methyl-1,3,4-thiadiazoline To a suspension of sodium hydride (43 mg, 55% in oil) in N,N-dimethylformamide (10 ml) was added 2-ethyl-5-trifluoroacetylamino-1,3,4-thiadiazole (225 mg) at room temperature. When evolution of hydrogen ceased, 4'-bromomethyl-2-(N-triphenylmethyltetrazol-5-yl) biphenyl (557 mg) was added, and then the mixture was stirred at 70° C. on oil bath for 10 hours. After cooling, water and ethyl acetate were added. The organic layer was separated, washed with water and dried over anhydrous magnesium sulfate. The magnesium sulfate was removed by filtration and the filtrate was evaporated. The residue was purified by column chromatography on silica gel (eluent:chloroform). The fractions containing main product were collected and the solvent was evaporated.

To the residue was added tetrahydrofuran (20 ml) and 5% sodium hydroxide (2 ml), and the mixture was stirred at 70° C. on oil bath for 6 hours. After cooling, the solvent was removed in vacuo. Water and chloroform were added to the residue. The organic layer was separated, washed with water and dried over anhydrous magnesium sulfate. The magnesium sulfate was removed by filtration and the filtrate was evaporated. The residue was purified by column chromatography on silica gel (eluent:chloroform/methanol=20/1) to give the title compound as a colorless powder (400 mg) .

Property colorless powder
$^1$H-NMR($\delta$ppm in CDCl$_3$)
7.91(1H,d), 7.47(2H,m), 7.19–7.44(10H,m), 7.12(4H,dd), 6.88(6H,d), 4.96(2H,s), 2.56(2H,q), 1.20 (3H,t)

2-Imino-5-methyl-3-[2'-(N-triphenylmethyltetrazol-5-yl) -biphenyl-4-yl]methyl-1,3,4-thiadiazolin, 2-imino-5-n-propyl-3-[2'-(N-triphenylmethyltetrazol-5-yl)biphenyl-4-yl] methyl-1,3,4-thiadiazoline, 2-imino-5-isopropyl-3-[2'-(N-triphenylmethyltetrazol-5-yl)biphenyl-4-yl]methyl-1,3,4-thiadiazoline and 2-imino-5-cyclopropyl-3-[2'-(N-triphenylmethyltetrazol-5-yl)biphenyl-4-yl]methyl-1,3,4-thiadiazoline were synthesized in a similar manner as above.

Example 16

N-[5-Ethyl-3-[2'-(1H-tetrazol-5-yl)biphenyl-4-yl]methyl-1,3,4-thiadiazoline-2-yliden]phthalamic acid [Compound No. 126]:

2 -Imino-5-ethyl-3-[2'-(N-triphenylmethyltetrazol-5-yl)-biphenyl-4-yl]methyl-1,3,4-thiadiazoline (60 mg) and phthalic anhydride (15 mg) were added to N,N-dimethylformamide (1 ml), and the mixture was stirred for 20 hours at room temperature. Water and ethyl acetate were added to the mixture, the organic layer was separated, washed with water and evaporated. 5% Sodium hydroxide solution and ether were added to the residue. The aqueous layer was separated, neutralized with 20% hydrochloric acid solution, and extracted with chloroform. The organic layer was separated, washed with water and dried over anhydrous magnesium sulfate. The magnesium sulfate was removed by filtration and the filtrate was evaporated.

To the residue were added dioxane (3 ml) and 20% hydrochloric acid solution (0.1 ml), and the mixture was stirred for 20 hours at room temperature. The reaction mixture was made basic with 5% aqueous sodium hydroxide solution. The aqueous layer was washed with ether, neutralized with 10% hydrochloric acid, and extracted with chloroform. The organic layer was separated, washed with water and dried over anhydrous magnesium sulfate. The magnesium sulfate was removed by filtration and the filtrate was evaporated. The title compound No.126 was obtained as a colorless powder (20 mg).

Property colorless powder
$^1$H-NMR($\delta$ppm in CDCl$_3$)
8.03(1H,d), 7.94(1H,d), 7.80(1H,d), 7.22–7.60(7H,m), 7.06(2H,d), 5.48(2H,s), 2.86(2H,q), 1.35(3H,t)

Example 17

Compounds Nos.127~151 were synthesized in a similar manner to example 16.

(1) 3-[[5-Ethyl-3-[2'- (1H-tetrazol-5-yl)biphenyl-4-yl] methyl-1,3,4-thiadiazoline-2-yliden]aminocarbonyl]-propenoic acid [Compound No. 127]:
Property colorless powder
$^1$H-NMR ($\delta$ppm in CDCl$_3$+CD$_3$OD)
7.82(1H,d), 7.41–7.73(3H,m), 7.36(2H,d), 7.31(1H,s), 7.18(2H,dd), 6.93(1H,d), 5.52(2H,s), 2.90(2H,q), 1.35 (3H, t)

(2) 3-[[5-Ethyl-3-[2'-(1H-tetrazol-5-yl) biphenyl-4-yl] methyl-1,3,4-thiadiazoline-2-yliden]aminocarbonyl]-atropic acid[Compound No. 128]:
Property colorless powder
$^1$H-NMR($\delta$ppm in CDCl$_3$)
7.80(2H,m), 7.32–7.61(8H,m), 7.03–7.20(4H,m), 5.46 (2H,s), 2.85(2H,q), 1.36(3H,t)

(3) 2-[[5-Methyl-3-[2'-(1H-tetrazol-5-yl)biphenyl-4-yl] methyl-1,3,4-thiadiazoline-2-yliden]8minocarbonyl]-1-cyclopenten carboxylic acid [Compound No.129]:

Property colorless powder
¹H-NMR(δppm in DMSO-d₆)
7.52–7.71 (4H,m), 7.33(2H,d), 7.09(2H,d), 5.49(2H,s), 2.74–2.80(4H,m), 2.55(3H,s), 1.85–1.91 (2H,m)

(4) 2-[[5-Ethyl-3-[2'-(1H-tetrazol-5-yl)biphenyl-4-yl] methyl-1,3,4-thiadiazoline-2-yliden]aminocarbonyl]-1-cyclopenten carboxylic acid [Compound No. 130]:
Property colorless crystals
Melting point 234°–235° C.
¹H-NMR(δppm in CDCl₃+CD₃OD)
7.76(1H,d), 7.35–7.65(3H,m), 7.29(2H,d), 7.11(2H,d), 5.52(2H,s), 3.03(4H,t), 2.94(2H,q), 1.89(2H,m), 1.39 (3H,t)

(5) 2-[[5-n-Propyl-3-[2'- (1H-tetrazol-5-yl)biphenyl-4-yl] methyl-1,3,4-thiadiazoline-2-yliden]aminocarbonyl]-1-cyclopenten carboxylic acid [Compound No. 131]:
Property colorless powder
¹H-NMR(δppm in CDCl₃)
7.95–7.99(1H,m), 7.15–7.61(7H,m), 5.55(2H,s), 3.03–3.09(2H,m), 2.88–2.98(4H,m), 1.76–1.92(4H,m), 1.05 (3H, t)

(6) 2- [[5-Cyclopropyl-3-[2'-(1H-tetrazol-5-yl)biphenyl-4-yl]methyl-1,3,4-thiadiazoline-2-yliden]aminocarbonyl]-1-cyclopetenecarboxylic acid [Compound No. 132]:
Property colorless crystals
Melting point 216°–218 ° C.
¹H-NMR(δppm in DMSO-d₆)
7.56–7.72 (4H,m), 7.31 (2H,d), 7.09(2H,d), 5.47(2H,s), 2.70–2.85 (4H,m), 2.32–2.38 (1H,m), 1.82–1.92 (2H,m), 1.12–1.20(2H,m), 0.95–1.10(2H,m)

(7) 2- [5-Isopropyl-3-[2'-(1H-tetrazol-5-yl)biphenyl-4-yl] methyl-1,3,4-thiadiazoline-2-yliden]aminocarbonyl]-1-cyclopenten carboxylic acid
[Compound No. 133]:
Property colorless powder
¹H-NMR(δppm in CDCl₃)
7.89(1H,d), 7.40–7.60(3H,m), 7.28(2H,d), 7.14(2H,d), 5.52(2H,s), 3.26(1H,septet), 3.05(2H,t), 2.92(2H,t), 1.86 (2H,quintet), 1.42 (6H,d)

(8) trans-2-[[5-Ethyl-3-[2'-(1H-tetrazol-5-yl)biphenyl-4-yl] methyl-1,3,4 -thiadiazoline-2-yliden]aminocarbonyl]-1-cyclohexane carboxylic acid
[Compound No. 134]:
Property colorless powder
¹H-NMR(δppm in CDCl₃)
7.90(1H,s), 7.35–7.63(3H,m), 7.08–7.33(4H,m), 5.45 (2H,s), 3.04(1H,m), 2.80(1H,m), 2.86(2H,q), 2.08(1H,m), 1.83(2H,m), 1.44(5H,m), 1.35(3H,t)

(9) N- [5-Methyl-3-[2'-(1H-tetrazol-5-yl)biphenyl-4-yl]-methyl-1,3,4 -thiadiazoline-2-yliden]phthalamic acid [Compound No. 135]:
Property colorless powder
¹H-NMR(δppm in CDCl₃)
8.02–8.05(2H,m), 7.89–7.93(2H,m), 7.82(2H,d), 7.25–7.58(4H,m), 7.06(2H,d), 5.47(2H,s), 2.53(3H,s)

(10) N-[5-n-Propyl-3-[2'-(1H-tetrazol-5-yl) biphenyl-4-yl] methyl-1,3,4-thiadiazoline-2-yliden]phthalamic acid [Compound No. 136]:
Property colorless powder
¹H-NMR(δppm in CDCl₃)
7.79–8.09(5H,m), 7.18–7.56(5H,m), 7.08(2H,d), 5.50 (2H,s), 2.84(2H,t), 1.79(2H,m), 1.01(3H,t)

(11) N-[5-Cyclopropyl-3-[2'-(1H-tetrazol-5-yl)biphenyl-4-yl]methyl-1,3,4-thiadiazoline-2-yliden]phthalamic acid [Compound No. 137]:
Property colorless powder
¹H-NMR(δppm in DMSO-d₆)
7.98–8.01(1H,m), 7.52–7.75(7H,m), 7.31(2H,d), 7.10 (2H,d), 5.54(2H,s), 2.32–2.38(1H,m), 1.12–1.20(2H,m), 0.95–1.10(2H,m)

(12) N-[5-Isopropyl-3-[2'-(1H-tetrazol-5-yl) biphenyl-4-yl] methyl-1,3,4-thiadiazoline-2-yliden]phthalamic acid [Compound No. 138]:
Property colorless powder
¹H-NMR(δppm in CDCl₃)
7.89–8.10(5H,m), 7.18–7.58(7H,m), 5.55(2H,s), 3.25 (1H,septet), 1.42 (6H,d)

(13) 3,6-Difluoro-N-[5-Ethyl-3-[2'-(1H-tetrazol-5-yl)-biphenyl-4-yl]methyl-1,3,4-thiadiazoline-2-yliden]-phthalamic acid [Compound No. 139]:
Property colorless powder
¹H-NMR(δppm in DMSO-d₆)
7.45–7.70(6H,m), 7.31(2H,d), 7.10(2H,d), 5.50(2H,s), 2.94(2H,q), 1.27(3H,t)

(14) Mixture of 3-[[5-Ethyl-3-[2'-(1H-tetrazol-5-yl) biphenyl-4-yl]methyl-1,3,4-thiadiazoline-2-yliden] aminocarbonyl]isophtalic acid and 2-[[5-Ethyl-3-[2'-(1H-tetrazol-5-yl) biphenyl-4-yl]methyl-1,3,4-thiadiazoline-2-yliden]aminocarbonyl]terephtalic acid [Compound No. 140]:
Property colorless powder
¹H-NMR(δppm in CDCl₃)
8.20(2H,d), 8.01(1H,m), 7.83(3H,m), 7.36–7.61(12H,m), 7.15(4H,m), 5.56(2H,s), 5.57(2H,s), 2.93(4H,m), 1.39 (6H, m)

(15) 2-[[5-Ethyl-3-[2'-(1H-tetrazol-5-yl)biphenyl-4-yl] methyl-1,3,4-thiadiazoline-2-yliden]aminocarbonyl]-nicotinic acid[Compound No. 141]:
Property colorless powder
¹H-NMR(δppm in CDCl₃)
7.81(1H,d), 7.16–7.50(5H,m), 7.13(1H,d), 6.70(4H,m), 5.46(2H,s), 2.86(2H,q), 1.34(3H,t)

(16) Mixture of 3-[[5-Ethyl-3-[2'-(1H-tetrazol-5-yl)-biphenyl-4 -yl]methyl-1,3,4 -thiadiazoline-2-yliden]-aminocarbonyl]isonicotinic acid and 4-[[5-Ethyl-3-[2'-(1H-tetrazol-5-yl)biphenyl-4-yl]-methyl-1,3,4-thiadiazoline-2-yliden]aminocarbonyl]-nicotinic acid [Compound No. 142]:
Property colorless powder
¹H-NMR(δppm in CDCl₃)
9.23(1H,s), 9.00(1H,s), 8.75(2H,m), 7.79–7.87(3H,m), 7.40–7.68(7H,m), 7.32(4H,m), 7.14(4H,m), 5.57(2H,s), 5.51(2H,s), 2.92(4H,m), 1.37(6H,m)

(17) 4-[[5-Ethyl-3-[2'-(1H-tetrazol-5-yl)biphenyl-4-yl] methyl-1,3,4-thiadiazoline-2-yliden]aminocarbonyl] thiophene-3-carboxylic acid [Compound No. 143]:
Property colorless crystals
Melting point 242°–245° C.
¹H-NMR(δppm in DMSO-d₆)
8.61(1H,d), 8.22(1H,d), 7.50–7.70(4H,m), 7.36(2H,d), 7.11(2H,d), 5.63(2H,s), 2.98(2H,q), 1.27(3H,t)

(18) 4-[[5-Cyclopropyl-3-[2'-(1H-tetrazol-5-yl)biphenyl-4-yl]methyl-1,3,4-thiadiazoline-2-yliden]aminocarbonyl] thiophene-3-carboxylic acid [Compound No. 144]:
Property colorless powder
¹H-NMR(δppm in DMSO-d₆)
8.61(1H,d), 8.22(1H,d), 7.50–7.70(4H,m), 7.34(2H,d), 7.11(2H,d), 5.59(2H,s), 2.33–2.41 (1H,m), 1.17–1.20(2H, m), 0.99–1.04 (2H,m)

(19) 4-[[5-Ethyl-3-[2'-(1H-tetrazol-5-yl)biphenyl-4-yl] methyl-1,3,4-thiadiazoline-2-yliden]aminocarbonyl]-furan-3-carboxylic acid [Compound No. 145]:
Property colorless powder
¹H-NMR(δppm in DMSO-d₆)
8.82(1H,d), 8.50(1H,d), 7.51–7.70(4H,m), 7.34 (2H,d), 7.11(2H,d), 5.64(2H,s), 2.33–2.41(1H,m), 2.98 (2H,q), 1.27 (3H,t)

(20) 3-[[5-Ethyl-3-[2'-(1H-tetrazol-5-yl)biphenyl-4-yl-methyl-1,3,4-thiadiazoline-2-yliden]aminocarbonyl]-pyrazine-2-carboxylic acid [Compound No. 146]:

Property colorless powder
$^1$H-NMR($\delta$ppm in DMSO-d$_6$)
8.87(1H,d), 8.81(1H,d), 7.52–7.72(4H,m), 7.31(2H,d), 7.10(2H,d), 5.56(2H,s), 2.95(2H,q), 1.28(3H,t)

(21) 3-[[5-n-Propyl-3-[2'-(1H-tetrazol-5-yl)biphenyl-4-yl]methyl-1,3,4-thiadiazoline-2-yliden]aminocarbonyl]-pyrazine-2-carboxylic acid [Compound No. 147]:
Property colorless crystals
Melting point 167°–170° C.
$^1$H-NMR($\delta$ppm in DMSO-d$_6$)
8.87(1H,s), 8.81(1H,s), 7.52–7.70(4H,m), 7.31(2H,d), 7.09(2H,d), 5.57(2H,s), 2.91(2H,t), 1.68–1.76(2H,m), 0.94 (3H, t)

(22) 3-[[5-Cyclopropyl-3-[2'-(1H-tetrazol-5-yl)biphenyl-4-yl]methyl -1,3,4-thiadiazoline-2-yliden]aminocarbonyl]-pyrazine-2-carboxylic acid [Compound No. 148]:
Property colorless crystals
Melting point 158°–160° C.
$^1$H-NMR($\delta$ppm in DMSO-d$_6$)
8.87(1H,s), 8.81(1H,s), 7.53–7.72(4H,m), 7.30(2H,d) 7.09(2H,d), 5.53(2H,s), 2.36–2.45(1H,m), 1.18–1.20(2H, m), 0.95–1.08(2H,m)

(23) 2-(2-Sulfobenzoyl)imino-5-ethyl-3-[2'-(1H-tetrazol-5-yl) biphenyl-4-yl]methyl-1,3,4-thiadiazoline [Compound No. 149]:
Property pale yellow powder
$^1$H-NMR($\delta$ppm in CDCl$_3$)
7.88(1H,d), 7.23–7.61(7H,m), 7.19(2H,d), 7.13(2H,d) 5.48(2H,s), 2.86(2H,q), 1.34(3H,t)

(24) 3-[[5-Ehyl-3-[2'-(1H-tetrazol-5-yl)biphenyl-4-yl]-methyl-1,3,4-thiadiazoline-2-yliden]aminosulfonyl]thenoic acid [Compound No. 150]:
Property colorless powder
$^1$H-NMR($\delta$ppm in CDCl$_3$)
7.85(2H,d), 7.37–7.69(6H,m), 7.09(4H,m), 5.25(2H,s) 2.82(2H,q), 1.32(3H,t)

(25) 2-[[5-Ethyl-3-[2'-(1H-tetrazol-5-yl)biphenyl-4-yl]methyl-1,3,4-thiadiazoline-2-yliden]aminosulfonyl]benzoic acid methyl ester [Compound No. 151]:
Property pale brown powder
$^1$H-NMR($\delta$ppm in CDCl$_3$)
8.14(2H,brs), 7.56(6H,brs), 7.33(2H,m), 7.08(2H,m), 5.27(2H,s), 3.82(3H,s), 2.84(2H,q), 1.32(3H,t)

Reference Example 4 cis-3,4,5,6-Tetrahydrophthalic acid monobenzyl ester (1.51 g) and benzylalcohol (1 ml) were added to tetrahydrofuran, and to the solution was added catalytic amount of 4-dimethylaminopyridine, then the mixture was refluxed for 6 hours. After cooling to room temperature, the solvent was evaporated in vacuo. The residue was partitioned between chloroform and aqueous 5% sodium hydroxide solution, then the aqueous layer was separated. With stirring, the aqueous layer was acidified with 20% hydrochloric acid solution on ice, and extracted with chloroform. The organic layer was dried over anhydrous magnesium sulfate and evaporated in vacuo. The title compound was obtained as a colorless oil (1.93 g).

Example 18

2-[[5-Ethyl-3-[2'-(1H-tetrazol-5-yl)biphenyl-4-yl]-methyl-1,3,4-thiadiazoline-2-yliden]aminocarbonyl]-1-cyclohxenecarboxylic acid benzyl ester [Compound No.152]:

(±)-cis-3,4,5,6-Tetrahydrophthalic acid monobenzyl ester (78 mg) was added to oxalyl chloride (1 ml), and the mixture was stirred for 10 minutes (until evolution of gas ceased). The solvent was evaporated in vacuo at room temperature and the residue was further dried under vacuo for 1 hour. The residue was dissolved in tetrahydrofuran (2 ml), then to the solution were added 2-imino-5-ethyl-3-[2'-(N-triphenylmethyltetrazol-5-yl)biphenyl-4-yl]methyl]-1,3,4-thiadiazoline (120 mg) and triethylsmine (3 drops), and the mixture was stirred at room temperature for 2 hours. To the mixture were added water and ethyl acetate followed by stirring. The organic layer was separated, dried over anhydrous magnesium sulfate, and evaporated in vacuo. The residue was purified by column chromatography on silica gel(eluent:chloroform/methanol=10/1). The resultant oily residue was dissolved in tetrahydrofuran (5 ml), to the solution was added to 20% hydrochloric acid solution (10 drops) followed by stirring for 20 hours at room temperature. The solvent was removed below 20° C., then the resultant solvent was further removed by azeotropic distillation of toluene twice. The residue was purified by column chromatography on silica gel (eluent:chloroform/methanol= 10/1) to give the title compound No.152 as a colorless powder(38 mg).
Property colorless powder
$^1$H-NMR($\delta$ppm in CDCl$_3$)
8.12(1H,d), 7.58(4H,m), 7.30–7.42(4H,m), 7.15–7.30 (4H,m), 5.40(2H,s), 5.06(2H,s), 2.85(2H,q), 2.34(4H,m), 1.71(4H,brs), 1.37(3H,t)

Example 19

Compounds Nos. 153–156 were synthesized in a similar manner to a example 18.

(1) cis-2-[[5-Ethyl-3-[2'-(1H-tetrazol-5-yl)biphenyl-4-yl]methyl-1,3,4-thiadiazoline-2-yliden]aminocarbonyl] cyclohexanecarboxylic acid benzylester [Compound No.153]:
Property colorless powder
$^1$H-NMR($\delta$ppm in CDCl$_3$)
8.06(2H,d), 7.52(4H,m), 7.10–7.37(7H,m), 5.30(2H,m), 5.00(2H,m), 3.06(1H,m), 2.96(1H,m), 2.89(2H,q), 1.98–2.22(2H,m), 1.82(2H,m), 1.42(4H,m), 1.35(3H,t)

(2) cis-2-[[5-Ethyl-3-[2'-(1H-tetrazol-5-yl)biphenyl-4-yl]methyl-1,3,4-thiadiazoline-2-yliden]aminocarbonyl] cyclohexanecarboxylic acid benzyl ester optical isomer A [Compound No.154]:
Property colorless powder
$^1$H-NMR($\delta$ppm in CDCl$_3$)
8.06(2H,d), 7.52(4H,m), 7.10–7.37(7H,m), 5.30(2H,m), 5.00(2H,m), 3.06(1H,m), 2.96(1H,m), 2.89(2H,q), 1.98–2.22(2H,m), 1.82(2H,m), 1.42(4H,m), 1.35(3H,t)

(3) cis-2-[[5-Ethyl-3-[2'-(1H-tetrazol-5-yl)biphenyl-4-yl]methyl-1,3,4-thiadiazoline-2-yliden]aminocarbonyl]-cyclohexanecarboxylic acid benzyl ester optical isomer B [Compound No. 155]:
Property colorless powder
$^1$H-NMR($\delta$ppm in CDCl$_3$)
8.06(2H,d), 7.52(4H,m), 7.10–7.37(7H,m), 5.30(2H,m), 5.00(2H,m), 3.06(1H,m), 2.96(1H,m), 2.89(2H,q), 1.98–2.22(2H,m), 1.82(2H,m), 1.42(4H,m), 1.35(3H,t)

(4) 2-[[5-Ethyl-3-[2'-(1H-tetrazol-5-yl)biphenyl-4-yl]-methyl-1,3,4-thiadiazoline-2-yliden]aminocarbonyl]-4-cyclohexenecarboxylic acid benzyl ester [Compound No.156]:
Property colorless powder
$^1$H-NMR($\delta$ppm in CDCl$_3$)
8.12(1H,d), 7.59(4H,m), 7.15–7.43(8H,m), 5.69(2H,m), 5.33(2H,dd), 5.16(1H,dd), 5.04(1H,dd), 3.11(2H,m), 2.86 (2H,q), 2.31–2.68(4H,m), 1.35(3H,t)

Example 20

2-[[5-Ethyl-3-[2'-(1H-tetrazol-5-yl)biphenyl-4-yl]methyl-1,3,4-thiadiazoline-2-yliden]aminocarbonyl]-1-cyclohxenecarboxylic acid [Compound No. 157]:

The compound No.152 (32 mg) obtained in example 18 was added to 25% hydrobromic acid in acetic acid solution (2 ml), then the mixture was stirred at 80° C. for 40 hours. After cooling on standing, the solvent was evaporated in vacuo at room temperature. To the residue was added ethyl acetate followed by stirring. The mixture was extracted with aqueous 5% sodium hydroxide solution for three times, and the aqueous layers were combined and washed with chloroform. With stirring, the aqueous layer was acidified with 20% hydrochloric acid solution on ice, and extracted with the mixed solvent of chloroform and tetrahydrofuran for three times. The organic layers were dried over anhydrous magnesium sulfate, and evaporated in vacuo. The residue was powdered from isopropyl ether, and the title compound No.154 was obtained as a pale red powder (11 mg).

Property pale red powder
$^1$H-NMR($\delta$ppm in CDCl$_3$)
7.81(1H,d), 7.32–7.53(3H,m), 7.11(2H,d), 7.00(2H,d), 5.52(2H,s), 2.88(2H,q), 2.38(4H,m), 1.72(4H,m), 1.32 (3H,t)

Example 21

Compounds Nos.158~161 were synthesized in a similar manner to example 20.

(1) cis-2-[[5-Ethyl-3-[2'-(1H-tetrazol-5-yl)biphenyl-4-yl]methyl-1,3,4-thiadiazoline-2-yliden]aminocarbonyl]-cyclohxanecarboxylic acid [Compound No. 158]:
Property pale orange powder
$^1$H-NMR($\delta$ppm in CDCl$_3$)
7.95(1H,s), 7.41–7.59(3H,m), 7.08–7.18(4H,m), 5.47 (2H,s), 3.01(1H,m), 2.89(1H,m), 2.86(2H,q), 2.09(1H,m), 1.81(2H,m), 1.42(5H,m), 1.35(3H,t)

(2) cis-2-[[5-Ethyl-3-[2'-(1H-tetrazol-5-yl)biphenyl-4-yl]methyl-1,3,4-thiadiazoline-2-yliden]aminocarbonyl]-cyclohxanecarboxylic acid optical isomer A [Compound No. 159]:
Property colorless powder
$^1$H-NMR($\delta$ppm in CDCl$_3$)
7.95(1H,s), 7.41–7.59(3H,m), 7.08–7.18(4H,m), 5.47 (2H,s), 3.01(1H,m), 2.89(1H,m), 2.86(2H,q), 2.09(1H,m), 1.81(2H,m), 1.42(5H,m), 1.35(3H,t)

(3) cis-2-[[5-Ethyl-3-[2'-(1H-tetrazol-5-yl)biphenyl-4-yl]methyl-1,3,4-thiadiazoline-2-yliden]aminocarbonyl]-cyclohxanecarboxylic acid optical isomer B [Compound No.160]:
Property colorless powder
$^1$H-NMR($\delta$ppm in CDCl$_3$)
7.95(1H,s), 7.41–7.59(3H,m), 7.08–7.18(4H,m), 5.47 (2H,s), 3.01(1H,m), 2.89(1H,m), 2.86(2H,q), 2.09(1H,m), 1.81(2H,m), 1.42(5H,m), 1.35(3H,t)

(4) 2-[[5-Ethyl-3-[2'-(1H-tetrazol-5-yl)biphenyl-4-yl]methyl-1,3,4-thiadiazoline-2-yliden]aminocarbonyl]-4-cyclohxenecarboxylic acid [Compound No. 161]:
Property pale brown powder
$^1$H-NMR($\delta$ppm in CDCl$_3$)
8.02(1H,s), 7.33–7.63(3H,m), 7.00–7.26(4H,m), 6.71 (2H,m), 5.40(2H,s), 3.27(4H,m), 3.07(1H,m), 2.80(1H,m), 2.86(2H,q), 1.35(3H,t)

Example 22

N-[5-Ethyl-3-[2'-(1H-tetrazol -5-yl)biphenyl-4-yl]methyl-1,3,4-thiadiazoline-2-yliden]phthalamic acid 2-methoxycarbonylbenzyl ester [Compound No.162]:

N-[5-Ethyl-3-[2'-(N-triphenylmethyltetrazol-5-yl)-biphenyl-4-yl]methyl-1,3,4-thiadiazoline-2-yliden]-phthalamic acid (30 mg) and 2-bromomethybenzoic acid methyl ester (12 mg) were added to N,N-dimethylformamide (0.5 ml), to the mixture was added cesium carbonate (30 mg). The mixture was stirred for 20 hours at room temperature. Water and ethyl acetate were added to the mixture followed by stirring for 30 minutes. The organic layer was separated, washed with water twice and dried over anhydrous magnesium sulfate. After removal of the solvent in vacuo, the residue was purified by column chromatography on silica gel (eluent:chloroform).

The resultant residue was dissolved in tetrahydrofuran (2 ml), then to the solution was added 20% hydrochloric acid solution (2 drops) followed by stirring for 20 hours at room temperature. The solvent was removed below 20° C., then the resultant solvent was further removed by azeotropic distillation of toluene twice. The residue was purified by column chromatography on silica gel (eluent:chloroform/methanol=10/1) to give the title compound No. 162 as a colorless powder (12 mg).

Property colorless powder
$^1$H-NMR($\delta$ppm in CDCl$_3$)
8.15(1H,d), 7.96(1H,d), 7.40–7.65(8H,m), 7.30–7.40(4H,d), 7.13–7.22.(2H,d), 5.61(2H,s), 5.53(2H,s), 4.08(3H,s), 2.91(2H,q), 1.37(3H,t)

Example 23

Compounds Nos.163~167 were synthesized in a similar manner to example 22.

(1) N-[5-Ethyl-3-[2'-(1H-tetrazol-5-yl)biphenyl-4-yl]methyl-1,3,4-thiadiazoline-2-yliden]phthalamic acid 2-carboxylic acid methyl ester [Compound No. 163]:
Property colorless powder
$^1$H-NMR($\delta$ppm in CDCl$_3$)
8.04(1H,d), 7.26–7.58(9H,m), 7.23(2H,m), 5.67(2H,s), 4.85(2H,s), 2.92(2H,q), 1.38(3H,m)

(2) N-[5-Ethyl-3-[2'-(1H-tetrazol-5-yl)biphenyl-4-yl]methyl-1,3,4-thiadiazoline-2-yliden]phthalamic acid 2-(1H-tetrazol-5-yl)benzylester [Compound No. 164]:
Property colorless powder
$^1$H-NMR($\delta$ppm in CDCl$_3$)
8.14(1H,d), 8.09(1H,d), 7.44–7.72(5H,m), 7.32–7.47(4H,d), 7.13–7.23(2H,d), 5.64(2H,s), 5.53(2H,s), 2.91(2H,q), 1.37(3H,t)

(3) N-[5-Ethyl-3-[2'-(1H-tetrazol-5-yl)biphenyl-4-yl]-methyl- 1,3,4-thiadiazoline-2-yliden]phthalamic acid butyl ester [Compound No. 165]:
Property colorless powder
$^1$H-NMR($\delta$ppm in CDCl$_3$)
8.12(1H,d), 7.93(1H,d), 7.43–7.63(5H,m), 7.32–7.43(3H,d), 7.13–7.22(2H,d), 5.52(2H,s), 4.17(2H,t), 2.91(2H,q), 1.60(2H,m), 1.37(3H,t), 1.29(2H,m), 0.86(3H,t)

(4) N-[5-Ethyl-3-[2'-(1H-tetrazol-5-yl)biphenyl-4-yl]-methyl-1,3,4-thiadiazoline-2-yliden]phthalamic acid propyl ester [Compound No. 166]:
Property colorless powder
$^1$H-NMR ($\delta$ppm in CDCl$_3$)
8.06(1H,d), 7.93(1H,d), 7.43–7.65(5H,m), 7.32–7.43(3H,d), 7.12–7.21(2H,d), 5.52(2H,s), 4.13(2H,t), 2.91(2H,q), 1.63(2H,m), 1.37(3H,t), 0.88 (3H,t)

(5) N-[5-Ethyl-3-[2'-(1H-tetrazol-5-yl)biphenyl-4-yl]-methyl-1,3,4-thiadiazoline-2-yliden]phthalamic acid benzyl ester [Compound No. 167]:
Property colorless powder
$^1$H-NMR($\delta$ppm in CDCl$_3$)

8.05(1H,d), 7.92(1H,d), 7.31–7.65(13H,m), 7.12–7.21 (2H,d), 5.52(2H,s), 5.44(2H,s), 2.89(2H,q), 1.39 (3H,t)

The prodrugs (example 24~example 27) of compound No.126 were synthesized as below.

Example 24

N-[5-Ethyl-3-[2'-(1H-tetrazol-5-yl)biphenyl-4-yl]methyl-1,3,4-thiadiazoline-2-yliden]phthalamic acid 5-methyl-2-oxo-1,3-dioxalane-4-methyl ester[Compound No.168]:

N-[[5-Ethyl-3-[2'-(N-triphenylmethyltetrazol-5-yl)-biphenyl-4-yl]methyl-1,3,4-thiadiazoline-2-yliden] phthalamic acid (75 mg) and 4-bromomethyl-5-methyl-2-oxa-1,3-dioxalane (50 mg) were added to N,N-dimethylformamide (2 ml), then to the solution was added potassium carbonate (30 mg). The mixture was stirred for 4 hours at 90° C. After cooling, water and ethyl acetate were added to the mixture followed by stirring for 30 minutes. The organic layer was separated and the aqueous layer was extracted with ethyl acetate twice. The organic layer was combined, washed with water twice and dried over anhydrous magnesium sulfate. After removal of the solvent in vacuo, the residue was purified by column chromatography on silica gel (eluent:chloroform). The resultant residue was dissolved in tetrahydrofuran (5 ml), then to the solution was added 20% hydrochloric acid solution (5 drops) followed by stirring for 20 hours at room temperature. The solvent was removed below 20° C., then the resultant solvent was further removed by azeotropic distillation of toluene twice. The residue was purified by column chromatography on silica gel (eluent:chloroform) to give the title compound No.168 as a colorless powder (12 mg).

Property colorless powder $^1$H-NMR($\delta$ppm in CDCl$_3$)

8.18(1H,d), 8.12(1H,d), 7.37–7.79(6H,m), 7.21–7.36(4H, m), 5.58(2H,s), 4.98(2H,s), 2.93(2H,q), 2.21(3H,s), 1.37 (3H,t)

Example 25

N-[5-Ethyl-3-[2'-(1H-tetrazol-5-yl)biphenyl-4-yl]-methyl-1,3,4-thiadiazoline-2-yliden]phthalamic acid phthalidyl ester [Compound No. 169]:

N-[5-Ethyl-3-[2'-(N-triphenylmethyltetrazol-5-yl)-biphenyl-4-yl]methyl-1,3,4-thiadiazoline-2-yliden]-phthalamic acid (75 mg) and α-bromophthalidyl (100 mg) were added to N,N-dimethylformamide (2 ml), to the solution was added potassium carbonate (30 mg). The mixture was stirred for 4 hours at 90° C. After cooling, water and ethyl acetate were added to the mixture followed by stirring for 30 minutes. The organic layer was separated and the aqueous layer was extracted with ethyl acetate twice. The organic layer was combined, washed with water twice and dried over anhydrous magnesium sulfate. After removal of the solvent in vacuo, the residue was purified by column chromatography on silica gel (eluent:chloroform).

The resultant oily residue was dissolved in tetrahydrofuran (5 ml), then to the solution was added 20% hydrochloric acid solution (5 drops) followed by stirring for 20 hours at room temperature. The solvent was removed below 20° C., then the resultant solvent was further removed by azeotropic distillation of toluene twice. The residue was purified by column chromatography on silica gel (eluent:chloroform) to give the title compound No.169 as a colorless powder (46 mg).

Property colorless powder $^1$H-NMR($\delta$ppm in CDCl$_3$)

8.13(1H,d), 7.95(1H,d), 7.82(1H,d), 7.26–7.80(12H,m), 7.23(2H,d), 5.59(2H,s), 2.91(2H,q), 1.40(3H,t)

Example 26

N-[5-Ethyl-3-[2'-(1H-tetrazol-5-yl)biphenyl-4-yl]methyl-1,3,4-thiadiazoline-2-yliden]phthalamic acid 1-(ethoxycarbonyloxy) ethyl ester [Compound No. 170]:

N-[5-Ethyl-3-[2'-(N-triphenylmethyltetrazol-5-yl)-biphenyl-4-yl]methyl-1,3,4-thiadiazoline-2-yliden] phthalamic acid (75 mg) and cesium carbonate (60 mg) were added to N,N-dimethylformamide (0.5 ml). With stirring, to the mixture was added 1-chloroethylethylcarbonate (23 mg) at room temperature. The mixture was stirred for 1 hour, water and ethyl acetate were added to the mixture followed by stirring. The organic layer was separated, washed with water twice and dried over anhydrous magnesium sulfate. After removal of the solvent in vacuo, the residue was purified by column chromatography on silica gel (eluent:chloroform).

The resultant oily residue was dissolved in tetrahydrofuran (5 ml), then to the solution was added 20% hydrochloric acid solution (5 drops) followed by stirring for 20 hours at room temperature. The solvent was removed below 20° C., then the resultant solvent was further removed by azeotropic distillation of toluene twice. The residue was purified by column chromatography on silica gel (eluent:chloroform/methanol=20/1) to give the title compound No.170 as a colorless powder (24 mg).

Example 27

Compound Nos.171~177 were synthesized in a similar manner to example 26.

(1) N-[5-Ethyl-3-[2'-(1H-tetrazol-5-yl)biphenyl-4-yl]-methyl-1,3,4-thiadiazoline-2-yliden]phthalamic acid pivaloyloxymethyl ester [Compound No.171]:

Property colorless powder $^1$H-NMR($\delta$ppm in CDCl$_3$)

8.04(1H d), 7.90(1H d), 7.33–7.79(8H m), 7.21(2H d), 5.88 (2H s), 5.54 (2H dd), 2.93 (2H q), 1.28 (3H t), 1.14 (9H s)

(2) N-[5-Ethyl-3-[2'-(1H-tetrazol-5-yl)biphenyl-4-yl]-methyl-1,3,4- thiadiazoline-2-yliden]phthalamic acid ethoxycarbonylmethylester [Compound No. 172]:

Property colorless powder $^1$H-NMR ($\delta$ppm in CDCl$_3$)

7.95–8.10 (2H m), 7.48–7.90 (4H m), 7.44 (4H d), 7.23(2H d), 5.53(2H dd), 4.72(2H s), 4.15(2H q), 2.87 (2H q), 1.38 (3H t), 1.24 (3H t)

(3) N-[5-Ethyl-3-[2'-(1H-tetrazol-5-yl)biphenyl-4-yl] methyl-1,3,4-thiadiazoline-2-yliden]phthalamic acid tert-butyloxycarboxylic acid methyl ester [Compound No.173]:

Property colorless powder $^1$H-NMR($\delta$ppm in CDCl$_3$)

7.90–8.00(2H m), 7.49–7.90(4H m), 7.44(4H d), 7.25(2H d), 5.53(2H dd), 4.70(2H s), 2.87(2H q) 1.49(9H s), 1.38 (3H,t)

(4) N-[5-Ethyl-3-[2'-(1H-tetrazol-5-yl)biphenyl-4-yl]-methyl-1,3,4-thiadiazoline-2-yliden]phthalamic acid 1-(methoxycarbonyloxy)ethyl ester [Compound No. 174]:

Property colorless powder $^1$H-NMR($\delta$ppm in CDCl$_3$)

8.03 (1H d), 7.99(1H d), 7.43–7.69 (4H d), 7.42 (4H d), 7.20 (2H d), 6.69(1H m), 5.54 (2H dd), 3.95(3H s), 2.91 (2H q), 1.41 (3H t), 1.31 (3H d)

(5) N-[5-Ethyl-3-[2'-(1H-tetrazol-5-yl)biphenyl-4-yl]-methyl-1,3,4-thiadiazoline-2-yliden]phthalmmic acid 1-(tert-butyloxycarbonyloxy)ethyl ester [Compound No.175]:

Property colorless powder
¹H-NMR(δppm in CDCl₃)
8.04(1H,d), 7.92(1H,d), 7.33–7.77(8H,m), 7.21(2H,d), 6.63(1H,q), 5.54(2H,dd), 2.93(2H,q), 1.34–1.48 (15H,m)

(6) N-[5-Ethyl-3-[2'-(1H-tetrazol-5-yl)biphenyl-4-yl]-methyl-1,3,4-thiadiazoline-2-yliden]phthalamic acid 1-(cyclohexyloxycarbonyloxy)ethyl ester [Compound No. 176]:
Property colorless powder
¹H-NMR(δppm in CDCl₃)
8.03 (1H,d), 7.94 (1H,d), 7.45–7.69(4H,d), 7.44(4H,d), 7.23(2H,d), 6.69(1H,m), 5.53(2H,dd), 4.49(1H,m), 2.91(2H, q), 1.19–1.92(16H,m)

(7) N-[5-Ethyl-3-[2'-(1H-tetrazol-5-yl)biphenyl-4-yl]-methyl-1,3,4-thiadiazoline-2-yliden]phthalamic acid 1-(cycloheptyloxycarbonyloxy)ethyl ester [Compound No. 177]:
Property colorless powder
¹H-NMR(δppm in CDCl₃)
8.04 (1H d), 7.95(1H d), 7.42–7.69(4H d), 7.41 (4H d), 7.21 (2H d), 6.68 (1H m), 5.51 (2H dd), 4.49 (1H m), 2.90 (2H q), 1.19–1.99 (18H m)

Example 28

Prodrugs of compound No.130 obtained in example 17 (4) were synthesized in a similar manner to example 26.

(1) 2-[[5-Ethyl-3-[2'-(1H-tetrazol-5-yl)biphenyl-4-yl]-methyl-1,3,4-thiadiazoline-2-yliden]aminocarbonyl]-1-cyclopentencarboxylic acid pivaloyloxymethyl ester Compound No. 178]:
Property colorless powder
¹H-NMR(δppm in CDCl₃)
7.98(2H,d), 7.31–7.62 (4H ,m), 7.20 (2H, d), 5.66(2H,S), 5.48 (2H,S), 2.71–2.92 (6H,m), 2.05 (2H, t), 1.33(3H,t), 1.18(9H,S)

(2) 2-[[5-Ethyl-3-[2'-(1H-tetrazol-5-yl)biphenyl-4-yl]methyl-1,3,4-thiadiazoline-2-yliden]aminocarbonyl]-1-cyclopenten carboxylic acid
1-(ethoxycarbonyloxy)ethyl ester [Compound No. 179]:
Property colorless powder
¹H-NMR(δppm in CDCl₃)
8.02(2H,m), 7.30–7.66(4H,m), 7.20(2H,d), 6.68(1H,q), 5.45(2H,dd), 4.14(2H,q), 2.73–2.92(6H,m), 2.04 (2H,t), 1.43(6H,m), 1.35(3H,t)

(3) 2-[[5-Ethyl-3-[2'-(1H-tetrazol-5-yl)biphenyl-4-yl] methyl-1,3,4-thiadiazoline-2-yliden]aminocarbonyl]-1-cyclopenten carboxylic acid
1-(tert-butyloxycarbonyloxy)ethyl ester [Compound No. 180]:
Property colorless powder
¹H-NMR(δppm in CDCl₃)
8.02(2H,m), 7.30–7.66(4H,m), 7.20(2H,d), 6.68(1H,q), 5.45(2H,dd), 2.73–2.92(6H,m), 2.04(2H,t), 1.35–1.42 (15H, m)

(4) 2-[[5-Ethyl-3-[2'-(1H-tetrazol-5-yl)biphenyl-4-yl] methyl-1,3,4-thiadiazoline-2-yliden]aminocarbonyl]-1-cyclopenten carboxylic acid 1-(cyclohexyloxycarbonyloxy) ethyl ester [Compound No. 181]:
Property colorless powder
¹H-NMR (δppm in CDCl₃)
8.00(2H,m), 7.30–7.68(4H,m), 7.22(2H,d), 6.68(1H,q), 5.46(2H,dd), 4.51(1H,m), 2.71–2.92(6H,m), 2.04(2H,t), 1.48–1.96(6H,m), 1.45(3H,d), 1.00–1.44(7H,m)

Example 29

Prodrugs of compound No.132 obtained in example 17(6) were synthesized in a similar manner to example 27.

(1) 2-[[5-Cyclopropyl-3-[2'-(1H-tetrazol-5-yl)biphenyl-4-yl]methyl-1,3,4-thiadiazoline-2-yliden]aminocarbonyl]-1-cyclopentene carboxylic acid pivaloyloxymethyl ester [Compound No. 182]:
Property colorless powder
¹H-NMR(δppm in CDCl₃)
7.99(2H,d), 7.31–7.67(4H,m), 7.20(2H,d), 5.68(2H,S), 5.50(2H,S), 2.71–2.92(4H,m), 2.16(1H,m), 2.05(2H,t), 0.99–1.45 (13H,m)

(2) 2-[[5-Cyclopropyl-3-[2'-(1H-tetrazol-5-yl)biphenyl-4-yl]methyl-1,3,4-thiadiazoline-2-yliden]aminocarbonyl]-1-cyclopenten carboxylic acid 1-(ethoxycarbonyloxy)ethyl ester [Compound No. 183]:
Property colorless powder
¹H-NMR(δppm in CDCl₃)
8.05(2H,m), 7.31–7.59(4H,m), 7.20(2H,d), 6.66(1H,q), 5.46(2H,dd), 4.14(2H,q),2.82(4H,m), 2.16(1H,m), 2.06(2H, t), 1.00–1.42(10H,m)

(3) 2-[[5-Cyclopropyl-3-[2'-(1H-tetrazol-5-yl)biphenyl-4-yl]methyl-1,3,4-thiadiazoline-2-yliden]aminocarbonyl]-1-cyclopentenecarboxylic acid1-(tert-butyloxycarbonyloxy)-ethyl ester [Compound No. 184]:
Property colorless powder
¹H-NMR(δppm in CDCl₃)
8.05(2H,m), 7.31–7.62(4H,m), 7.22(2H,d), 6.66(1H,q), 5.46(2H,dd), 2.82(4H,m), 2.16(1H,m), 2.06(2H,t), 1.43 (12H,m), 1.00–1.42(4H,m)

(4) 2-[[5-Cyclopropyl-3-[2'-(1H-tetrazol-5-yl)biphenyl-4-yl]methyl-1,3,4-thiadiazoline-2-yliden]aminocarbonyl]-1-cyclopentenecarboxylic acid 1-(tert-butyloxycarbonyloxy)-ethyl ester [Compound No. 185]:
Property colorless powder
¹H-NMR(δppm in CDCl₃)
8.03(2H,m), 7.31–7.64(4H,m), 7.22(2H,d), 6.68(1H,q), 5.46(2H,dd), 4.51(1H,m), 2.80(4H,m), 2.16(1H,m), 2.04 (2H,t), 1.48–1.93(6H,m), 1.45(3H,d), 1.00–1.44 (8H,m)

The synthetic methods of thiadiazoline derivatives by preferable Preparation Process 2 in the present invention, were described as below (example 31–example 32) .

[Syntheses of thiadiazoline derivatives ]

Reference Example 5

2-t-Butyloxycarbonylamino-5-ethyl-1,3,4-thiadiazole

2-Amino-5-ethyl-1,3,4-thiadiazole (3.88 g) and di-t-butyldicarbonate (7.19 g) were added to N,N-dimethylformamide (120 ml). To the solution was added catalytic amount of 4-dimethylaminopyridine followed by stirring at 60° C. for 12 hours. After cooling, water (200 ml) was added with vigorously stirring. The mixture was further stirred for 30minutes. The precipitated crystals were filtrated and dried. The title compound was obtained as colorless crystals (12 g).

Property colorless crystals
Melting point 108°–112° C.
¹H-NMR(δppm in CDCl₃)
3.02(2H,q), 1.56(9H,s), 1.40(3H,t)

Reference Example 6

2-[N-(2'-(1H-tetrazol-5-yl)biphenyl-4-yl)methyl]amino-5-ethyl-1,3,4-thiadiazole

To a suspension of potassium carbonate (600 mg) in N,N-dimethylformamide (30 ml) were added 2-t-butyloxycarbonylamino-5-ethyl-1,3,4-thiazole (687 mg) and 4'-bromomethyl-2-(N-triphenylmethyltetrazol-5-yl)-biphenyl (1.67 g), then the mixture was stirred at 60° C. on oil bath for 6 hours. After cooling, water and ethyl acetate were added to the mixture. The organic layer was separated, washed with water and dried over anhydrous magnesium sulfate. The magnesium sulfate was removed by filtration and the filtrate was evaporated. The residue was purified by column chromatography on silica gel (eluent:chloroform). The fractions containing pure title compound were collected and the solvent was removed. 4N Hydrochloric acid in dioxane (30 ml) was added to the residue, and the mixture was stirred for 20 hours at room temperature. After removal of the solvent, the precipitate was washed with ether by decantation twice. The glassy precipitate was dispersed with ether and filtrated. The precipitate was dried to give the title compound (560 mg).

Property colorless powder $^1$H-NMR($\delta$ppm in CDCl$_3$)

7.81(1H,d), 7.49–7.68(3H,m), 7.35(2H,m), 7.17(2H,d), 4.56(2H,s), 2.94(2H,q), 1.37(3H,t)

Reference Example 7

2-[N-(2'-(N-Triphenylmethyltetrazol-5-yl)biphenyl-4-yl) methyl]amino-5-ethyl-1,3,4-thiadiazole 2-[N-(2'-(1H-tetrazol-5-yl)biphenyl-4-yl)methyl]amino-5-ethyl-1,3,4-thiadiazole (560 mg) was added to the mixed solvent of tetrahydrofuran (20 ml) and N,N-dimethylformamide (10 ml). To the solution was added trytyl chloride (431 mg) and triethylamine (155 mg) with stirring at room temperature. After stirring for 20 hours at room temperature, water and ethyl acetate were added to the mixture. The organic layer was separated, washed with water and dried over anhydrous magnesium sulfate. The magnesium sulfate was removed by filtration and the filtrate was evaporated. The residue was purified by column chromatography on silica gel (eluent:chloroform). The main fractions containing title compound were collected and the solvent was evaporated. The precipitated crystals were filtrated and dried to give the title compound(606 mg).

Property colorless crystals

Melting point 160°–162° C.

$^1$H-NMR($\delta$ppm in CDCl$_3$)

7.97(1H,d), 7.49(2H,m), 7.22–7.41(11H,m), 7.06(3H,.d), 6.87(6H,d), 4.40(2H,s), 2.89(2H,q), 1.34(3H,t)

Example 30

2-[N-(2-Chlorobenzoyl)-N-(2'-(1H-tetrazol-5-yl) biphenyl-4-yl)methyl]amino-5-ethyl-1,3,4-thiadiazole [Compound No.186]:

To a suspension of sodium hydride (4 mg, 55% in oil) in N,N-dimethylformamide (0.5 ml) was added 2-[N-(2'-(N-triphenylmethyltetrazol-5-yl)biphenyl-4-yl)methyl]amino-5-ethyl-1,3,4-thiadiazole (60 mg) at room temperature. When evolution of hydrogen ceased, 2-chlorobenzoyl chloride (18 mg) was added. After stirring for 20 hours, water and ethyl acetate were added to the mixture. The organic layer was separated, washed with water and dried over anhydrous magnesium sulfate. The magnesium sulfate was removed by filtration and the filtrate was evaporated. The residue was separated by column chromatography on silica gel (eluent:chloroform) The fractions containing main product were collected and the solvent was evaporated.

To the residue were added tetrahydrofuran (3 ml) and 20% hydrochloric acid solution (0.1 ml), and the mixture was stirred for 1 hour at room temperature. The reaction mixture was made basic with 5% aqueous sodium hydroxide solution. The aqueous layer was washed with ether and neutralized with 20% hydrochloric acid solution and then extracted with the mixed solvent of chlroform and tetrahydrofuran. The organic layer was separated, washed with water and dried over anhydrous magnesium sulfate. The magnesium sulfate was removed by filtration and the filtrate was evaporated. The resultant oil crystallized on standing. Ether was added and the crystals were filtrated and dried. The title compound No. 186 was obtained as colorless crystals(15 mg).

Property colorless crystals

Melting point 228°–231° C.

$^1$H-NMR($\delta$ppm in CDCl$_3$)

8.05(1H,d), 7.32–7.58(5H,m), 7.07(3H,bs), 5.54(1H,d), 5.11(1H,d), 3.10(2H,q), 1.45(3H,t)

Example 31

Compounds Nos.187~204 were synthesized in a similar manner to example 30.

(1) 2-[N-t-Butyloxycarbonyl-N-(2'-(1H-tetrazol-5-yl)-biphenyl-4-yl)methyl]amino-5-ethyl-1,3,4-thiadiazole [Compound No. 187]:

Property colorless powder $^1$H-NMR($\delta$ppm in CDCl$_3$)

7.86(1H,d), 7.40–7.49(2H,m), 7.22–7.37(3H,m), 7.08 (2H,d), 5.23(2H,d), 3.00(2H,q), 1.47(9H,s), 1.39(3H,t)

(2) 2-[N-(2,6-Dichlorobenzoyl) -N-(2'-(1H-tetrazol-5-yl) biphenyl-4-yl) methyl]amino-5-ethyl-1,3,4-thiadiazole [Compound No. 188]:

Property colorless powder $^1$H-NMR($\delta$ppm in CDCl$_6$)

8.08(1H,d), 7.32–7.54(7H,m), 7.05(3H,m), 5.57(1H,d), 5.13(1H,d), 3.10(2H,q), 1.45(3H,t)

(3) 2-[N-Ethoxycarbonyl-N-(2'-(1H-tetrazol-5-yl)-biphenyl-4-yl)methyl]amino-5-ethyl-1,3,4-thiadiazole [Compound No. 189]:

Property colorless powder $^1$H-NMR($\delta$ppm in CDCl$_3$+CD$_3$OD)

7.88(1H,d), 7.41–7.65(3H,m), 7.29(2H,m), 7.11(2H,m), 5.33(2H,d), 4.37(2H,q), 3.03(2H,q), 1.39(3H,t), 1.33 (3H,t)

(4) 2-[N-(2,4-Dinitrophenyl)-N-(2'-(1H-tetrazol-5-yl)-biphenyl-4-yl)methyl]amino-5-ethyl-1,3,4-thiadiazole [Compound No. 190]:

Property yellow crystals

Melting point 155°–161° C.

$^1$H-NMR($\delta$ppm in CDCl$_3$)

8.79(1H,d), 8.48(1H,d), 7.93(1H,d), 7.46–7.65(4H,m), 7.16–7.44 (2H,m), 7.11 (2H,m), 5.12(2H,d), 2.93(2H,q), 1.32 (3H, t)

(5) 2-[N-Benzyl-N-(2'-(1H-tetrazol-5-yl)biphenyl-4-yl)-methyl]amino-5-ethyl-1,3,4-thiadiazole [Compound No. 191]:

Property colorless powder $^1$H-NMR($\delta$ppm in CDCl$_3$)

7.98(1H,d), 7.43–7.60(3H,m), 7.22–7.42(5H,m), 7.20 (2H,d), 7.12(2H,d), 4.64(2H,s), 4.62(2H,s), 2.87(2H,q), 1.30 (3H,t)

(6) 2-[N-(4-Morpholinocarbonyl)-N-(2'-(1H-tetrazol-5-yl) biphenyl-4-yl)methyl]amino-5-ethyl-1,3,4-thiadiazole [Compound No. 192]:

Property colorless powder $^1$H-NMR($\delta$ppm in CDCl$_3$)

8.00(1H,d), 7.46–7.60(2H,m), 7.42(1H,d), 7.28(2H,d), 7.13(2H,d), 5.12(2H,s), 3.66(4H,t), 3.42(4H,t), 2.98 (2H,q) ,1.36 (3H,t)

(7) 2-[N-Phenacyl-N-(2'-(1H-tetrazol-5-yl)biphenyl-4-yl) mrthyl]amino-5-ethyl-1,3,4-thiadiazole [Compound No.193]:

Property colorless powder
$^1$H-NMR($\delta$ppm in CDCl$_3$)
7.92(1H,d), 7.19–7.60(10H,m), 7.16(1H,d), 7.06(1H,d), 4.95(2H,s), 4.73(2H,s), 2.85(2H,q), 1.29(3H,t)

(8) 2-[N-Benzyloxycarbonyl-N-(2'-(1H-tetrazol-5-yl)-biphenyl-4-yl)methyl]amino-5-ethyl -1,3,4-thiadiazole [Compound No. 194]:
Property colorless powder
$^1$H-NMR($\delta$ppm in CDCl$_3$)
8.04(1H,d), 7.94(1H,d), 7.44–7.58(2H,m), 7.18–7.44(7H,m), 7.08(2H,d), 5.32(2H,s), 4.40(2H,s), 2.97(2H,q), 1.35 (3H,t)

(9) 2-[N-n-Butyl-N-(2'-(1H-tetrazol-5-yl)biphenyl-4-yl) methyl]amino-5-ethyl-1,3,4-thiadiazole [Compound No.195]:
Property pale yellow powder
$^1$H-NMR($\delta$ppm in CDCl$_3$)
7.89(1H,dd), 6.96–7.69(7H,m), 4.62(2H,s), 3.37(2H,t), 2.86(4H,q), 1.66(2H,m), 1.35(3H,t), 0.94(3H,t)

(10) 2-[N-(3-Chloro-2-thenoyl)-N-(2'-(1H-tetrazol-5-yl) biphenyl-4-yl)methyl]amino-5-ethyl-1,3,4-thiadiazole [Compound No. 196]:
Property colorless powder
$^1$H-NMR($\delta$ppm in CDCl$_3$+CD$_3$OD)
7.87(1H,d), 7.37–7.62(5H,m), 7.29(2H,m), 7.12(2H,m), 4.47(2H,s), 2.92(2H,q), 1.32(3H,t)

(11) 2-[N-(2-Chloronicotinoyl)-N-(2'-(1H-tetrazol-5-yl) biphenyl-4-yl)methyl]amino-5-ethyl-1,3,4-thiadiazole [Compound No. 197]:
Property colorless powder
$^1$H-NMR($\delta$ppm in CDCl$_3$)
8.48(2H,m), 7.82–8.00(2H,m), 6.82–6.61(7H,m), 5.36 (1H,d), 5.08(1H,d), 2.92(2H,q), 1.33(3H,t)

(12) 2-[N-(4-Methyl-1,2,3-thiadiazole-5-carbonyl)-N-(2'-(1H-tetrazol-5-yl)biphenyl-4-yl)methyl]amino-5-ethyl-1,3, 4-thiadiazole [Compound No. 198]:
Property colorless powder
$^1$H-NMR ($\delta$ppm in CDCl$_3$+CD$_3$OD)
7.82(1H,d), 7.41–7.63(4H,m), 7.28(1H,m), 7.14(2H,d), 5.39(1H,d), 5.14(1H,d), 2.93(2H,q), 2.53(3H,s), 1.35 (3H,t)

(13) 2-[N-(2-Cyanophenyl)-N-(2'-(1H-tetrazol-5-yl)-biphenyl-4-yl)methyl]amino-5-ethyl-1,3,4-thiadiazole [Compound No. 199]:
Property yellow powder
$^1$H-NMR($\delta$ppm in CDCl$_3$+CD$_3$OD)
8.23(1H,d), 7.82(1H,d), 7.36–7.69(4H,m), 7.10–7.32(6H, m), 5.58(1H,d), 5.14(1H,d), 2.86(2H,q), 2.53(3H,s), 1.42 (3H,t)

(14) 2-[N-(2-Methoxycarbonylbenzyl)-N-(2'-(1H-tetrazol-5-yl)biphenyl-4-yl)methyl]amino-5-ethyl-1,3,4-thiadiazole [Compound No. 200]:
Property colorless powder
$^1$H-NMR($\delta$ppm in CDCl$_3$)
8.16(1H,d), 7.99(1H,d), 7.49–7.61(3H,m), 7.35–7.46(3H, m), 7.10–7.32(4H,m), 5.06(2H,s), 4.76(2H,s), 3.82(3H,s), 2.93(2H,q), 1.34(3H,t)

(15) 2-[N-(1H-tetrazol-5-yl)benzyl)-N-(2'-(1H-tetrazol-5-yl)biphenyl-4-yl)methyl]amino-5-ethyl-1,3,4-thiadiazole [Compound No. 201]:
Property pale yellow powder
$^1$H-NMR($\delta$ppm in CDCl$_3$)
7.83(2H,d), 7.24–7.57(6H,m), 6.83(2H,d), 6.72(2H,d), 5.00(2H,s), 4.50(2H,s), 2.94(2H,q), 1.34(3H,t)

(16) 2-[N-(2-Carboxybenzyl)-N-(2'-(1H-tetrazol-5-yl)-biphenyl-4-yl)methyl]amino-5-ethyl-1,3,4-thiadiazole [Compound No. 202]:
Property pale yellow powder
$^1$H-NMR($\delta$ppm in CDCl$_3$+CD$_3$OD)
7.92(2H,d), 7.40–7.65(4H,m), 7.11–7.39(6H,m), 5.18 (2H,s), 4.82(2H,s), 2.96(2H,q), 1.35(3H,t)

(17) 2-[N-(3-Methoxycarbonylbenzyl)-N-(2'-(1H-tetrazol-5-yl)biphenyl-4-yl) methyl]amino-5-ethyl-1,3,4-thiadiazole [Compound No. 203]:
Property pale yellow powder
$^1$H-NMR($\delta$ppm in CDCl$_3$)
7.96(2H,m), 7.37–7.67(5H,m), 7.08–7.35(5H,m), 4.73 (2H,s), 4.71(2H,s), 2.89(2H,q), 3.87(3H,s), 1.33 (3H,t)

(18) 2-[N-(3-Carboxybenzyl)-N-(2'-(1H-tetrazol-5-yl)-biphenyl-4-yl)methyl]amino-5-ethyl-1,3,4-thiadiazole [Compound No. 204]:
Property pale yellow powder
$^1$H-NMR($\delta$ppm in CDCl$_3$+CD$_3$OD)
8.00(1H,d), 7.86(1H,m), 7.39–7.62(6H,m), 7.10–7.21 (4H,m), 4.68(4H,brs), 2.92(2H,q), 1.33 (3H,t)

Synthetic methods (Preparation Process 2) of sulfonylimi-nothiadiazoline derivatives were described as below (example 32~33).

Example 32

2-(2-Chlorobenzenesulfonyl)imino-5-ethyl-3-[2'-(1H-tetrazol-5-yl)biphenyl-4-yl ]methyl-1,3,4-thiadiazoline [Compound No. 205]:

2-Imino-5-ethyl-3-[2'-(N-triphenylmethyltetrazol-5-yl) biphenyl-4-yl]methyl-1,3,4-thiadiazoline (60 mg), 2-chlorobenzenesulfonylchloride (21 mg) and triethylamine (11 mg) were added to N,N-dimethylformamide (0.5 m). After stirring for 20 hours, water and ethyl acetate were added to the mixture. The organic layer was separated, washed with water and dried over anhydrous magnesium sulfate. The magnesium sulfate was removed by filtration and the filtrate was evaporated. The residue was separated by column chromatography on silica gel (eluent:chloroform) The fractions containing main product were collected and the solvent was evaporated.

To the residue were added tetrahydrofuran (3 ml) and 20% hydrochloric acid solution (0.1 ml) followed by stirring at room temperature. After stirring for 20 hours, the reaction mixture was made basic with 5% aqueous sodium hydroxide solution. The aqueous layer was washed with ether, neutralized with 20% hydrochloric acid solution, and extracted with the mixed solvent of chloroform and tetrahydrofuran. The organic layer was separated, washed with water and dried over anhydrous magnesium sulfate. The magnesium sulfate was removed by filtration and the filtrate was evaporated. The residue was powdered from ether, and the powder was filtrated and dried. The title compound No.205 was obtained as a pale yellow powder (12 mg).

Property pale yellow powder
$^1$H-NMR ($\delta$ppm in CDCl$_3$)
8.18(1H,d), 8.05(1H,d), 7.51–7.61(2H,m), 7.26–7.60(6H, m), 7.11(2H,d), 5.26(2H,s), 2.86(2H,q), 1.35 (3H,t)

Example 33

Compounds Nos.206~210 were synthesized in a similar manner to example 32.

(1) 2-Ethanesulfonylimino-5-ethyl-3-[2'-(1H-tetrazol-5-yl) biphenyl-4-yl]methyl-1,3,4-thiadiazoline [Compound No.206]:
Property colorless powder
$^1$H-NMR($\delta$ppm in CDCl$_3$)
7.93 (1H,d), 7.32–7.61(3H,m), 7.26(2H,d), 7.11(2H,d), 5.23(2H,s), 3.09(2H,q), 2.82(2H,q), 1.33(3H,t), 1.30 (3H,t)

(2) 2-Benzenesulfonylimino-5-ethyl-3-[2'-(1H-tetrazol-5-yl)biphenyl-4-yl]methyl-1,3,4-thiadiazoline [Compound No.207]:

Property colorless powder
$^1$H-NMR($\delta$ppm in CDCl$_3$)
6.90–7.92(13H,m), 5.18(2H,s), 2.80(2H,q), 1.28(3H,t)

(3) 2-(4-Toluenesulfonyl)imino-5-ethyl-3-[2'-(1H-tetrazol-5-yl)biphenyl-4-yl]methyl-1,3,4-thiadiazoline [Compound No. 208]:

Property colorless powder
$^1$H-NMR($\delta$ppm in CDCl$_3$)
6.90–7.92(12H,m), 5.14(2H,s), 2.72(2H,q), 2.37(3H,s), 1.26(3H,t)

(4) 2-(2-Carboxylthiophene-3-sulfonyl)imino-5-ethyl-3-[2'-(1H-tetrazol-5-yl)biphenyl-4-yl]methyl-1,3,4-thiadiazoline [Compound No. 209]:

Property colorless powder
$^1$H-NMR($\delta$ppm in CDCl$_3$)
7.87(1H,d), 7.39–7.70(5H,m), 7.02–7.15(4H,d), 5.25(2H, s), 2.82(2H,q), 1.32(3H,t)

(5) 2-(2-Methoxycarbonylbenzenesulfonyl)imino-5-ethyl-3-[2'-(1H-tetrazol-5-yl)biphenyl-4-yl]methyl-1,3,4-thiadiazoline [Compound No. 210]:

Property colorless powder
$^1$H-NMR($\delta$ppm in CDCl$_3$)
8.18(2H,m), 7.18–7.70(8H,m), 7.12(2H,d), 5.31(2H,s), 3.81(3H,s), 2.87(2H,q), 1.34(3H,t)

Synthetic methods (Preparation Process 2) of sulfonylaminothiadiazole derivatives were described as below (example 34–35).

Example 34

2-[N-(2-Cyanobenzenesulfonyl)-N-(2'-(1H-tetrazol-5-yl)biphenyl-4-yl)methyl]amino-5-ethyl-1,3,4-thiadiazole [Compound No. 211]:

To a suspension of sodium hydride (4 mg, 55% in oil) in N,N-dimethylformamide (0.5 ml) was added 2-[N-(2 '-(N-Triphenylmethyltetrazol-5-yl)biphenyl-4-yl)methyl]amino-5-ethyl-1,3,4-thiadiazole (60 mg) at room temperature. When evolution of hydrogen ceased, 2-cyanobenzensulfonyl chloride (20 mg) was added to the mixture. After stirring for 20 hours at room temperature, water and ethyl acetate were added to the mixture. The organic layer was separated, washed with water and dried over anhydrous magnesium sulfate. The magnesium sulfate was removed by filtration and the filtrate was evaporated. The residue was separated by column chromatography on silica gel (eluent:chloroform). The fractions containing main product were collected and the solvent was evaporated.

To the residue were added tetrahydrofuran (3 ml) and 20% hydrochloric acid solution (0.1 ml) followed by stirring at room temperature. After stirring for 20 hours, the reaction mixture was made basic with 5% aqueous sodium hydroxide solution. The aqueous layer was washed with ether, neutralized with 20% hydrochloric acid solution, and extracted with the mixed solvent of chloroform and tetrahydrofuran. The organic layer was separated, washed with water and dried over anhydrous magnesium sulfate. The magnesium sulfate was removed by filtration and the filtrate was evaporated. The residue was powdered from ether, and the powder was filtrated and dried. The title compound No.211 was obtained as a pale yellow powder (16 mg).

Property pale yellow powder
$^1$H-NMR($\delta$ppm in CDCl$_3$)
8.14(2H,m), 7.91(1H,m), 7.81(2H,m), 7.57(2H,m), 7.44 (3H,m), 7.19(2H,d), 5.38(2H,s), 3.01(2H,q), 1.39 (3H, t)

Example 35

Compounds Nos.212–216 were synthesized in a similar manner to example 34.

(1) 2-[N-(2-Fluorobenzenesulfonyl)-N-(2'-(1H-tetrazol-5-yl)biphenyl-4-yl)methyl]amino-5-ethyl-1,3,4-thiadiazole [Compound No.212]:

Property pale yellow power
$^1$H-NMR($\delta$ppm in CDCl$_3$)
7.86–7.93(2H,m), 7.58(1H,m), 7.14–7.52(7H,m), 6.92 (2H,d), 5.14(2H,s), 2.92(2H,q), 1.30(3H,t)

(2) 2-[N-(2-Bromobenzenesulfonyl)-N-(2'-(1H-tetrazol-5-yl)biphenyl-4-yl)methyl]amino-5-ethyl-1,3,4-thiadiazole [Compound No. 213]:

Property colorless powder
$^1$H-NMR($\delta$ppm in CDCl$_3$)
8.11(1H,m), 7.84(1H,m), 7.70(1H,m), 7.16–7.49(7H,m), 6.91(2H,m), 5.17(2H,s), 2.90(2H,q), 1.27(3H,t)

(3) 2-[N-Ethanesulfonyl-N-(2'-(1H-tetrazol-5-yl)-biphenyl-4-yl)methyl]amino-5-ethyl-1,3,4-thiadiazole [Compound No. 214]:

Property pale yellow powder
$^1$H-NMR($\delta$ppm in CDCl$_3$)
7.96–8.07(1H,m), 7.35–7.65(4H,m), 7.07–7.32(3H,d), 5.23(2H,s), 3.22(2H,q), 2.99(2H,q), 1.39(3H,t), 1.37 (3H,t)

(4) 2-[N-n-Propanesulfonyl)-N-(2'-(1H-tetrazol-5-yl)-biphenyl-4-yl)methyl]amino-5-ethyl-1,3,4-thiadiazole [Compound No. 215]:

Property colorless powder
$^1$H-NMR($\delta$ppm in CDCl$_3$)
8.06(1H,d), 7.33–7.62(5H,m), 7.13(2H,d), 5.22(2H,s), 3.18(2H,t), 2.99(2H,q), 1.87(2H,m), 1.37(3H,t), 1.04 (2H, t)

(5) 2-[N-(2-Chlorobenzenesulfonyl)-N-(2'-(1H-tetrazol-5-yl)phenyl-4-yl)methyl]amino-5-ethyl-1,3,4-thiadiazole [Compound No. 216]:

Property colorless powder
$^1$H-NMR($\delta$ppm in CDCl$_3$)
8.16(2H,m), 7.30–7.59(8H,m), 7.13(2H,d), 5.33(2H,s), 2.99(2H,q),1.36(3H,t)

Synthetic methods of thiazoline derivatives and thiazole derivatives (groupA/A-1,A-2) by preferable Preparation Process 1 in the present invention were described as below.

Example 36

(1) 2-Cyclopropylcarbonylimino-3-[2'-(1H-tetrazol-5-yl) biphenyl-4-yl]methylthiazoline-4-carboxylic acid ethyl ester [Compound No. 217]:

To a suspension of sodium hydride (24 mg, 55% in oil) in N,N-dimethylformamide (2 ml) was slowly added 2-cyclopropylcarbonylaminothiazole-4-carboxylic acid ethlyl ester (152 mg). When evolution of hydrogen ceased, a solution of 4'-bromomethyl-2-(N-triphenylmethyltetrazol-5-yl)biphenyl (279 mg) in N,N-dimethylformamide (3 ml) was added. After stirring for 3 hours at room temperature, water and ethyl acetate were added to the mixture. The organic layer was separated, washed with water and dried over anhydrous magnesium sulfate. The magnesium sulfate was removed by filtration and the filtrate was evaporated. The residue was separated by column chromatography on silica gel (eluent:chloroform). The fractions containing trytylated title compound were collected and the solvent was evaporated. Ethyl acetate was added to the residue and the precipitate was filtrated. The filtrate was evaporated.

To the residue were added dioxane (4 ml) and hydrochloric acid solution (2 ml). After stirring for 1 hour at room temperature, the reaction mixture was made basic with saturated sodium bicarbonate solution. The aqueous layer was washed with ether, neutralized with 10% hydrochloric acid solution, and extracted with ethyl acetate. The organic layer was separated, washed with water and dried over anhydrous magnesium sulfate. The magnesium sulfate was removed by filtration and the filtrate was evaporated. Ether was added, and the precipitate was filtrated and dried. The title compound No.217 was obtained as a colorless powder (35 mg).

Property colorless powder
$^1$H-NMR($\delta$ppm in CDCl$_3$)
8.13(1H,d), 7.56(1H,s), 7.50–7.61(2H,m), 7.38–7.41(1H, m), 7.32(2H,d), 7.14(2H,d), 5.90(2H,s), 4.31(2H,q), 1.80–1.90(1H,m), 1.37(3H,t), 1.00–1.08 (2H,m), 0.80–0.95 (2H,m)

(2) 2-[N-Cyclopropylcarbonyl-N-(2'-(1H-tetrazol-5-yl)-biphenyl-4-yl)methyl]aminothiazole-4-carboxylic acid ethyl ester [Compound No.218]:

To a suspension of sodium hydride (24 mg, 55% in oil) in N,N-dimethylformamide (2 ml) was slowly added 2-cyclopropylcarbonylaminothiazole-4-carboxylic acid ethyl ester (152 mg). When evolution of hydrogen ceased, a solution of 4'-bromomethyl-2-(N-triphenylmethyltetrazol-5-yl)biphenyl (279 mg) in N,N-dimethylformamide (3 ml) was added. After stirring for 3 hours at room temperature, water and ethyl acetate were added to the mixture. The organic layer was separated, washed with water and dried over anhydrous magnesium sulfate. The magnesium sulfate was removed by filtration and the filtrate was evaporated. The residue was separated by column chromatography on silica gel (eluent:chloroform). The fractions containing trytylated title compound were collected and the solvent was evaporated. Ethyl acetate was added to the residue and the crystals were filtrated.

The crystals were dissolved in the mixed solvent of dioxane (3 ml) and chloroform (1 ml), to the solution was added conc. hydrochloric acid solution (2 ml) followed by stirring at room temperature. After stirring for 1 hour, the reaction mixture was made basic with saturated sodium bicarbonate solution. The aqueous layer was washed with ether, neutralized with 10% hydrochloric acid solution, and extracted with ethyl acetate. The organic layer was separated, washed with water and dried over anhydrous magnesium sulfate. The magnesium sulfate was removed by filtration and the filtrate was evaporated. Diisopropyl ether was added, and the precipitate was filtrated and dried. The title compound No.218 was obtained as a colorless powder (32 mg).

Property colorless powder
$^1$H-NMR($\delta$ppm in CDCl$_3$)
7.93(1H,d), 7.86(1H,s), 6.90–7.50(7H,m), 5.68(2H,s), 4.31(2H,q), 1.72–1.80(1H,m), 1.21(3H,t), 1.06–1.01(2H,m), 0.72–0.79(2H,m)

Example 37

Compounds Nos.219–239 were synthesized in a similar manner to example 36.

(1) 2-Valerylimino-5-methyl-3-[2'-(1H-tetrazol-5-yl)-biphenyl-4-yl]methylthiazoline [Compound No.219]:
Property colorless crystals
Melting point 191°–192° C.
$^1$H-NMR($\delta$ppm in CDCl$_3$)
8.03(1H,d), 7.36–7.58 (3H,m), 7.24(2H,d), 7.10(2H,d), 6.60(1H,s), 5.30(2H,s), 2.41(2H,t), 2.19(3H,s), 1.55–1.64 (2H,m), 1.26–1.37 (2H,m), 0.90 (3H,t)

(2) 2-propionylimino-3-[2'-(1H-tetrazol-5-yl)biphenyl-4-yl]methylthiazoline-4-carboxylic acid ethyl ester [Compound No. 220]:
Property colorless powder
$^1$H-NMR($\delta$ppm in CDCl$_3$)
8.19(1H,d), 7.60(1H,s), 7.53–7.60(2H,m), 7.31–7.44(3H, m),7.15(2H,d), 5.92(2H,s), 4.32(2H,q), 2.58(2H,q), 1.35 (3H,t), 1.19(3H,t) ( 3) 2-Butyrylimino-3-[2'-(1H-tetrazol-5-yl)biphenyl-4-yl] methylthiazoline-4-carboxylic acid ethyl ester [Compound No. 221]:
Property colorless powder
$^1$H-NMR($\delta$ppm in CDCl$_3$)
8.15(1H,d), 7.58(1H,s), 7.54–7.57(2H,m), 7.37–7.39(1H, m), 7.35(2H,d), 7.15(2H,d), 5.92(2H,s), 4.32(2H,q), 2.52 (2H,t), 1.70–1.80(2H,m), 1.34(3H,t), 0.95 (3H, t)

(4) 2-Cyclopropylcarbonylimino-3-[2'-(1H-tetrazol-5-yl) biphenyl-4-yl]methyl-5-ethylthiazoline-4-carboxylic acid ethyl ester [Compound No. 222]:
Property colorless powder
$^1$H-NMR($\delta$ppm in CDCl$_3$)
8.12–8.15(1H,m), 7.13–7.59(7H,m), 5.84(2H,s), 4.30 (2H,q), 2.91(2H,q), 1.62(1H,brs), 1.22–1.35(6H,m), 1.02–1.05(2H,m), 0.86–0.88(7H,m)

(5) 2-Cyclopropylcarbonylimino-3-[2'-(1H-tetrazol-5-yl) biphenyl-4-yl]methyl-5-n-propylthiazoline-4-carboxylic acid ethyl ester [Compound No.223]:
Property pale yellow amorphous
$^1$H-NMR($\delta$ppm in CDCl$_3$)
7.06–8.03(5H,m), 5.80(2H,s), 4.27(2H,q), 2.80(2H,t), 1.86(1H,brs), 1.54–1.62(2H,m), 1.30(3H,t), 0.84–0.99 (7H, m)

(6) 2-Cyclopropylcarbonylimino-3-[2'-(1H-tetrazol-5-yl) biphenyl-4-yl]methyl-5-n-butylthiazoline-4- carboxylic acid ethyl ester [Compound No. 224]:
Property colorless powder
$^1$H-NMR($\delta$ppm in CDCl$_3$)
8.02(1H,d), 7.52–7.57(2H,m), 7.39(1H,d), 7.18(2H,d), 7.07(2H,d), 5.78(2H,s), 4.27(2H,q), 2.79(2H,t), 2.20–2.27 (1H,m), 1.82–1.84 (2H,m), 1.50–1.52 (2H,m), 1.27–1.38 (5H,m), 0.88–1.98(7H,m)

(7) 2-Cyclopropylcarbonylimino-3-[2'-(1H-tetrazol-5-yl) biphenyl-4-yl]methyl-5-chlorothiazoline-4-carboxylic acid ethyl ester [Compound No.225]:
Property colorless powder
$^1$H-NMR($\delta$ppm in CDCl$_3$)
8.21(1H,dd), 7.58–7.64(2H,m), 7.21–7.47(3H,m), 6.93 (2H,d), 5.81(2H,s), 4.35(2H,q), 1.88–1.92(1H,m), 1.35 (3H, t), 1.09–1.24 (2H,m), 0.90–0.94 (2H,m)

(8) 2-Butyrylimino-3-[2'-(1H-tetrazol-5-yl)biphenyl-4-yl] methyl-5-n-propylthiazoline-4-carboxylic acid ethyl ester [Compound No. 226]:
Property pale yellow amorphous
$^1$H-NMR($\delta$ppm in CDCl$_3$)
7.57(1H,d), 7.09–7.40(7H,m), 5.87(2H,s), 4.29(2H,q), 2.85(2H,t), 2.53(2H,t), 1.63–1.71(4H,m), 1.31(3H,t), 0.07–1.02 (6H,m)

(9) 2-Pivaloylimino-3-[2'-(1H-tetrazol-5-yl)biphenyl-4-yl] methyl-5-ethylthiazoline-4-carboxylic acid ethyl ester [Compound No. 227]:
Property colorless powder
$^1$H-NMR($\delta$ppm in CDCl$_3$)
8.02(1H,d), 7.09–7.65(7H,m), 5.80(2H,s), 4.30(2H,q), 2.89(2H,q), 1.32(3H,t), 1.22(3H,t), 1.19(9H,s)

(10) 2-Benzoylimino-3-(2'-cyanobiphenyl-4-yl)methyl-5-ethylthiazoline-4-carboxylic acid ethyl ester [Compound No.228]:
Property brown oil
$^1$H-NMR($\delta$ppm in CDCl$_3$)
8.33(2H,d), 7.39–7.75(11H,m), 6.04(2H,s), 4.35(2H,q), 2.99(2H,q), 1.30–1.37 (6H,m)

(11) 2-Benzoylimino-3-[2'-(1H-tetrazol-5-yl)biphenyl-4-yl]methylthiazoline-4-carboxylic acid ethyl ester [Compound No. 229]:
Property colorless powder
$^1$H-NMR(δppm in CDCl$_3$)
8.30(2H,d), 7.18–7.69(12H,m), 6.09(2H,s), 4.36(2H,q), 1.37(3H,t)

(12) 2-Benzoylimino-3-[2'-(1H-tetrazol-5-yl)biphenyl-4-methyl-5-n-propylthiazoline-4-carboxylic acid ethyl ester [Compound No.230]:
Property colorless powder
$^1$H-NMR(δppm in DMSO-d$_6$)
8.14–8.17(2H,m), 7.45–7.68(7H,m), 7.15(2H,d), 7.06 (2H,d), 5.83(2H,s), 4.25(2H,q), 2.92(2H,t), 1.61–1.69(2H, m), 1.20(3H,t), 0.94(3H,t)

(13) 2-(2-Chlorobenzoylimino)-3-[2'-(1H-tetrazol-5-yl)biphenyl-4-yl]methylthiazoline-4-carboxylic acid ethyl ester [Compound No.231]:
Property colorless powder
$^1$H-NMR(δppm in CDCl$_3$)
8.09(1H,s), 7.93–7.98(2H,m), 6.74–7.74(10H,m), 5.98 (2H,d), 4.12(2H,q), 1.27(3H,t)

(14) 2-(2-Chlorobenzoylimino)-3-[2'-(1H-tetrazol-5-yl)biphenyl-4-yl]methyl-5-n-propylthiazoline-4-carboxylic acid ethyl ester [Compound No.232]:
Property pale yellow powder
$^1$H-NMR(δppm in CDCl$_3$)
8.05(1H,d), 7.92(1H,d), 7.12–7.57(10H,m), 5.91(2H,s), 4.31(2H,q), 2.92(2H,t), 1.67–1.77(2H,m), 1.34 (3H,t), 1.00 (3H,t)

(15) 2-[N-Valeryl-N-(2'-(1H-tetrazol-5-yl)biphenyl-4-yl)methyl]amino-5-methylthiazole [Compound No. 233]:
Property colorless crystals
Melting point 129° C.
$^1$H-NMR(δppm in CDCl$_3$)
8.18(1H,d), 7.01–7.68(8H,m), 5.44(2H,brs), 2.44–2.59 (2H,m), 2.40(3H,s), 1.64–1.75(2H,m), 1.30–1.39(2H,m), 0.89(3H,t)

(16) 2-[N-Butyryl-N-(2'-(1H-tetrazol-5-yl)biphenyl-4-yl)methyl]amino-5-n-propylthiazole-4-carboxylic acid ethyl ester [Compound No. 234]:
Property colorless powder
$^1$H-NMR(δppm in CDCl$_3$) 8.04 (1H,d), 7.01–7.57(7H,m), 5.36(2H,s), 4.33 (2H, q), 3.10 (2H, t), 2.50(2H,t), 1.68–1.79 (4H,m), 1.36(3H,t), 1.02(3H,t), 0.94(3H,t)

(17) 2-[N-Butyryl-N-(2'-(1H-tetrazol-5-yl)biphenyl-4-yl)methyl]amino-5-chlorothiazole-4-carboxylic acid ethyl ester [Compound No. 235]:
Property colorless powder
$^1$H-NMR(δppm in CDCl$_3$)
8.04 (1H,dd), 7.52–7.57 (2H,m), 7.36–7.38 (1H,d), 7.04–7.12(1H,m), 5.35(2H,s), 4.37 (2H,q), 2.53 (2H,t), 1.69–1.77(2H,m), 1.39(3H,t), 0.94(3H,t)

(18) 2-[N-Cyclopropylcarbonyl-N-(2'-(1H-tetrazol-5-yl)biphenyl-4-yl)methyl]amino-5-ethylthiazole-4-carboxylic acid ethyl ester [Compound No.236]:
Property colorless powder
$^1$H-NMR (δppm in CDCl$_3$) 6.94–8.00(8H,m), 5.49(2H, brs), 4.34(2H,q), 3.14(2H,q), 1.77–1.87(1H,m), 1.30–1.39 (6H,m), 1.14 (2H,brs), 0.91–0.96 (2H,m)

(19) 2-[N-Cyclopropylcarbonyl-N-(2'-(1H-tetrazol-5-yl)biphenyl-4-yl)methyl]amino-5-n-propylthiazole-4-carboxylic acid ethyl ester [Compound No. 237]:
Property colorless powder
$^1$H-NMR(δppm in CDCl$_3$)
6.90–7.91(8H,m), 5.44 (2H,brs), 4.32(2H,q), 3.08(2H,t), 1.59–1.74 (3H,m), 0.88–1.36(10H,m)

(20) 2-[N-Cyclopropylcarbonyl-N-(2'-(1H-tetrazol-5-yl)biphenyl- 4-yl)methyl]amino-5-n-butylthiazole-4-carboxylic acid ethyl ester [Compound No.238]:
Property colorless powder
$^1$H-NMR(δppm in CDCl$_3$)
7.98–8.01(1H,m), 7.54–7.56(2H,m), 7.35–7.38(1H,m), 7.04–7.11(2H,m), 6.97–7.02(2H,m), 5.51(2H,s), 4.28(2H, q), 3.11(2H,t), 1.34–1.39(5H,m), 1.26–1.28(2H,m), 1.15–1.18(2H,m), 0.92–0.97(6H,m)

(21) 2-[N-Cyclopropylcarbonyl-N-(2'-(1H-tetrazol-5-yl)biphenyl-4-yl)methyl]amino-5-chlorothiazole-4-carboxylic acid ethyl ester [Compound No.239]:
Property colorless powder
$^1$H-NMR(δppm in CDCl$_3$)
8.03(1H,dd), 7.53–7.57(2H,m), 7.37(1H,dd), 7.13(2H,d), 7.03(2H,d), 5.54(2H,s), 4.37(2H,q), 1.83–1.90(1H,m), 1.38 (3H,t), 1.18–1.21(2H,m), 1.00–1.03 (2H,m)

Example 38

Compounds Nos.240–256 were obtained by hydrolysis of thiazoline-4-carboxylic acid ethyl ester derivatives and thiazole-4-carboxylic acid ethyl ester derivatives obtained in example 36 and 37 with sodium hyroxide solution.

(1) 2-Propionylimino-3-[2'-(1H-tetrazol-5-yl)biphenyl-4-yl]methylthiazoline-4-carboxylic acid [Compound No.240]:
Property colorless powder
$^1$H-NMR(δppm in DMSO-d$_6$)
7.90(1H,s), 7.49–7.68(4H,m), 7.05–7.14(4H,m), 5.79 (2H,s), 2.42(2H,q), 1.06(3H,t)

(2) 2-Butyrylimino-3-[2'-(1H-tetrazol-5-yl)biphenyl-4-yl]methylthiazoline-4-carboxylic acid [Compound No.241]:
Property colorless powder
$^1$H-NMR(δppm in DMSO-d$_6$)
7.90(1H,s), 7.54–7.64(4H,m), 7.10(2H,d), 7.05(2H,d), 5.78(2H,s), 2.38(2H,t), 1.54–1.64(2H,m), 0.85(3H,t)

(3) 2-Cyclopropylcarbonylimino-3-[2'-(1H-tetrazol-5-yl)biphenyl-4-yl]methylthiazoline-4-carboxylic acid [Compound No. 242]:
Property colorless powder
$^1$H-NMR(δppm in DMSO-d$_6$)
7.89(1H,s), 7.55–7.66(4H,m), 7.06–7.12(4H,m), 5.76 (2H,s), 1.70–1.76(1H,m), 0.80–0.83(4H,m)

(4) 2-Cyclopropylcarbonylimino-3-[2'-(1H-tetrazol-5-yl)biphenyl-4-yl]methyl-5-ethylthiazoline-4-carboxylic acid [Compound No. 243]:
Property colorless powder
$^1$H-NMR(δppm in DMSO-d$_6$)
7.52–7.63(4H,m), 7.06(4H,s), 5.70(2H,s), 2.93(2H,q), 1.69–1.75(1H,m), 1.17(3H,t), 0.79–0.82(4H,m)

(5) 2-Cyclopropylcarbonylimino-3-[2'-(1H-tetrazol-5-yl)biphenyl-4-yl]methyl-5-n-propylthiazoline-4-carboxylic acid [Compound No. 244]:
Property pale yellow powder
$^1$H-NMR(δppm in DMSO-d$_6$)
7.52–7.67(4H,m), 7.06(4H,s), 5.69(2H,s), 2.90(2H,t), 1.73 (1H,brs), 1.56–1.64 (2H,m), 0.79–0.96(7H,m)

(6) 2-Cyclopropylcarbonylimino-3-[2'-(1H-tetrazol-5-yl)biphenyl-4-yl]methyl-5-n-butylthiazoline-4-carboxylic acid [Compound No. 245]:
Property colorless powder
$^1$H-NMR(δppm in DMSO-d$_6$)
7.67–7.70 (2H,m), 7.55–7.61 (2H,m), 7.04–7.13 (4H,m), 5.71(2H,s), 2.92–2.96(2H,m), 2.17–2.26(2H,m), 1.71–1.77 (1H,m), 1.53–1.58(2H,m), 0.78–0.92 (7H,m)

(7) 2-pivaloylimino-3-[2'-(tetrazol-5-yl)biphenyl-4-yl]-methyl-5-ethylthiazoline-4-carboxylic acid [Compound No.246]:

Property colorless powder
¹H-NMR(δppm in DMSO-d₆)
7.50–7.69(4H,m), 7.15(2H,d), 7.04(2H,d), 5.70(2H,s), 2.94(2H,q), 1.19(3H,t), 1.12(9H,s)

(8) 2-Benzoylimino-3-(2'-cyanobiphenyl-4-yl)ethyl-5-ethylthiazoline-4-carboxylic acid [Compound No. 247]:
Property pale yellow powder
¹H-NMR (δppm in CDCl₃)
8.33(2H,d), 7.41–7.76(11H,m), 6.09(2H,s), 3.09 (2H,q), 1.35 (3H, t)

(9) 2-Benzoylimino-3-[2'-(1H-tetrazol-5-yl)biphenyl-4-yl]methylthiazoline-4-carboxylic acid [Compound No. 248]:
Property colorless powder
¹H-NMR(δppm in DMSO-d₆)
8.15–8.18(2H,m), 7.46–7.65(8H,m), 7.22(2H,d), 7.06 (2H,d), 5.97(2H,s)

(10) 2-Benzoylimino-3-[2'-(1H-tetrazol-5-yl)biphenyl-4-yl]methyl-5-n-propylthiazoline-4-carboxylic acid [Compound No. 249]:
Property colorless powder
¹H-NMR(δppm in DMSO-d₆)
8.15(2H,d), 7.38–7.63(7H,m), 7.17(2H,d), 7.07(2H,d), 5.89(2H,s), 2.96(2H,t), 1.61–1.70(2H,m), 0.94(3H,t)

(11) 2-(2-Chlorobenzoyl) imino-3-[2'-(1H-tetrazol-5-yl)biphenyl-4-yl]methylthiazoline-4-carboxylic acid [Compound No.250]:
Property colorless powder
¹H-NMR(δppm in DMSO-d₆)
8.06(1H,s), 7.04–7.82(8H,m), 7.14(2H,d), 7.05(2H,d), 5.89(2H,s)

(12) 2-(2-Chlorobenzoyl)imino-3-[2'-(1H-tetrazol-5-yl)biphenyl- 4-yl]methyl-5-n-propylthiazoline-4-carboxylic acid [Compound No. 251]:
Property pale yellow powder
¹H-NMR(δppm in DMSO-d₆)
7.04–7.81(12H,m), 5.82(2H,s), 2.98(2H,t), 1.59–1.73 (2H,m), 0.94 (3H,t)

(13) 2-[N-Butyryl-N-(2'-(1H-tetrazol-5-yl)biphenyl-4-yl)methyl]amino-5-chlorothiazole-4-carboxylic acid [Compound No.252]:
Property colorless powder
¹H-NMR(δppm in DMSO-d₆)
7.65–7.70(2H,m), 7.56–7.59(2H,m), 7.28(2H,d), 7.08 (2H,d), 5.45(2H,s), 2.56(3H,t), 1.51–1.58(1H,m), 0.85 (3H, t)

(14) 2-[N-Cyclopropylcarbonyl-N-(2'-(1H-tetrazol-5-yl) biphenyl-4-yl)methyl]aminothiazole-4-carboxylic acid [Compound No. 253]:
Property colorless powder
¹H-NMR(δppm in DMSO-d₆)
8.05(1H,s), 7.54–7.67(4H,m), 7.21(2H,d), 7.08(2H,d), 5.73(2H,s), 2.09–2.13(1H,m), 0.88–0.94(4H,m)

(15) 2-[N-Cyclopropylcarbonyl-N-(2'-(1H-tetrazol-5-yl)biphenyl-4-yl)methyl]amino-5-ethylthiazole-4-carboxylic acid [Compound No. 254]:
Property colorless powder
¹H-NMR(δppm in DMSO-d₆)
7.06–7.64(8H,m), 5.68(2H,s), 3.10(2H,q), 2.10(1H,brs), 1.23(3H,t), 0.89(4H,brs)

(16) 2-[N-Cyclopropylcarbonyl-N-(2'-(1H-tetrazol-5-yl) biphenyl-4-yl)methyl]amino-5-n-propylthiazole-4-carboxylic acid [Compound No. 255]:
Property pale yellow powder
¹H-NMR(δppm in DMSO-d₆)
7.06–7.67(8H,m), 5.68(2H,s), 3.06(2H,t), 2.08(1H,brs), 1.59–1.68(2H,m), 0.78–0.93(7H,m)

(17) 2-[N-Cyclopropylcarbonyl-N-(2'-(1H-tetrazol-5-yl) biphenyl-4-yl)methyl]amino-5-chlorothiazole-4-carboxylic acid [Compound No. 256]:
Property colorless powder
¹H-NMR(δppm in DMSO-d₆)
7.65–7.68(2H,m), 7.53–7.57(2H,m), 7.22(2H,d), 7.08 (2H,d), 5.67(2H,s), 2.08–2.19(1H,m), 0.87–0.93 (4H,m)

Example 39

The compound obtained in example 38 was further deacylated with an aqueous sodium hydroxide solution to give the compounds Nos.257~259.

(1) 2-Imino-3-[2'-(1H-tetrazol-5-yl)biphenyl-4-yl]-methyl-5-ethylthiazoline-4-carboxylic acid [Compound No.257]:
Property pale yellow powder
¹H-NMR(δppm in DMSO-d₆)
6.85–7.66 (m, 8H), 4.52 (brs, 2H), 3.00 (q, 2H), 1.15 (t, 3H)

(2) 2-[(2'-(1H-tetrazol-5-yl)biphenyl-4-yl)methyl]amino-5-ethylthiazole-4-carboxylic acid [Compound No.258]:
Property colorless powder
¹H-NMR(δppm in DMSO-d₆)
8.04(1H,brs), 7.53–7.68(4H,m), 7.28(2H,d), 7.07(2H,.d), 4.43(2H,d), 2.98(2H,q), 1.14(3H,t)

(3) 2-[(2'-(1H-tetrazol-5-yl)biphenyl-4-yl)methylamino]-5-n-propylthiazole-4-carboxylic acid [Compound No. 259]:
Property pale purple powder
¹H-NMR(δppm in DMSO-d₆)
8.00(1H,brs), 7.05–7.65(8H,m), 4.43(2H,d), 2.95(2H,t), 1.46–1.59(2H,m), 0.89(3H,t)

Synthetic methods of following two thiadiazole derivatives by preferable Preparation Process 1 in the present invention were described as below (example 40~example 44).

[Synthesis of thiazoleacetic acid derivative]

Example 40

(1) 2-[N-Butyryl-N-(2'-(1H-tetrazol-5-yl)biphenyl-4-yl)methyl]aminothiazole-4-acetic acid ethyl ester [Compound No. 260]:

To a suspension of sodium hydride (40 mg, 55% in oil) in N,N-dimethylformamide (5 ml) was added 2-butyrylmmino-thiazol-4-acetic acid ethyl ester (0.2 g). When evolution of hydrogen ceased, a solution of 4'-bromomethyl-2-(N-triphenylmethyltetrazol-5-yl) biphenyl (0.4 g) in N,N-dimethylformamide (5 ml) was added. After stirring for 3 hours, water and ethyl acetate were added to the mixture. The organic layer was separated, washed with water and dried over anhydrous magnesium sulfate. The magnesium sulfate was removed by filtration and the filtrate was evaporated. The residue was purified by column chromatography on silica gel(eluent:chloroform). The fractions containing main product were collected and the solvent was evaporated.

The residue was dissolved in dioxane (5 ml), to the solution was added 10% hydrochloric acid solution (1 ml) followed by stirring at room temperature. After stirring for 2 hours, the reaction mixture was made basic with 5% aqueous sodium hydroxide solution. The aqueous layer was washed with ether, adjusted to about pH 2–3 with 10% hydrochloric acid solution, and extracted with ethyl acetate. The organic layer was separated, washed with water and dried over anhydrous magnesium sulfate. The magnesium Sulfate was removed by filtration and the filtrate was evaporated. The resultant oil crystallized on standing. Diisopropyl ether was added, and the crystals were filtrated and dried. The title compound No.260 was obtained as colorless crystals(78 mg).

Property colorless crystals
Melting point 170°–172° C.

¹H-NMR(δppm in CDCl₃)

8.10(1H,d), 6.80–7.60(8H,m), 5.45(2H,s), 4.10(2H,q), 3.68(2H,s), 2.58(2H,t), 1.72–1.79(2H,m), 1.22(3H,t), 0.98 (3H, t)

[Alkylaminothiazole derivatives ]

Example 41

2-[N-n-Propyl-N-(2'-(1H-tetrazol-5-yl)biphenyl-4-yl)-methyl)]amino-5-n-propylthiazole-4-carboxylic acid [Compound No. 261]:

n-Propylthiourea (270 mg), 3-chloro-2-oxohexanoic acid ethyl ester (441 mg), and pyridine (0.28 ml) were added to ethanol (10 ml), and the solution was refluxed for 3.5 hours. The solvent was evaporated. The residue was extracted with chloroform (20 ml), and washed with dilute hydrochloric acid solution (10 ml). The organic layer was dried over anhydrous magnesium sulfate and evaporated. The residue was purified by column chromatography on silica gel (eluent:chloroform/methanol=100/1), 2-n-propylamino-5-n-propyl thiazole-4-carboxylic acid ethyl ester (400 mg) was obtained.

The 2-aminothiazole compound (400 mg) obtained above and 1,3-dimethyl-3,4,5,6-tetrahydro-2-(1H)-pyridine (300 mg) were added to tetrahydrofuran (3 ml), then to the solution was added slowly 1.0 M lithium hexamethyldisilazane (1.5 ml) in tetrahydrofuran on ice. The solution was stirred for 20 minutes as such. To the solution was added of 2-(2-triphenylmethyltetrazol-5-yl)-4'-bromomethylbiphenyl (820 mg) in terahydrofuran (2 ml) on ice, and the mixture was stirred at room temperature for 3 hours. The solvent was evaporated. The residue was extracted with ethyl acetate (40 ml). The organic layer was washed with dilute hydrochloric acid solution followed by washing with 20 ml of saturated sodium chloride solution, dried over anhydrous magnesium sulfate, and then was evaporated. The residue was separated by column chromatography on silica gel (eluent:chloroform) to give yellow oily compound (510 mg). The yellow oily compound was added to dioxane (20 ml), to the solution was added conc. hydrochloric acid solution (18 ml) at room temperature, then the solution was stirred for 1.5 hour. To the solution was added water (40 ml), and the mixture was extracted with ethyl acetate (40 ml). The organic layer was dried over anhydrous magnesium sulfate and evaporated. The residue was purified by column chromatography on silica gel(eluent:chloroform→ethyl acetate) to give the title compound No.261 as a pale yellow amorphous (149 mg).

Property pale yellow amorphous

¹H-NMR(δppm in CDCl₃)

8.10(1H,d), 7.03–7.57(7H,m), 4.70(2H,s), 4.30(2H,q), 3.32(2H,brs), 3.03(2H,t), 1.60–1.69(4H,m), 1.35(3H,t), 0.90–1.03(6H,m)

Example 42

Compounds Nos.262–267 were synthesized in a similar manner to example 41.

(1) 2-[N-n-Butyl-N-(2'-(1H-tetrazol-5-yl)biphenyl-4-yl)methyl]amino-n-propylthiazole-4-carboxylic acid ethyl ester [Compound No. 262]:

Property orange amorphous

¹H-NMR(δppm in CDCl₃)

8.08(1H,d), 7.02–7.57(7H,m), 4.68(2H,s), 4.30(2H,q), 3.34(2H,t), 3.03(2H,t), 1.60–1.69(4H,m), 1.32–1.37 (5H,m), 0.91–1.03 (6H,m)

(2) 2-[N-Cyclopropylmethyl-N-(2'-(1H-tetrazol-5-yl) biphenyl-4-yl)methyl]amino-5-n-propylthiazole-4-carboxylic acid ethyl ester[Compound No.263]:

Property orange amorphous

¹H-NMR(δppm in CDCl₃)

7.93 (1H,d), 6.89–7.57(7H,m), 4.69(2H,s), 4.27 (2H,q), 3.20 (2H, t), 3.02(2H,t), 1.60–1.72(2H,m), 1.32(3H,t), 0.85–1.03(4H,m), 0.50(2H,d), 0.17(2H,d)

(3) N-[2'-(1H-tetrazol-5-yl)biphenyl-4-ylmethyl]-N-(5-n-propyl-4-ethoxycarbonylthiazole-2-yl)aminoacetic acid ethyl ester [Compound No. 264]:

Property yellow powder

¹H-NMR(δppm in CDCl₃)

6.99–8.01(8H,m), 4.62(2H,s), 4.29(2H,q), 4.18(2H,q), 4.12(2H,s), 3.02(2H, t), 1.62–1.71(2H,m), 1.34(3H,t), 1.25 (3H,t), 0.99(3H,t)

(4) 2-[N-Benzyl-N-(2 '-(1H-tetrazol-5-yl)biphenyl-4-yl) methyl]amino-5-ethylthiazole-4-carboxylic acid ethyl ester [Compound No. 265]:

Property amorphous

¹H-NMR(δppm in CDCl₃)

8.14 (1H,d), 7.08–7.57 (12H,m), 4.66, 4.63 (each 2H,each s), 4.32(2H,q), 3.09(2H,q), 1.36(3H,t), 1.27 (3H,t)

(5) 2-[N-Benzyl-N-(2'-(1H-tetrazol-5-yl)biphenyl-4-yl) methyl]amino-5-n-propylthiazole-4-carboxylic acid ethyl ester [Compound No. 266]:

Property pale yellow amorphous

¹H-NMR(δppm in CDCl₃)

8.01(1H,d), 6.85–7.59(12H,m), 4.59, 4.56 (each 2H,each s), 4.30(2H,q), 3.02(2H,t), 1.62–1.71 (2H,m), 1.35(3H,t), 0.99(3H,t)

(6) 2-[N-(2'-( 1H-tetrazol-5-yl)biphenyl-4-yl)methyl-N-(2-methoxycarbonylphenyl)methyl]amino-5-n-propylthiazole-4-carboxylic acidethyl ester [Compound No.267]:

Property pale yellow powder

¹H-NMR(δppm in CDCl₃)

6.97–8.01(12H,m), 4.97, 4.65(each 2H,each s), 4.30(2H, q), 3.80(3H,s), 3.01(2H,t), 1.61–1.69(2H,m), 1.35(3H,t), 0.98(3H,t)

Example 43

2-[N-n-Propyl-N-(2'-(1H-tetrazol-5-yl)biphenyl-4-yl) methyl]amino-5-n-propylthiazole-4-carboxylic acid [Compound No. 268]:

The compound No.261 (230 mg) obtained in example 41 was added to ethanol (2 ml) and 10% sodium hydroxide (1 ml). After stirring for 4 hours at room temperature, the reaction mixture was acidified with 20% hydrochloric solution (1 ml) and extracted with ethyl acetate (40 ml). The organic layer was dried over anhydrous magnesium sulfate, and the solvent was evaporated. Hexane was added to the residue. The precipitated solid was filtrated and dried to give the the title compound No.268(90 mg).

Property pale brown powder

¹H-NMR (δppm in DMSO-d₆)

7.54–7.71(4H,m), 7.23(2H,d), 7.07(2H,d), 4.66(2H,s), 3.31(2H,t), 2.97(2H,t), 1.47–1.57(4H,m), 0.81–0.93 (6H,m)

Example 44

Compounds Nos. 269–272 were synthesized in a similar manner to example 43.

(1) 2-[N-n-Butyl-N-(2'-(1H-tetrazol-5-yl)biphenyl-4-yl) methyl]amino-5-n-propylthiazole-4-carboxylic acid [Compound No. 269]:

Property pale brown powder

¹H-NMR(δppm in DMSO-d₆)

7.54–7.68(4H,m), 7.23(2H,d), 7.07(2H,d), 4.66(2H,s), 3.34(2H,t), 3.00(2H,t), 1.47–1.60(4H,m), 1.20–1.33 (2H,m), 0.85–0.93 (6H,m)

(2) 2-[N-Cyclopropylmethyl-N-(2'-(1H-tetrazol-5-yl)-biphenyl-4-yl)methyl]amino-5-n-propylthiazole-4-carboxylic acid[Compound No. 270]:
Property pale orange amorphous
¹H-NMR(δppm in CDCl₃)
6.81–7.86(5H,m), 4.67(2H,s), 3.22(2H,d), 3.06(2H,t), 1.57–1.88 (2H,m), 0.88–1.00(4H,m), 0.51(2H,d), 0.17 (2H, d)
(3) 2-[N-Benzyl-N-(2'-(1H-tetrazol-5-yl)biphenyl-4-yl)methyl]amino-5-ethylthiazole-4-carboxylic acid [Compound No.271]:
Property pale yellow powder
¹H-NMR(δppm in DMSO-d₆)
7.06–7.72(13H,m), 4.65(4H,s), 3.00(2H,q), 1.14(3H,t)
(4) 2-[N-Benzyl-N-(2'-(1H-tetrazol-5-yl)biphenyl-4-yl)methyl]amino-5-n-propylthiazole-4-carboxylic acid [Compound No. 272]:
Property pale yellow amorphous
¹H-NMR(δppm in DMSO-d₆)
7.06–7.71(12H,m), 6.75–6.78(1H,m), 4.66(4H,s), 2.97 (2H,t), 1.47–1.61(2H,m), 0.89(3H,t)

The synthetic methods (Preparation Process-1) of benzothiazoline and benzothiazole derivatives (groupA/A-5,A-6) were described as below.

Example 45

Compounds Nos.273~276 were synthesized in a similar manner to example 1 (1) and (2).

(1) 2-Cyclopropylcarbonylimino-3-[2'-(1H-tetrazol-5-yl)biphenyl-4-yl]methylbenzothiazoline [Compound No. 273]:
Property colorless powder
¹H-NMR(δppm in CDCl₃)
7.13–8.03(12H,m), 5.75(2H,s), 1.86–1.95(1H,m), 1.20–1.28, 0.94–0.98(each 2H,each m)
(2) 2-[N-Cyclopropylcarbonyl-N-(2'-(1H-tetrazol-5-yl)biphenyl-4-yl)methyl]aminobenzothiazole [Compound No. 274]:
Property colorless powder
¹H-NMR(δppm in DMSO-d₆)
7.06–7.89(12H,m), 5.64 (2H,s), 1.85–1.99(1H,m), 0.86–0.96 (4H,m)
(3) 2-Cyclopropylcarbonylimino-5,6-dimethyl-3-[2'-(1H-tetrazol-5-yl)biphenyl-4-yl]methylbenzothiazoline Compound No. 275]:
Property colorless powder
¹H-NMR(δppm in DMSO-d₆)
7.43–7.62(6H,m), 7.23(2H,d), 7.08(2H,d), 5.59(2H,s) 2.27(6H,s), 1.81(1H,m), 0.80–0.88(4H,m)
(4) 2-[N-Cyclopropylcarbonyl-N-(2'-(1H-tetrazol-5-yl)biphenyl-4-yl)methyl]amino-5,6-dimethylbenzothiazole [Compound No.276]:
Property colorless crystals
Melting point 234°–235° C.
¹H-NMR(δppm in DMSO-d₆)
7.57–7.70(6H,m), 7.23(2H,d), 7.08(2H,d), 5.78(2H,s) 2.31(6H,s), 2.15(1H,m), 0.80–0.96(4H,m)

The synthetic methods (Preparation Process-1) of oxadiazole derivatives (groupA/A-12) were described below.

Reference Example 8

2-Amino-5-ethyl-1,3,4-oxadiazole:

n-propionylthiosemicarbazide (40.3 g) and lead(II) oxide (180 g) were added to propanol (600 ml), was heated under reflux over night. After cooling, the precipitate was removed by filtration. The filtrate was evaporated to give crystals. Recrystallization from ethanol gave the title compound (7 g).

Reference Example 9

2-Vareloylamino-5-ethyl-1,3,4-oxadiazole:

2-Amino-5-ethyl-1,3,4-oxadiazole (1.0 g) was added to a mixture of pyridine (1 ml) and tetrahydrofuran (10 ml). To the mixture was added varelyl chloride (1.2 g) under cooling on dryice/methanol. After stirring for 1 hour, water and ethyl acetate were added to the mixture followed by stirring. The organic layer was separated, washed with water, and dried over anhydrous magnesium sulfate. The magnesium sulfate was removed by filtration. The resultant oil crystallized on standing. Diisopropyl ether was added, and the crystals were filtrated and dried to give the title compound (0.26 g).

Example 46

Using 2-vareloylamino-5-ethyl-1,3,4-oxadiazole as a starting material in the reaction of example 1, the corresponding oxadiazole derivatives was only obtained.

2-[N-Vareloyl-N-(2'-(1H-tetrazol-5-yl)biphenyl-4-yl)methyl]amino-5-ethyl-1,3,4-oxadiazole[Compound No.277]:
Property colorless powder
¹H-NMR(δppm in CDCl₃)
7.88–8.08 (1H,m), 7.05–7.75 (7H,m), 5.04 (2H,s), 2.80–2.90 (2H,m), 2.55–2.72 (2H ,m), 1.48–1.72 (2H,m), 1.20–1.40(5H,m), 0.90 (3H, t)

Syntheses of isoxazoline derivatives (group A/A-17) by Preparation Process-1

Example 47

Compounds Nos.278 and 279 were derived from 3-cyclopropylcarbonylamino-5-methylisoxazole and 3-butyrylamino-5-methylisoxazole in a similar manner to example 3.

(1) 3-Cyclopropylcarbonylimino-5-methyl-2-[2'-(1H-tetrazol-5-yl)biphenyl-4-yl]methylisoxazoline [Compound No.278]:
Property colorless powder
¹H-NMR(δppm in CDCl₃)
8.04(1H,d), 7.02–7.79(8H,m), 5.05(2H,s), 2.41(3H,s) 1.79–1.83(1H,m), 1.07–1.13(2H,m), 0.84–0.88(2H,m)
(2) 3-Butyrylimino-5-methyl-2-[2'-(1H-tetrazol-5'-yl)biphenyl-4-yl]methylisoxazoline [Compound No. 279]:
Property colorless powder
¹H-NMR(δppm in CDCl₃)
7.89 (1H,d), 7.02–7.48 (8H,m), 4.92(2H,s), 2.37(2H,t), 2.29(3H,s), 1.62–1.70 (2H,m), 0.89 (3H,t)

Example 48

Compounds Nos.280 and 281 were synthesized in a similar manner to example 18 and 20.
(1) cis-3-[[5-Ethyl-3-[2'-(1H-tetrazol-5-yl)biphenyl-4-yl]methyl-1,3,4-thiadiazoline-2-yliden]aminocarbonyl]-5-norbornene-2-carboxylic acid benzyl ester [Compound No. 280]:
Property colorless powder
¹H-NMR (δppm in CDCl₃)
8.14(1H,dd), 7.15–7.65(12H,m), 6.23(2H,s), 5.38(2H,s), 4.88(2H,dd), 3.62–3.67(1H,m), 3.39–3.43(1H,m), 2.81(2H, q), 1.39–1.51(2H,m), 1.30 (3H,t)
(2) cis-3-[[5-Ethyl-3-[2'-(1H-tetrazol-5-yl)biphenyl-4-yl]methyl-1,3,4-thiadiazoline-2-yliden]-aminocarbonyl]-5-norbornene -2-carboxylic acid [Compound No.281]:
Property colorless powder
¹H-NMR(δppm in DMSO-d₆)

7.51–7.68(4H,m), 7.30(2H,d), 7.10(2H,d), 6.34 (1H,m), 6.10(1H,m), 5.48(2H,s), 2.70–3.20(4H,m), 2.88(2H,q), 1.15–1.57 (2H,m), 1.24 (3H,t)

Example 49

Dipotassium 2-[[5-Ethyl-3-[2'-(1H-tetrazol-5-yl) biphenyl-4-yl ]methyl-1,3,4-thiadiazoline-2-yliden]-aminocarbonyl]-1-cyclopentenecarboxylate (2K salt of compound No.130):

To a solution of 0.1N potassium hydroxide ethanolic solution (400 ml) and ethanol (600 ml) was added 2-[[5-Ethyl-3-[2'-(1H-tetrazol-5-yl)biphenyl-4-yl]methyl-1,3,4-thiadiazoline-2-yliden]aminocarbonyl]-1-cyclopentenecarboxylic acid (10 g), and the mixture was heated on water bath. After the mixture had been completely dissolved, the solvent was concentrated to 200 ml in vacuo. The precipitated crystals were filtrated, washed with ethanol, and then dried in vacuo. The title compound (11 g) was obtained.

Melting point >280° C.

IR(KBr) cm$^{-1}$ 1642 (—COOK) 1570 (=N—CO—)

$^1$H-NMR(δppm in D$_2$O)

7.51–7.62(3H,m), 7.37–7.39(1H,m), 7.31(2H,d), 7.04 (2H,d), 5.49(2H,s), 2.66–2.86(6H,m), 1.95–2.00(2H,m), 1.23(3H,t)

Example 50

Monopotassium 2-[[5-Ethyl-3-[2'-(1H-tetrazol-5-yl) biphenyl-4-yl]methyl-1,3,4-thiadiazoline-2-yliden]-aminocarbonyl]-1-cyolopentenecarboxylate (1K salt of compound No. 130):

To a solution of 0.05N potassium hydroxide ethanolic solution (8.3 ml) and ethanol (50 ml) was added 2-[[5-Ethyl-3-[2'-(1H-tetrazol-5-yl)biphenyl-4-yl]methyl-1,3,4-thiadiazoline-2-yliden]aminocarbonyl]-1-cyclopentenecarboxylic acid (206 mg), and the mixture was heated on water bath. After the mixture had been completely dissolved, the solvent was removed in vacuo. Ethanol was added to the residue, the precipitated solid was filtrated and dried in vacuo. The title compound (180 mg) was obtained.

IR(KBr)cm$^{-1}$ 1680(—COOH) 1570(=N—CO—)

Industrial applicability

The compounds (1) and their salts according to the present invention have a potent angiotensin II antagonist activity and are therefore useful as preventives and/or therapeutics for circulatory diseases such as hypertension, heart diseases and cerebral apoplexy.

Numerous modifications and variations of the present invention are possible in light of the above teachings, and it is therefore to be understood that within the scope of the appended claims, the invention may be practiced otherwise than as specifically described herein.

We claim:

1. A biphenylmethane derivative of formula (1-a):

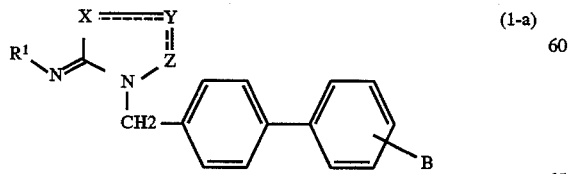

wherein:

R$^1$ represents:

a hydrogen atom, a linear or branched C$_{1-7}$ alkyl group, a C$_{3-7}$ cycloalkyl group, a phenyl group which may be substituted by 1 to 3 substituents selected from linear or branched C$_{1-7}$ alkyl, nitro or cyano groups or halogen atoms, a benzyl, phenethyl, benzhydryl or trityl group which may be substituted by 1 to 3 groups selected from carboxyl or C$_{1-7}$ alkoxycarbonyl groups, a C$_{1-10}$ alkanoyl group which may be substituted by a corresponding number of substituents selected from hydroxyl, C$_{1-7}$ alkoxyl, cyano, C$_{3-7}$ cycloalkyl, phenyl, phenoxyl, chlorophenoxyl, thiophene, furan or pyridine groups or halogen atoms, a C$_{4-7}$ cycloalkanoyl group which may be substituted by a corresponding number of groups selected from carboxyl or protected carboxyl groups, a C$_{3-7}$ alkenoyl or C$_{4-7}$ cycloalkenoyl group which may be substituted by a corresponding number of groups selected from carboxyl and protected carboxyl groups, a C$_{1-7}$ alkoxycarbonyl group, a benzyloxycarbonyl group, a phenethyloxycarbonyl group, a carbamoyl group, a C$_{1-7}$ alkylcarbamoyl group, a pyrrolidinecarbonyl group, a piperidine carbonyl group, a morpholinecarbonyl group, a benzoyl or naphthoyl group which may be substituted on its ring by 1 to 3 substituents selected from C$_{1-7}$ alkyl, cyano, nitro, halo-C$_{1-7}$ alkyl, halo-C$_{1-7}$ alkoxyl, carboxyl, protected carboxyl, C$_{1-7}$ alkoxycarbonyl, C$_{1-7}$ alkoxyl, hydroxyl, C$_{1-7}$ alkylthio, mercapto, amino, C$_{1-7}$ alkanoyl or tetrazoryl groups or halogen atoms, a thiophenecarbonyl, furancarbonyl, pyridinecarbonyl, pirazinecarbonyl, thiazolecarbonyl, benzothiophenecarbonyl or isoxazolecarbonyl group which may be substituted on its ring by 1 to 3 substituents selected from C$_{1-7}$ alkyl, cyano, nitro, halo-C$_{1-7}$ alkyl, carboxyl, C$_{1-7}$ alkoxyl, hydroxyl, C$_{1-7}$ alkylthio, mercapto, amino or C$_{1-7}$ alkanoyl groups or halogen atoms, a benzenesulfonyl group which may be substituted on its ring by 1 to 3 substituents selected from C$_{1-7}$ alkyl, cyano or nitro groups or halogen atoms, a C$_{1-7}$ alkylsulfonyl group, a glycyl group, a leucyl group, a valyl group, an alanyl group, a phenylalanyl group, an alanylalanyl group, a glycylvalyl group or a glycylglycylvalyl group, and X represents a sulfur atom, Y represents a group =CR$^2$—, Z represents a nitrogen atom, R$^2$ represents a hydrogen atom, a halogen atom, a substituted or unsubstituted lower alkyl group (wherein said substituent is selected from the group consisting of a halogen atom, a hydroxy group, a lower alkoxy group, a carboxy group and a alkoxycarbonyl group), a protected or unprotected carboxyl group, a lower cycloalkyl group, a lower alkenyl group, a lower alkoxyl group, a lower alkylthio group or an aryl group, B represents a cyano group, a protected or unprotected carboxyl group or a protected or unprotected tetrazol-5-yl group, and --- stands for a double bond or a single bond; or a salt thereof.

2. A biphenylmethane derivative according to claim 1, wherein $R^1$ represents:

a hydrogen atom, a linear or branched $C_{1-7}$ alkyl group, a $C_{3-7}$ cycloalkyl group, a phenyl group which may be substituted by 1 to 3 substituents selected from linear or branched $C_{1-7}$ alkyl, nitro or cyano groups or halogen atoms, a benzyl, phenethyl, benzhydryl or trityl group which may be substituted by 1 to 3 groups selected from carboxyl or $C_{1-7}$ alkoxycarbonyl groups, a $C_{1-10}$ alkanoyl group which may be substituted by a corresponding number of substituents selected from hydroxyl, $C_{1-7}$ alkoxyl, cyano, $C_{3-7}$ cycloalkyl, phenyl, phenoxyl, chlorophenoxyl, thiophene, furan or pyridine groups or halogen atoms, a $C_{4-7}$ cycloalkanoyl group which may be substituted by a corresponding number of groups selected from carboxyl or protected carboxyl groups, a $C_{3-7}$ alkenoyl or $C_{4-7}$ cycloalkenoyl group which may be substituted by a corresponding number of groups selected from carboxyl and protected carboxyl groups, a $C_{1-7}$ alkoxycarbonyl group, a benzyloxycarbonyl group, a phenethyloxycarbonyl group, a carbamoyl group, a $C_{1-7}$ alkylcarbamoyl group, a pyrrolidinecarbonyl group, a piperidine carbonyl group, a morpholinecarbonyl group, a benzoyl or naphthoyl group which may be substituted on its ring by 1 to 3 substituents selected from $C_{1-7}$ alkyl, cyano, nitro, halo-$C_{1-7}$ alkyl, halo-$C_{1-7}$ alkoxyl, carboxyl, protected carboxyl, $C_{1-7}$ alkoxycarbonyl, $C_{1-7}$ alkoxyl, hydroxyl, $C_{1-7}$ alkylthio, mercapto, amino, $C_{1-7}$ alkanoyl or tetrazoryl groups or halogen atoms, a thiophenecarbonyl, furancarbonyl, pyridinecarbonyl, pirazinecarbonyl, thiazolecarbonyl, benzothiophenecarbonyl or isoxazolecarbonyl group which may be substituted on its ring by 1 to 3 substituents selected from $C_{1-7}$ alkyl, cyano, nitro, halo-$C_{1-7}$ alkyl, carboxyl, $C_{1-7}$ alkoxyl, hydroxyl, $C_{1-7}$ alkylthio, mercapto, amino or $C_{1-7}$ alkanoyl groups or halogen atoms, a benzenesulfonyl group which may be substituted on its ring by 1 to 3 substituents selected from $C_{1-7}$ alkyl, cyano or nitro groups or halogen atoms, a $C_{1-7}$ alkylsulfonyl group, a glycyl group, a leucyl group, a valyl group, an alanyl group, a phenylalanyl group, an alanylalanyl group, a glycylvalyl group or a glycylglycylvalyl group, and $R^2$ represents:

a hydrogen atom, a halogen atom a $C_{1-7}$ alkyl group, a halo-$C_{1-7}$ alkyl group, a hydroxy-$C_{1-7}$ alkyl group, a $C_{1-7}$ alkoxy $C_{1-7}$ alkyl group, a carboxy $C_{1-7}$ alkyl group, a carboxycarbonyl $C_{1-7}$ alkyl group, a protected or unprotected carboxyl group, a $C_{1-7}$ cycloaklyl group, a $C_{1-7}$ alkenyl group a $C_{1-7}$ alkoxyl group, a $C_{1-7}$ alkylthio group, a phenyl group, a tolyl group, a xylyl group, a mesityl group or a napthyl group;

or a salt thereof.

3. A biphenylmethane derivative according to claim 2, wherein $R^1$ represents a $C_{1-10}$ alkanoyl group which may be substituted by a corresponding number of substituents selected from halogen atoms or hydroxyl, $C_{1-7}$ alkoxyl, cyano, $C_{3-7}$ cycloalkyl, phenyl, phenoxyl, chlorophenoxyl, thiophene, furan or pyridine groups, a $C_{4-7}$ cycloalkanoyl group which may be substituted by a corresponding number of groups selected from carboxyl or protected carboxyl groups, a $C_{3-7}$ alkenoyl or $C_{4-7}$ cycloalkenoyl group which may be substituted by a corresponding number of groups selected from carboxyl or protected carboxyl groups, a $C_{1-7}$ alkoxycarbonyl group, a benzyloxycarbonyl group, a phenethyloxycarbonyl group, a carbamoyl group, a $C_{1-7}$ alkylcarbamoyl group, a pyrrolidinecarbonyl group, a piperidine carbonyl group, a morpholinecarbonyl group, a benzoyl or naphthoyl group which may be substituted on its ring by 1 to 3 substituents selected from $C_{1-7}$ alkyl, cyano, nitro, halo-$C_{1-7}$ alkyl, halo-$C_{1-7}$ alkoxyl, carboxyl, protected carboxyl, $C_{1-7}$ alkoxycarbonyl, $C_{1-7}$ alkoxyl, hydroxyl, $C_{1-7}$ alkylthio, mercapto, amino, $C_{1-7}$ alkanoyl or tetrazoryl groups or halogen atoms, a thiophenecarboxyl, furancarbonyl, pyridinecarbonyl, pirazinecarbonyl, thiazolecarbonyl or benzothiophenecarbonyl or isoxazolecarbonyl which may be substituted on its ring by 1 to 3 substituents selected from $C_{1-7}$ alkyl, cyano, nitro, halo-$C_{1-7}$ alkyl, carboxyl, halo-$C_{1-7}$ alkoxyl, hydroxyl, $C_{1-7}$ alkylthio, mercapto, amino or $C_{1-7}$ alkanoyl groups or halogen atoms, a benzenesulfonyl group which may be substituted on its ring by 1 to 3 substituents selected from $C_{1-7}$ alkyl, cyano or nitro groups or halogen atoms, or a $C_{1-7}$ alkylsulfonyl group; or a salt thereof.

4. A biphenylmethane derivative according to claim 2, wherein the group,

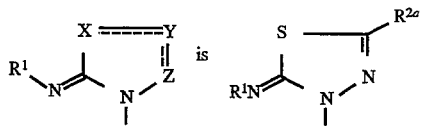

in which $R^1$ represents a $C_{1-10}$ alkanoyl group which may be substituted by a corresponding number of substituents selected from halogen atoms or hydroxyl, $C_{1-7}$ alkoxyl, cyano, $C_{3-7}$ cycloalkyl, phenyl, phenoxyl, chlorophenoxyl, thiophene, furan or pyridine groups, a $C_{4-7}$ cycloalkanoyl group which may be substituted by a corresponding number of groups selected from carboxyl or protected carboxyl groups, a $C_{3-7}$ alkenoyl or $C_{4-7}$ cycloalkenoyl group which may be substituted by a corresponding number of groups selected from carboxyl or protected carboxyl groups, or a benzoyl group which may be substituted on its ring by 1 to 3 substituents selected from $C_{1-7}$ alkyl, cyano, nitro, halo-$C_{1-7}$ alkyl, halo-$C_{1-7}$ alkoxyl, carboxyl, protected carboxyl, $C_{1-7}$ alkoxycarbonyl, $C_{1-7}$ alkoxyl, hydroxyl, $C_{1-7}$ alkylthio, mercapto, amino, $C_{1-7}$ alkanoyl or tetrazoryl groups, and $R^{2a}$ represents a hydrogen atom, a halogen atom or a $C_{1-7}$ alkyl group; or a salt thereof.

5. A biphenylmethane derivative or a salt thereof according to claim 1, which comprises 2-[[5-ethyl-3-[2'-(1H-tetrazol-5-yl)biphenyl-4-yl]methyl-1,3,4-thiadiazolin-2-yliden]aminocarbonyl]-1-cyclopentenecarboxylic acid or a salt thereof, respectively.

6. A biphenylmethane derivative or a salt thereof according to claim 2, which comprises dipotassium 2-[[5-ethyl-3-[2'-(1H-tetrazol-5-yl)biphenyl-4-yl]methyl-1,3,4-thiadiazolin-2-yliden]aminocarbonyl]-1-cyclopentenecarboxylate.

7. A pharmaceutical composition comprising a biphenylmethane derivative of claim 1, and a pharmaceutical carrier.

8. A composition according to claim 7, wherein the biphenylmethane derivative or the salt thereof is 2-[[5-ethyl-3-[2'-(1H-tetrazol-5-yl)biphenyl-4-yl]methyl-1,3,4-thiadiazolin-2-yliden]aminocarbonyl]-1-cyclopentenecarboxylic acid or a salt thereof.

9. A composition according to claim 7, wherein the diphenylmethane derivative or the salt thereof is dipotassium 2-[[5-ethyl-3-[2'-(1H-tetrazol-5-yl)biphenyl- 4-yl]methyl-1,3,4-thiadiazolin-2-yliden]-aminocarbonyl]-1-cyclopentenecarboxylate.

10. A method for treating a circulatory disease which comprises: administering an effective amount of a biphenylmethane derivative of formula (1-a):

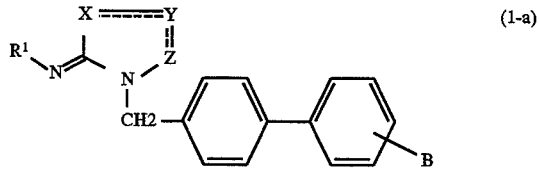

wherein:

$R^1$ represents:

a hydrogen atom, a linear or branched $C_{1-7}$ alkyl group, a $C_{3-7}$ cycloalkyl group, a phenyl group which may be substituted by 1 to 3 substituents selected from linear or branched $C_{1-7}$ alkyl, nitro or cyano groups or halogen atoms, a benzyl, phenethyl, benzhydryl or trityl group which may be substituted by 1 to 3 groups selected from carboxyl or $C_{1-7}$ alkoxycarbonyl groups, a $C_{1-10}$ alkanoyl group which may be substituted by a corresponding number of substituents selected from hydroxyl, $C_{1-7}$ alkoxyl, cyano, $C_{3-7}$ cycloalkyl, phenyl, phenoxyl, chlorophenoxyl, thiophene, furan or pyridine groups or halogen atoms, a $C_{4-7}$ cycloalkanoyl group which may be substituted by a corresponding number of groups selected from carboxyl or protected carboxyl groups, a $C_{3-7}$ alkenoyl or $C_{4-7}$ cycloalkenoyl group which may be substituted by a corresponding number of groups selected from carboxyl and protected carboxyl groups, a $C_{1-7}$ alkoxycarbonyl group, a benzyloxycarbonyl group, a phenethyloxycarbonyl group, a carbamoyl group, a $C_{1-7}$ alkylcarbamoyl group, a pyrrolidinecarbonyl group, a piperidine carbonyl group, a morpholinecarbonyl group, a benzoyl or naphthoyl group which may be substituted on its ring by 1 to 3 substituents selected from $C_{1-7}$ alkyl, cyano, nitro, halo-$C_{1-7}$ alkyl, halo-$C_{1-7}$ alkoxyl, carboxyl, protected carboxyl, $C_{1-7}$ alkoxycarbonyl, $C_{1-7}$ alkoxyl, hydroxyl, $C_{1-7}$ alkylthio, mercapto, amino, $C_{1-7}$ alkanoyl or tetrazoryl groups or halogen atoms, a thiophenecarbonyl, furancarbonyl, pyridinecarbonyl, pirazinecarbonyl, thiazolecarbonyl, benzothiophenecarbonyl or isoxazolecarbonyl group which may be substituted on its ring by 1 to 3 substituents selected from $C_{1-7}$ alkyl, cyano, nitro, halo-$C_{1-7}$ alkyl, carboxyl, $C_{1-7}$ alkoxyl, hydroxyl, $C_{1-7}$ alkylthio, mercapto, amino or $C_{1-7}$ alkanoyl groups or halogen atoms, a benzenesulfonyl group which may be substituted on its ring by 1 to 3 substituents selected from $C_{1-7}$ alkyl, cyano or nitro groups or halogen atoms, a $C_{1-7}$ alkylsulfonyl group, a glycyl group, a leucyl group, a valyl group, an alanyl group, a phenylalanyl group, an alanylalanyl group, a glycylvalyl group or a glycylglycylvalyl group, and X represents a sulfur atom, Y represents a group $=CR^2—$, Z represents a nitrogen atom, $R^2$ represents a hydrogen atom, a halogen atom, a substituted or unsubstituted lower alkyl group (wherein said substituent is selected from the group consisting of a halogen atom, a hydroxy group, a lower alkoxy group, a carboxy group and a alkoxycarbonyl group), a protected or unprotected carboxyl group, a lower cycloalkyl group, a lower alkenyl group, a lower alkoxyl group, a lower alkylthio group or an aryl group, B represents a cyano group, a protected or unprotected carboxyl group or a protected or unprotected tetrazol-5-yl group, and --- stands for a double bond or a single bond; or a salt thereof.

11. A therapeutic method according to claim 10, wherein the circulatory disease is hypertension.

12. A therapeutic method according to claim 10, wherein the diphenylmethane derivative or the salt thereof is 2-[[5-ethyl-3-[2'-(1H-tetrazol-5-yl)-biphenyl-4-yl]methyl-1,3,4-thiadiazolin-2-yliden]aminocarbonyl]-1-cyclopentenecarboxylic acid or a salt thereof.

13. A therapeutic method according to claim 10, wherein the diphenylmethane derivative or the salt thereof is dipotassium 2-[[5-ethyl-3-[2'-(1H-tetrazol-5-yl)biphenyl-4-yl]methyl-1,3,4-thiadiazolin-2-yliden]-aminocarbonyl]-1-cyclopentenecarboxylate.

* * * * *